US006500662B1

(12) United States Patent
Calvert et al.

(10) Patent No.: US 6,500,662 B1
(45) Date of Patent: Dec. 31, 2002

(54) INFECTIOUS CDNA CLONE OF NORTH AMERICAN PORCINE REPRODUCTIVE AND RESPIRATORY SYNDROME (PRRS) VIRUS AND USES THEREOF

(75) Inventors: Jay G. Calvert, Gales Ferry, CT (US); Michael G. Sheppard, North Stonington, CT (US); Siao-Kun W. Welch, North Stonington, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/470,661

(22) Filed: Dec. 22, 1999

Related U.S. Application Data

(60) Provisional application No. 60/113,345, filed on Dec. 22, 1998.

(51) Int. Cl.[7] ........................ C12N 7/00; C12N 5/10; C12N 15/40; C12N 15/63

(52) U.S. Cl. ........................ 435/235.1; 435/320.1; 435/325; 536/23.72

(58) Field of Search .................... 536/23.72; 435/235.1, 435/325, 320.1; 424/204.1

(56) References Cited

U.S. PATENT DOCUMENTS

| | | | |
|---|---|---|---|
| 3,137,631 A | | 6/1964 | Soloway |
| 3,959,457 A | | 5/1976 | Speaker et al. |
| 4,015,100 A | | 3/1977 | Gnanamuthu et al. |
| 4,205,060 A | | 5/1980 | Monsimer et al. |
| 4,452,747 A | | 6/1984 | Gersonde et al. |
| 4,606,940 A | | 8/1986 | Frank et al. |
| 4,744,933 A | | 5/1988 | Rha et al. |
| 4,921,706 A | | 5/1990 | Roberts et al. |
| 4,927,637 A | | 5/1990 | Morano et al. |
| 4,944,948 A | | 7/1990 | Uster et al. |
| 5,008,050 A | | 4/1991 | Cullis et al. |
| 5,009,956 A | | 4/1991 | Baumann |
| 5,132,117 A | | 7/1992 | Speaker et al. |
| 5,476,778 A | | 12/1995 | Chladek et al. |
| 5,620,691 A | | 4/1997 | Wensvoort et al. |
| 5,840,563 A | | 11/1998 | Chladek et al. |
| 6,197,310 B1 | | 3/2001 | Wensvoort et al. |
| 6,268,199 B1 | * | 7/2001 | Meulenberg et al. .... 435/235.1 |
| 6,288,199 B1 | * | 7/2001 | Meulenberg et al. .... 435/235.1 |
| 6,110,467 A1 | | 8/2001 | Paul et al. |

FOREIGN PATENT DOCUMENTS

| | | |
|---|---|---|
| EP | 0595436 | 10/1983 |
| EP | 0529584 | 8/1992 |
| EP | 0587780 | 3/1994 |
| EP | 0595463 | 5/1994 |
| EP | 0732340 | 3/1996 |
| EP | 0839912 | 5/1998 |
| GB | 2282811 | 4/1995 |
| WO | WO 9221375 | 12/1992 |
| WO | WO 92/21375 | 12/1992 |
| WO | WO 93/03760 | 3/1993 |
| WO | WO 9303760 | 3/1993 |
| WO | WO 9306211 | 4/1993 |
| WO | WO 9314196 | 7/1993 |
| WO | WO 9418311 | 8/1994 |
| WO | WO 95/28227 | 10/1995 |
| WO | WO 9604010 | 2/1996 |
| WO | WO 9636356 | 11/1996 |
| WO | WO 9640932 | 12/1996 |
| WO | WO 9731651 | 9/1997 |
| WO | WO 9818933 | 5/1998 |
| WO | WO 9855626 | 12/1998 |

OTHER PUBLICATIONS

Meulenberg, J.J.M., et al. "An infectious cDNA clone of Porcine Reproductive and Respiratory Syndrome Virus" Chapter 24, pp. 199–206 Coronaviruses and Arteriviruses (Advances in Experimental Medicine and Biology, vol. 440), 1998.

Meulenberg J. J. M., et al., Infectious transcripts from cloned genome–length cDNA of porcine reproductive and respiratory syndrome virus. *J. Virol.* 72(1):pp. 380–387, 1998.

Meulenberg J. J. M., et al., Posttranslational processing and identification of a neutralization domain of the gp(4) protein encoded by ORF4 of Lelystad virus. *J. Virol.* 71(8): pp. 6061–6067, 1997.

Nelsen, C. J., et al., Porcine reproductive and respiratory syndrome virus comparison: Divergent evolution on two continents. *J. Virol.* 73 (1): pp. 270–280, 1999.

Murtaugh, M. P., et al. Comparison of the Structural Protein Coding Sequences of the VR–2332 and Lelystad virus strain of the PRRS virus, Journal Arch. Virol. 140(8), pp. 1451–1460 (1995).

(List continued on next page.)

*Primary Examiner*—Mary E. Mosher
(74) *Attorney, Agent, or Firm*—Paul H. Ginsburg; Lorraine B. Ling; Kohn & Associates, PLLC

(57) ABSTRACT

The invention provides isolated polynucleotide molecules, including plasmids; viral vectors; and transfected host cells that comprise a DNA sequence encoding an infectious RNA sequence encoding a North American PRRS virus; and also North American PRRS viruses encoded thereby. The invention further provides isolated infectious RNA molecules encoding a North American PRRS virus. The invention also provides isolated polynucleotide molecules, infectious RNA molecules, viral vectors, and transfected host cells encoding genetically-modified North American PRRS viruses; and genetically-modified North American PRRS viruses encoded thereby. The invention also provides vaccines comprising such plasmids, RNA molecules, viral vectors, and North American PRRS viruses, and methods of using these vaccines in swine and in other animals. Also provided are isolated polynucleotide molecules, viral vectors, and transfected host cells that comprise a nucleotide sequence encoding a peptide of a North American PRRS virus. These viral vectors and transfected host cell lines are useful in providing peptides to compensate for mutated peptide coding sequences of DNA sequences encoding genetically-modified North American PRRS viruses so that functional virions can be generated.

6 Claims, 2 Drawing Sheets

OTHER PUBLICATIONS

Kapur, V., et al., Genetic Variation in Porcine reproductive and Respiratory Syndrome Virus Isolates in the Midwestern United States, Journal of Gen. Virol. 77, pp. 1271–1276 (1996).

Allende, R. et al., North American and European Porcine Reproductive and Respiratory Syndrome Viruses Differ in Non–Structural Protein Coding Regions, Journal Gen. Virol. 80 (Pt 2), 307–315 (1999).

Kwang, Jimmy, et al., Cloning, Expression, and Sequence Analysis of the OrF4 Gene of the Porcine Reproductive and Respiratory Syndrome Virus MN–1b, J Vet Diagn. Invest 6, pp. 293–296 (1994).

Mardassi, H., et al., Molecular Analysis of the ORF's 3 to 7 of Porcine Reproductive and Respiratory Syndrome Virus, Quebec Reference Strain, Arch Virol 140, pp. 1405–1418 (1995).

Meng, Xiang–Jin, Molecular Cloning and Nucleotide Sequencing of the 3'–Terminal Genomic RNA of the Porcine Reproductive and Respiratory Syndrome Virus, Journal of General Virology 75, pp. 1795–1801 (1994).

Allende, R., et al.., P1–19, *Fifth International Symposium on Positive Strand RNA Viruses* (St. Petersburg, Florida, May 1998).

Faaberg, K. S., et al., P2–59, *Fifth International Symposium on Positive Strand RNA Viruses* (St. Petersburg, Florida, May 1998).

Nelson, C., et al. P5–1, *American Society of Virology*, 17$^{th}$ Annual Meeting (Vancouver, Canada, Jul. 1998).

Spatz, S. J., et al., *Conference of Researcher Working on Animal Diseases* (Chicago, Nov. 1998).

J.M., Janneke, et al., Lelystad Virus, the Causative Agent of Porcine Epidemic Abortion and Respiratory Syndrome (PEARS), Is Related to LDV and EAV, Virology, (1993), 192, pp. 62–72.

Andreyev VG., Wesley RD., Mengeling WL., Vorwald AC., Lager KM., Genetic variation and phylogenetic relationships of 22 porcine reproductive and respiratory syndrome virus (PRRSV) fields starins based on sequence analysis of open reading frame 5, Arch Virol 142:993–1001, 1997.

Ausubel et al., 1989, Current Protocols In Molecular Biology, Greene Publishing Associates & Wiley Interscience, NY.

Collins JE., Benfield DA., Christianson WT., Harris L., Hennings JC., Shaw DP., Goyal SM., McCullough S., Morrison RB., Joo HS., Gorcyca D., Chladek D. Isolation of swine infertility and respiratory syndrome virus (isolate ATCC VR–2332) in North America and experimental reproduction of the disease in gnotobiotic pigs, J Vet Diagn Invest 4:117–126, 1992.

A. Domb et al., 1992, Polymers for Advanced Technologies, 3:279–292.

Kim HS., Kwang J., Yoon IJ., Joo HS., Frey, ML. Enhanced replication of porcine reproductive and respiratory syndrome (PRRS) virus in a homogeneous subpopulation of MA–104 cell line, Arch Virol 133:477–483, 1993.

Meng XJ., Paul PS., Halbur PG., Lum MA., Phylogenetic analyses of the putative M (ORF 6) and N (ORF 7) genes of porcine reproductive and respiratory syndrome virus (PRRSV): implication for the existence of two genotypes of PRRSV in the U.S.A. and Europe, Arch Virol 140:745–755, 1995.

Morozov I., Meng XJ., Paul PS., Sequence analysis of open reading frames (ORFs) 2 to 4 of a U.S. isolate of porcine reproductive and respiratory syndrome virus, Arch Virol 140:1313–1319, 1995.

Rossow KD., Porcine Reproductive and Respiratory Syndrome, Vet Pathol 35:1–20 (1998).

Sambrook et al., 1989, Molecular Cloning: A Laboratory Manual, 2$^{nd}$ ed., Cold Springs Harbor Laboratory Press, Cold Springs Harbor, NY.

Snider EJ., Meulenberg, JJM. The molecular biology of arteriviruses, Journal of General Virology, 79:961–979, 1998.

Suárez P., Zardoya R., Martin MJ., Prieto C., Dopazo J., Solana A., Castro JM. Phylogenetic relationships of European strains of porcine reproducitve and respiratory syndrome virus (PRRSV) inferred from DNA sequences of putative ORF–5 and ORF–7 genes, Virus Research 42:159–165, 1996.

Terpstra C., Wensvoort G., Pol JMA. Experimental reproduction of porcine epidemic abortion and respiratory syndrome (mystery swine disease) by infection with Lelystad virus: Koch's postulates fulfilled, The Veterinary Quarterly, vol. 13, No. 3, pp. 131–136, Jul. 1991.

Wensvoort G., Terpstra C., Pol JMA., ter Laak EA., Bloemraad M., de Kluyver EP., Kragten C., van Buiten L., den Besten A., Wagenaar F., Broekhuijsen JM., Moonen PLJM., Zetstra T., de Boer EA., Tibben HJ., de Jong MF., van't Veld P., Groenland GJR., van Gennep JA., Voets MTh., Verheijden JHM., Braamskamp J. Mystery swine disease in the Netherlands: the isolation of Lelystad virus, The Veterinary Quarterly, vol. 13, No. 3, pp. 121–130, Jul. 1991.

Zimmerman JJ., Yoon, KJ., Willis RW., Swenson SL., General overview of PRRSV: A perspective from the United States, Veterinary Microbiology 55:187–196, 1997.

Inis et al. (eds.), 1995, PCR Strategies, Academic Press, Inc., San Diego (Table of Contents Only).

Maniatis et al., 1989, Molecular Cloning, A Laboratory Manual, Cold Springs Harbor Laboratory Press, Cold Springs Harbor, NY (Table of Contents Only).

Chasin M., Domb A. "Polyanhydrides as Drug Delivery Systems" in Biodegradable Polymers as Drug Delivery Systems, vol. 45, pp. 43–70, 1990.

Den Boon, J.A. et al., 1991, J. Virol. 65(6):2910–2920.

Erlich (ed), 1992, PCR Technology, Oxford University Press, New York (Table of Contents only).

Kreutz, L.C. "Cellular membrance factors are the major determinants of porcine reproductive and respiratory syndrome virus tropism," Virus Research 53:121–128, 1998.

Van Dinten, L.D. et al., 1997, Proc. Natl. Acad. Sci. USA, 94(3):991–996.

* cited by examiner

PacI
Bsu36I (1632)
SpeI
1-1756
pT7R3A-2
1361-9438
pGAP10B-4
PacI
NdeI(9399)
SpeI
1-9438
pT7RG
9201-12,050
SpeI
p1B3A-2
PacI
Eco47III (11,785)
SpeI
1-12,050
pIA1B
SwaI
SpeI
AAA
11,504-15,395
p2_7D-4
PacI
SwaI
SpeI
AAA
1-15,395
pT7P129A

INFECTIOUS CDNA CLONE OF NORTH AMERICAN PORCINE REPRODUCTIVE AND RESPIRATORY SYNDROME (PRRS) VIRUS AND USES THEREOF

This application claims the benefit under 35 U.S.C. 119 of U.S. patent application Ser. No. 60/113,345, entitled "INFECTIOUS cDNA CLONE OF NORTH AMERICAN PORCINE REPRODUCTIVE AND RESPIRATORY SYNDROME (PRRS) VIRUS AND USES THEREOF", filed Dec. 22, 1998.

FIELD OF THE INVENTION

The present invention is in the field of animal health and is directed to infectious cDNA clones of positive polarity RNA viruses and the construction of vaccines, in particular, swine vaccines, using such cDNA clones.

BACKGROUND OF THE INVENTION

Porcine reproductive and respiratory syndrome (PRRS) is a new disease of swine, first described in 1987 in North America and in 1990 in Europe. The disease has since spread to Asia and affects most of the major swine producing countries of the world. Primary symptoms are reproductive problems in sows and gilts, including late term abortions, stillbirths and mummies, and litters of small weak pigs which are born viremic and often fail to survive. In addition, the syndrome manifests itself as a respiratory disease in young pigs which spreads horizontally and causes fever, lethargy, labored breathing, loss of appetite, slow growth, and occasionally death, often in association with other respiratory pathogens. The disease furthermore can be transmitted to sows and gilts via the semen of infected boars, either naturally or by artificial insemination. For these, and other reasons, PRRS has proven to be a difficult disease to control and therefore one of the most economically damaging diseases to the swine industry.

The causative agent of PRRS is the PRRS virus, which exists as two genetically and serologically distinct types (Murtaugh, M. P. et al., 1995, Arch-Virol. 140, 1451–1460; Suarez, P. et al., 1996, Virus Research 42:159–165). The two types are believed to have first entered swine populations independently, one in North America and the other in Europe, in the1980's, from unknown biological reservoirs, possibly of rodent or avian origin. The European type, represented by the prototype "Lelystad Virus", was isolated and sequenced in the Netherlands in 1991 (Terpstra, C. et al., 1991, Vet. Quart. 13:131–136; Wensvoort, G. et al., 1991, Vet. Quart. 13:121–130; Wensvoort, G. et al., WO 92/213751992 (PCT/NL92/00096), 1992; Meulenberg, J. J. M. et al., 1993, Virol. 192:62–72).

Both the North American PRRS virus and the European PRRS virus are classified within the family Arteriviridae, which also includes equine arteritis virus, lactate dehydrogenase-elevating virus, and simian haemorrhagic fever virus. The arteriviruses are in turn placed within the order Nidovirales, which also includes the coronaviruses and toroviruses. The nidoviruses are enveloped viruses having genomes consisting of a single strand of positive polarity RNA. The genomic RNA of a positive-stranded RNA virus fulfills the dual role in both storage and expression of genetic information. No DNA is involved in replication or transcription in nidoviruses. The reproduction of nidoviral genomic RNA is thus a combined process of genome replication and mRNA transcription. Moreover, some proteins are translated directly from the genomic RNA of nidoviruses. The molecular biology of the family Arteriviridae has recently been reviewed by Snijder and Meulenberg (Snijder, E. J. and Meulenberg, J. J. M., 1998, Journal of General Virology 79:961–979).

Currently available commercial vaccines against PRRS are either conventional modified live virus (cell culture, attenuated) or conventional killed (inactivated cell culture preparations of virulent virus). Several of these vaccines have been criticized based on safety and/or efficacy concerns. The development of a second generation of PRRS vaccines, based upon specific additions, deletions, and other modifications to the PRRS genome, is therefore highly desirable. However, since the PRRS viruses do not include any DNA intermediates during their replication, such vaccines have thus far awaited the construction of full-length cDNA clones of PRRS viruses for manipulation by molecular biology techniques at the DNA level. Very recently, a full-length infectious cDNA clone of the European PRRS virus has been reported (Meulenberg, J. J. M. et al., 1998, supra; Meulenberg, J. J. M. et al., 1988, J. Virol. 72, 380–387.).

The preceding publications, as well as all other references discussed below in this application, are hereby incorporated by reference in their entireties.

SUMMARY OF THE INVENTION

The subject invention provides an isolated polynucleotide molecule comprising a DNA sequence encoding an infectious RNA molecule encoding a North American PRRS virus, wherein said DNA sequence is SEQ ID NO:1 or is a sequence homologous thereto.

The subject invention further provides an isolated infectious RNA molecule encoded by the isolated polynucleotide molecule recited above, and isolated infectious RNA molecules homologous thereto, which isolated infectious RNA molecules each encode a North American PRRS virus.

The subject invention further provides the above-recited isolated polynucleotide molecule encoding the infectious RNA molecule in the form of a vector such as a plasmid.

The subject invention further provides a viral vector comprising a DNA encoding an infectious RNA molecule encoding a North American PRRS virus, wherein said DNA sequence is SEQ ID NO:1 or is a DNA sequence homologous thereto.

The subject invention further provides a transfected host cell comprising a DNA sequence encoding an infectious RNA molecule encoding a North American PRRS virus, wherein said DNA sequence is SEQ ID NO:1 or is a DNA sequence homologous thereto, which transfected host cell is capable of expressing the encoded North American PRRS virus.

The subject invention further provides a method for making a genetically modified North American PRRS virus, which method comprises mutating a DNA sequence of the present invention encoding an infectious RNA molecule encoding the North American PRRS virus, and expressing the genetically modified North American PRRS virus therefrom subsequent to said mutation.

The subject invention further provides an isolated polynucleotide molecule comprising a DNA sequence encoding an infectious RNA molecule encoding a genetically modified North American PRRS virus. In a preferred embodiment, the PRRS virus is genetically modified such that when it infects a porcine animal it is: a) unable to produce PRRS in the animal, and b) able to elicit an effective immunoprotective response against infection by a PRRS virus in the animal. In a particular embodiment, the DNA sequence is SEQ ID NO:1 or a sequence homologous thereto, except for that it contains one or more mutations that genetically disable the encoded PRRS virus in its ability to produce PRRS.

The subject invention further provides an isolated infectious RNA molecule encoded by the isolated polynucleotide molecule recited above, and isolated infectious RNA molecules homologous thereto, which isolated infectious RNA molecules each encode a genetically modified North American PRRS virus, disabled in its ability to produce PRRS.

The subject invention further provides a genetically modified North American PRRS virus encoded by an infectious RNA molecule as recited above, which genetically modified North American PRRS virus is disabled such that when it infects a porcine animal it is unable to produce PRRS in the animal, yet is able to elicit an effective immunoprotective response against infection by a PRRS virus in the animal.

The subject invention further provides a viral vector comprising a DNA sequence encoding an infectious RNA molecule encoding a genetically modified North American PRRS virus as recited above.

The subject invention further provides a transfected host cell comprising a DNA sequence encoding an infectious RNA molecule encoding a genetically modified North American PRRS virus as recited above.

The subject invention further provides a vaccine for protecting a porcine animal from infection by a PRRS virus, which vaccine comprises a genetically modified North American PRRS virus as recited above; an infectious RNA molecule as recited above encoding the genetically modified North American PRRS virus; an isolated polynucleotide molecule recited above, in the form of a plasmid, encoding the genetically modified North American PRRS virus; or the above-recited viral vector encoding the genetically modified North American PRRS virus; in an amount effective to produce immunoprotection against infection by a PRRS virus; and a carrier acceptable for veterinary use.

The subject invention further provides a method for protecting a porcine animal from infection by a PRRS virus, which comprises vaccinating the animal with an amount of the above-recited vaccine that is effective to produce immunoprotection against infection by a PRRS virus.

The present invention further provides any of the aforementioned polynucleotide molecules further comprising a nucleotide sequence encoding a heterologous antigenic epitope, as well as corresponding infectious RNA molecules, vectors, transfected host cells, genetically modified North American PRRS viruses, vaccines, and methods of administering such vaccines to mammals and/or birds. Such heterologous antigenic epitopes can be from any antigenic epitope, presently known in the art, or to be determined in the future. In a non-limiting embodiment, such antigenic epitope is from a pathogen capable of pathogenically infecting a bird or mammal other than porcine animal, for example a human, and is capable of inducing an effective immunoprotective response against said pathogen. In another non-limiting embodiment, such antigenic epitope is from a swine pathogen other than a North American PRRS virus and is capable of inducing an effective immunoprotective response against said swine pathogen. In another non-limiting embodiment, such antigenic epitope is a detectable antigenic epitope.

The present invention further provides any of the aforementioned polynucleotide molecules, but which lack one or more detectable antigenic epitopes, as well as corresponding infectious RNA molecules, vectors, transfected host cells, genetically modified North American PRRS viruses, vaccines, and methods of administering such vaccines to mammals and/or birds.

The subject invention further provides an isolated polynucleotide molecule comprising one or more nucleotide sequences that encode a peptide encoded by a North American PRRS virus, wherein the genome sequence of said North American PRRS virus is SEQ ID NO:1 or a sequence homologous thereto.

The subject invention further provides a transfected host cell comprising one or more nucleotide sequences that encode a peptide encoded by a North American PRRS virus, wherein the genome sequence of said North American PRRS virus is SEQ ID NO:1 or a sequence homologous thereto.

The subject invention further provides a genetically modified Nidovirales virus that is able to elicit an effective immunoprotective response in a mammal or a bird vaccinated therewith, which genetically modified Nidovirales virus is prepared by obtaining an isolated polynucleotide molecule comprising a DNA sequence encoding an infectious RNA molecule encoding a wild-type Nidovirales virus, genetically mutating the DNA sequence so as to obtain an isolated polynucleotide molecule comprising a DNA sequence encoding an infectious RNA molecule encoding a genetically modified Nidovirales virus which virus is unable to produce a pathogenic infection yet is able to elicit an effective immunoprotective response against infection by the wild-type Nidovirales virus in a mammal or a bird, and expressing the genetically modified Nidovirales virus from the isolated polynucleotide molecule so obtained.

The subject invention further provides a method for preparing a genetically modified Nidovirales virus that is capable of eliciting an immunoprotective response in a mammal or a bird vaccinated therewith, which method comprises obtaining an isolated polynucleotide molecule comprising a DNA sequence encoding an infectious RNA molecule encoding a wild-type Nidovirales virus, genetically mutating the DNA so as to obtain an isolated polynucleotide molecule comprising a DNA sequence encoding an infectious RNA molecule encoding a genetically modified Nidovirales virus which virus is unable to produce a pathogenic infection yet able to elicit an effective immunoprotective response against infection by the wild-type Nidovirales virus in a mammal or a bird, and expressing the genetically modified Nidovirales virus from the isolated polynucleotide molecule so obtained.

The subject invention further provides a vaccine for protecting a mammal or a bird from infection by a Nidovirales virus, which vaccine comprises a genetically modified Nidovirales virus as described above in an amount effective to elicit an effective immunoprotective response against the wild-type Nidovirales virus in a mammal or a bird vaccinated therewith, and a carrier acceptable for pharmaceutical or veterinary use.

Figure 1:
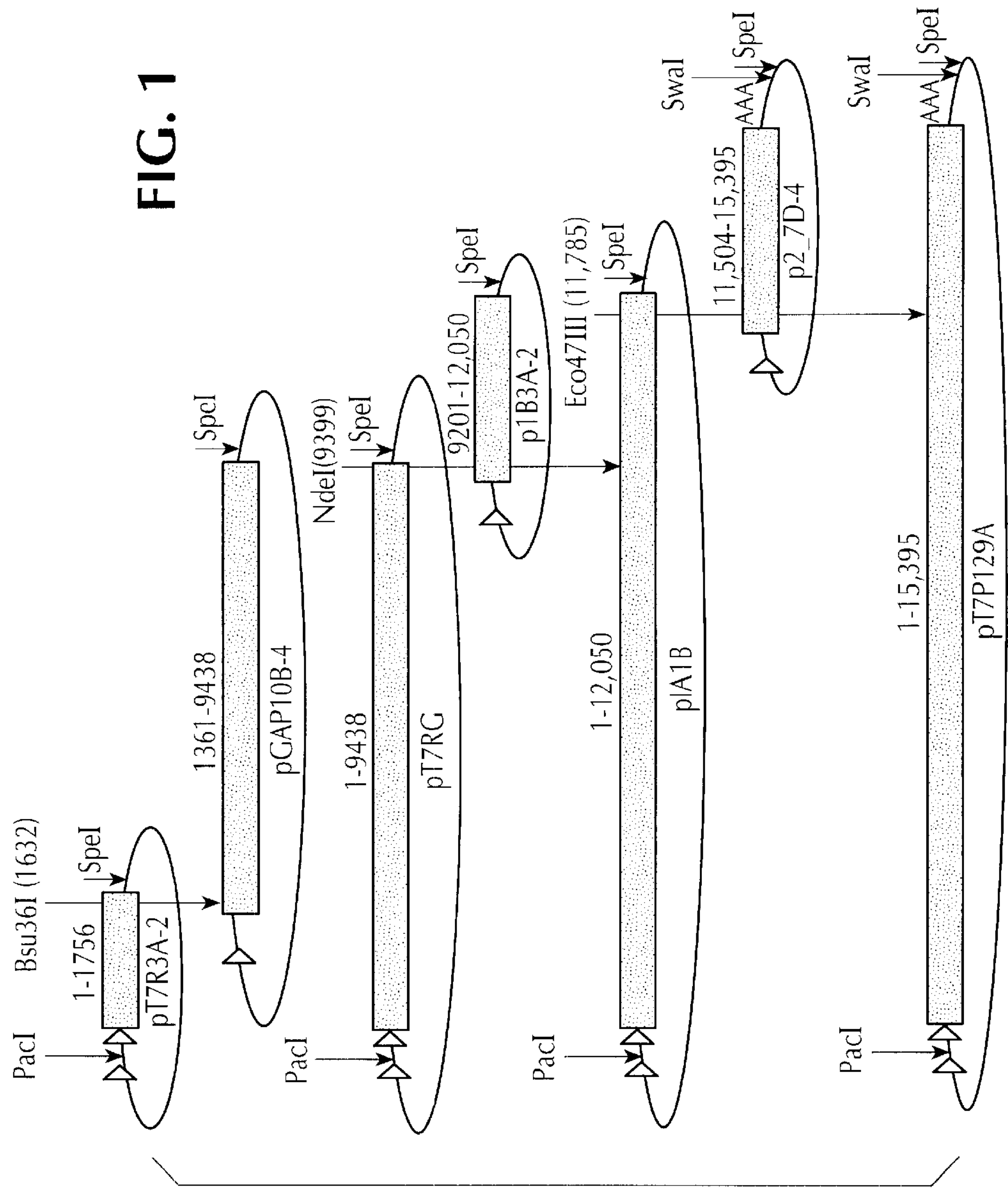
FIG. 1: Cloning strategy for construction of full-length infectious cDNA clone of North American PRRS virus, pT7P129A. Arrowheads represent T7 promoter sequences.

Determined by HerdChek PRRS ELISA assay (IDEXX (Westbrook, Me. USA)).

DETAILED DESCRIPTION OF THE INVENTION

Production and manipulation of the isolated polynucleotide molecules described herein are within the skill in the art and can be carried out according to recombinant techniques described, among other places, in Maniatis, et al., 1989, *Molecular Cloning, A Laboratory Manual*, Cold Spring Harbor Laboratory Press, Cold Spring Harbor, N.Y.; Ausubel, et al., 1989, *Current Protocols In Molecular Biology*, Greene Publishing Associates & Wiley Interscience, N.Y.; Sambrook, et al., f1989, *Molecular Cloning: A Laboratory Manual*, 2d ed., Cold Spring Harbor Laboratory Press, Cold Spring Harbor, N.Y.; Innis et al. (eds), 1995, *PCR Strategies*, Academic Press, Inc., San Diego; and Erlich (ed), 1992, *PCR Technology*, Oxford University Press, N.Y., all of which are incorporated herein by reference.

A. Isolated Polynucleotide Molecules and RNA Molecules Encoding a North American PRRS Virus, and Isolated Polynucleotide Molecules and RNA Molecules Encoding Genetically Modified North American PRRS Viruses:

The subject invention provides isolated polynucleotide molecules comprising DNA sequences that encode infectious RNA molecules that encode a North American PRRS virus.

The present invention further provides isolated polynucleotide molecules comprising DNA sequences that encode infectious RNA molecules that encode genetically modified North American PRRS viruses.

In particular, the subject invention provides an isolated polynucleotide molecule comprising a DNA sequence encoding an infectious RNA molecule that encodes a North American PRRS virus, wherein said DNA sequence is SEQ ID NO:1 or a sequence homologous thereto. In a preferred embodiment, the present invention provides an isolated polynucleotide molecule comprising a DNA sequence encoding an infectious RNA molecule that encodes a North American PRRS virus, wherein said DNA sequence is the sequence beginning with and including nucleotide 1 through and including nucleotide 15,416 of SEQ ID NO:1, except that the nucleotide corresponding to nucleotide 12,622 of SEQ ID NO:1 is a guanine instead of an adenine and the nucleotide corresponding to nucleotide 1,559 of SEQ ID NO:1 is a thymine instead of a cytosine. Said DNA sequence encodes an infectious RNA molecule that is the RNA genome of the North American PRRS isolate P129.

It is understood that terms herein referring to nucleic acid molecules such as "isolated polynucleotide molecule", "nucleotide sequence", "open reading frame (ORF)", and the like, unless otherwise specified, include both DNA and RNA molecules and include both single-stranded and double-stranded molecules. Also, when reference to a particular sequence from the "Sequence Listing" section of the subject application is made, it is intended, unless otherwise specified, to refer to both the DNA of the "Sequence Listing", as well as RNA corresponding to the DNA sequence, and includes sequences complementary to the DNA and RNA sequences. In such contexts in this application, "corresponding to" refers to sequences of DNA and RNA that are identical to one another but for the fact that the RNA sequence contains uracil in place of thymine and the backbone of the RNA molecule contains ribose instead of deoxyribose.

For example, SEQ ID NO:1 is a DNA sequence corresponding to the RNA genome of a North American PRRS virus. Thus, a DNA sequence complementary to the DNA sequence set forth in SEQ ID NO:1 is a template for, i.e. is complementary to or "encodes", the RNA genome of the North American PRRS virus (i.e., RNA that encodes the North American PRRS virus). Nonetheless, a reference herein to SEQ ID NO:1 includes both the RNA sequence corresponding to SEQ ID NO:1 and a DNA sequence complementary to SEQ ID NO:1.

Furthermore, when reference is made herein to sequences homologous to a sequence in the Sequence Listing, it is to be understood that sequences homologous to a sequence corresponding to the sequence in the Sequence Listing and sequences homologous to a sequence complementary to the sequence in the Sequence Listing are also included.

An "infectious RNA molecule", for purposes of the present invention, is an RNA molecule that encodes the necessary elements for viral replication, transcription, and translation into a functional virion in a suitable host cell, provided, if necessary, with a peptide or peptides that compensate for any genetic modifications, e.g. sequence deletions, in the RNA molecule.

An "isolated infectious RNA molecule" refers to a composition of matter comprising the aforementioned infectious RNA molecule purified to any detectable degree from its naturally occurring state, if such RNA molecule does indeed occur in nature. Likewise, an "isolated polynucleotide molecule" refers to a composition of matter comprising a polynucleotide molecule of the present invention purified to any detectable degree from its naturally occurring state, if any.

For purposes of the present invention, the nucleotide sequence of a second polynucleotide molecule (either RNA or DNA) is "homologous" to the nucleotide sequence of a first polynucleotide molecule where the nucleotide sequence of the second polynucleotide molecule encodes the same polyaminoacid as the nucleotide sequence of the first polynucleotide molecule as based on the degeneracy of the genetic code, or when it encodes a polyaminoacid that is sufficiently similar to the polyaminoacid encoded by the nucleotide sequence of the first polynucleotide molecule so as to be useful in practicing the present invention. For purposes of the present invention, a polynucleotide molecule is useful in practicing the present invention where it can be used as a diagnostic probe to detect the presence of the North American PRRS virus in a fluid or tissue sample of an infected pig, e.g. by standard hybridization or amplification techniques. It is to be understood that the polyaminoacid encoded by the nucleotide sequence of the polynucleotide molecule can comprise a group of two or more polyaminoacids. Generally, the nucleotide sequence of a second polynucleotide molecule is homologous to the nucleotide sequence of a first polynucleotide molecule if it has at least about 70% nucleotide sequence identity to the nucleotide sequence of the first polynucleotide molecule as based on the BLASTN algorithm (National Center for Biotechnology Information, otherwise known as NCBI, (Bethesda, Md., USA) of the United States National Institute of Health). Preferably, a homologous nucleotide sequence has at least about 75% nucleotide sequence identity, even more preferably at least about 85% nucleotide sequence identity. Since the genetic code is degenerate, a homologous nucleotide sequence can include any number of "silent" base changes, i.e. nucleotide substitutions that nonetheless encode the same amino acid. A homologous nucleotide sequence can further contain non-silent mutations, i.e. base substitutions, deletions, or additions resulting in amino acid differences in the encoded polyaminoacid, so long as the sequence remains at least about 70% identical to the polyaminoacid encoded by the first nucleotide sequence or otherwise is useful for practicing the present invention. Homologous nucleotide sequences can be determined by comparison of nucleotide sequences, for example by using BLASTN, above. Alternatively, homologous nucleotide sequences can be determined by hybridization under selected conditions. For example, the nucleotide sequence of a second polynucleotide molecule is homologous to SEQ ID NO:1 if it hybridizes to the complement of SEQ ID NO:1 under moderately stringent conditions, e.g., hybridization to filter-bound DNA in 0.5 M $NaHPO_4$, 7% sodium dodecyl sulfate (SDS), 1 mM EDTA at 65° C., and washing in 0.2×SSC/0.1% SDS at 42° C. (see Ausubel et al. above), or conditions which will otherwise result in hybridization of sequences that encode a North American PRRS virus as defined below. In another embodiment, a second nucleotide sequence is homologous to SEQ ID NO:1 if it hybridizes to the complement of SEQ ID NO:1 under highly stringent conditions, e.g. hybridization to filter-bound DNA in 0.5 M $NaHPO_4$, 7% SDS, 1 mM EDTA at 65° C., and washing in 0.1×SSC/0.1% SDS at 68° C. (Ausubel et al., above).

It is furthermore to be understood that the isolated polynucleotide molecules and the isolated RNA molecules of the present invention include both synthetic molecules and molecules obtained through recombinant techniques, such as by in vitro cloning and transcription.

As used herein, the term "PRRS" encompasses disease symptoms in swine caused by a PRRS virus infection. Examples of such symptoms include, but are not limited to, abortion in pregnant females, and slow growth, respiratory difficulties, loss of appetite, and mortality in young pigs. As used herein, a PRRS virus that is "unable to produce PRRS" refers to a virus that can infect a pig, but which does not produce any disease symptoms normally associated with a PRRS infection in the pig, or produces such symptoms, but to a lesser degree, or produces a fewer number of such symptoms, or both.

The terms "porcine" and "swine" are used interchangeably herein and refer to any animal that is a member of the family Suidae such as, for example, a pig. "Mammals" include any warm-blooded vertebrates of the Mammalia class, including humans.

The term "PRRS virus", as used herein, unless otherwise indicated, means any strain of either the North American or European PRRS viruses.

The term "North American PRRS virus" means any PRRS virus having genetic characteristics associated with a North American PRRS virus isolate, such as, but not limited to the PRRS virus that was first isolated in the United States around the early 1990's (see, e.g., Collins, J. E., et al., 1992, J. Vet. Diagn. Invest. 4:117–126); North American PRRS virus isolate MN-1b (Kwang, J. et al., 1994, *J.Vet.Diagn.Invest*. 6:293–296); the Quebec IAF-exp91 strain of PRRS (Mardassi, H. et al., 1995, *Arch.Virol*. 140:1405–1418); and North American PRRS virus isolate VR 2385 (Meng, X.-J et al., 1994, *J.Gen.Virol*. 75:1795–1801). Genetic characteristics refers to genomic nucleotide sequence similarity and aminoacid sequence similarity shared by North American PRRS virus strains. For purposes of the present invention, a North American PRRS virus is a virus that is encoded by an RNA sequence the same as or homologous to SEQ ID NO:1, wherein the term "homologous" is as defined previously. Thus, strains of North American PRRS viruses have, preferably, at least about 70% genomic nucleotide sequence identity with SEQ ID NO:1, and more preferably at least about 75% genomic nucleotide sequence identity with SEQ ID NO:1, at least about 85% genomic nucleotide sequence identity with SEQ ID NO:1 being even more preferred.

The term "European PRRS virus" refers to any strain of PRRS virus having the genetic characteristics associated with the PRRS virus that was first isolated in Europe around 1991 (see, e.g., Wensvoort, G., et al., 1991, Vet. Q. 13:121–130). "European PRRS virus" is also sometimes referred to in the art as "Lelystad virus".

Unless otherwise indicated, a North American PRRS virus is "useful in practicing the present invention" if its characteristics are within the definition of a North American PRRS virus set forth herein. For example, a virus encoded by one of the isolated polynucleotide molecules of the present invention is a "North American PRRS virus useful in practicing the present invention" if it, e.g., has genetic characteristics associated with a North American PRRS virus.

Other polyaminoacids are "useful in practicing the present invention", e.g., peptides encoded by polynucleotide sequences homologous to North American PRRS virus ORFs, if they can compensate for an RNA molecule encoding a genetically modified PRRS virus, deficient in a gene essential for expressing functional PRRS virions, in a transfected host cell so that functional PRRS virions can be generated by the cell.

The term "open reading frame", or "ORF", as used herein, means the minimal nucleotide sequence required to encode a particular PRRS virus protein without an intervening stop codon.

Terms such as "suitable host cell" and "appropriate host cell", unless otherwise indicated, refer to cells into which RNA molecules (or isolated polynucleotide molecules or viral vectors comprising DNA sequences encoding such RNA molecules) of the present invention can be transformed or transfected. "Suitable host cells" for transfection with such RNA molecules, isolated polynucleotide molecules, or viral vectors, include mammalian, particularly porcine, and avian cells, and are described in further detail below.

A "functional virion" is a virus particle that is able to enter a cell capable of hosting a PRRS virus, and express genes of its particular RNA genome (either an unmodified genome or a genetically modified genome as described herein) within the cell. Cells capable of hosting a PRRS virus include porcine alveolar macrophage cells and MARC 145 monkey kidney cells. Other mammalian or avian cells, especially other porcine cells, may also serve as suitable host cells for PRRS virions.

The isolated polynucleotide molecules of the present invention encode North American PRRS viruses that can be used to prepare live, killed, or attenuated vaccines using art-recognized methods for protecting swine from infection by a PRRS virus, as described in further detail below. These isolated polynucleotide molecules are also useful as vectors for delivering heterologous genes into mammals, including swine, or birds, as is also described in detail below. Furthermore, these isolated polynucleotide molecules are useful because they can be mutated using molecular biology techniques to encode genetically-modified North American PRRS viruses useful, inter alia, as vaccines for protecting swine from PRRS infection. Such genetically-modified North American PRRS viruses, as well as vaccines comprising them, are also described in further detail below.

Accordingly, the subject invention further provides a method for making a genetically modified North American PRRS virus, which method comprises mutating the DNA sequence encoding an infectious RNA molecule which encodes the North American PRRS virus as described above, and expressing the genetically modified North American PRRS virus using a suitable expression system. A North American PRRS virus, either wild-type or genetically modified, can be expressed from an isolated polynucleotide molecule using suitable expression systems generally known in the art, examples of which are described in this application. For example, the isolated polynucleotide molecule can be in the form of a plasmid capable of expressing the encoded virus in a suitable host cell in vitro, as is described in further detail below.

The term "genetically modified", as used herein and unless otherwise indicated, means genetically mutated, i.e. having one or more nucleotides replaced, deleted and/or added. Polynucleotide molecules can be genetically mutated using recombinant techniques known to those of ordinary skill in the art, including by site-directed mutagenesis, or by random mutagenesis such as by exposure to chemical mutagens or to radiation, as known in the art. In one embodiment, genetic modification of the North American PRRS virus of the present invention renders the virus unable to replicate effectively, or reduces its ability to replicate effectively, in a bird or mammal in which the wild-type virus otherwise can effectively replicate. In another embodiment, the genetically modified North American PRRS virus of the present invention remains able to replicate effectively in birds or mammals infected therewith. "Effective replication" means the ability to multiply and produce progeny viruses (virions) in an infected animal, i.e. the ability to "productively infect" an animal.

The subject invention further provides an isolated polynucleotide molecule comprising a DNA sequence encoding an infectious RNA molecule which encodes a genetically modified North American PRRS virus that is unable to produce PRRS in a porcine animal, wherein the DNA sequence encoding the infectious RNA molecule encoding said North American PRRS virus is SEQ ID NO:1 or a sequence homologous thereto, except that it contains one or more mutations that genetically disable the encoded PRRS virus in its ability to produce PRRS. "Genetically disabled" means that the PRRS virus is unable to produce PRRS in a swine animal infected therewith.

In one embodiment, the genetically modified North American PRRS virus disabled in its ability to cause PRRS is able to elicit an effective immunoprotective response against infection by a PRRS virus in a swine animal. Accordingly, the subject invention also provides an isolated polynucleotide molecule comprising a DNA sequence encoding an infectious RNA molecule which encodes a North American PRRS virus that is genetically modified such that when it infects a porcine animal it: a) is unable to produce PRRS in the animal, and b) is able to elicit an effective immunoprotective response against infection by a PRRS virus in the animal, wherein the DNA sequence encoding said North American PRRS virus is SEQ ID NO:1 or a sequence homologous thereto, except that it contains one or more mutations that genetically disable the encoded PRRS virus in its ability to produce PRRS.

The term "immune response" for purposes of this invention means the production of antibodies and/or cells (such as T lymphocytes) that are directed against, or assist in the decomposition or inhibition of, a particular antigenic epitope or particular antigenic epitopes. The phrases "an effective immunoprotective response", "immunoprotection", and like terms, for purposes of the present invention, mean an immune response that is directed against one or more antigenic epitopes of a pathogen so as to protect against infection by the pathogen in a vaccinated animal. For purposes of the present invention, protection against infection by a pathogen includes not only the absolute prevention of infection, but also any detectable reduction in the degree or rate of infection by a pathogen, or any detectable reduction in the severity of the disease or any symptom or condition resulting from infection by the pathogen in the vaccinated animal as compared to an unvaccinated infected animal. An effective immunoprotective response can be induced in animals that have not previously been infected with the pathogen and/or are not infected with the pathogen at the time of vaccination. An effective immunoprotective response can also be induced in an animal already infected with the pathogen at the time of vaccination.

An "antigenic epitope" is, unless otherwise indicated, a molecule that is able to elicit an immune response in a particular animal or species. Antigenic epitopes are proteinaceous molecules, i.e. polyaminoacid sequences, optionally comprising non-protein groups such as carbohydrate moieties and/or lipid moieties.

The term "pathogenically infecting" used herein refers to the ability of a pathogen to infect an animal and cause a disease in the animal. As an example, a PRRS virus is capable of pathogenically infecting a porcine animal since it can cause PRRS in swine. However, although a PRRS virus may be able to infect, either productively or non-productively, a bird or another mammal, such as a human, it does not pathogenically infect any animal other than a porcine animal since it does not cause any disease in animals other than porcine animals.

The genetically modified North American PRRS viruses encoded by the above-described isolated polynucleotide molecules are, in one embodiment, able to elicit an effective immunoprotective response against infection by a PRRS virus. Such genetically modified North American PRRS viruses are preferably able to elicit an effective immunoprotective response against any strain of PRRS viruses, including both European and North American strains.

In one embodiment, the mutation or mutations in the isolated polynucleotide molecule encoding the genetically disabled North American PRRS virus are non-silent and occur in one or more open reading frames of the nucleotide sequence encoding the North American PRRS virus; i.e., the mutation or mutations occur in one or more of the sequences within the nucleotide sequence encoding the North American PRRS virus that are the same as or homologous to ORFs 1a, 1b, 2, 3, 4, 5, 6, or 7 of SEQ ID NO:1. In another embodiment, the mutation or mutations occur in one or more noncoding regions of the North American PRRS virus genome, such as, for example, in the leader sequence of the North American PRRS virus genome; i.e., the mutation or mutations occur within the sequence that is the same as or homologous to the sequence of nucleotides 1–191 of SEQ ID NO:1. In the same isolated polynucleotide molecule, mutations can occur in both coding and noncoding regions.

As used herein, unless otherwise indicated, "noncoding regions" of the nucleotide sequence encoding the North American PRRS virus refer to those sequences of RNA that are not translated into a protein and those sequences of cDNA that encode such RNA sequences. Coding regions refer to those sequences of RNA from which North American PRRS virus proteins are expressed, and also refer to cDNA that encodes such RNA sequences. Likewise, "ORFs" refer both to RNA sequences that encode North American PRRS virus proteins and to cDNA sequence encoding such RNA sequences.

Determining suitable locations for a mutation or mutations that will encode a North American PRRS virus that is genetically disabled so that it is unable to produce PRRS yet remains able to elicit an effective immunoprotective response against infection by a PRRS virus can be made based on the SEQ ID NO:1 provided herein. One of ordinary skill can refer to the sequence of the infectious cDNA clone of North American PRRS virus provided by this invention, make sequence changes which will result in a mutation, and test the viruses encoded thereby both for their ability to produce PRRS in swine, and to elicit an effective immunoprotective response against infection by a PRRS virus. In so doing, one of ordinary skill can refer to techniques known in the art and also those described and/or exemplified herein.

For example, an ORF of the sequence encoding the infectious RNA molecule encoding the North American PRRS virus can be mutated and the resulting genetically modified North American PRRS virus tested for its ability to cause PRRS. The ORF of a North American PRRS virus encodes proteins as follows: ORF la encodes a polyprotein comprising protease function; ORF 1b encodes a polyprotein comprising replicase (RNA polymerase) and helicase functions; ORFs 2, 3, and 4 encode small membrane glycoproteins; ORF 5 encodes a major envelope glycoprotein; ORF 6 encodes a nonglycosylated integral membrane protein; and ORF 7 encodes a nucleocapsid protein. Genetic mutations of one or more of these ORFs can be used in preparing the genetically modified North American PRRS viruses described infra.

The subject invention also provides an isolated polynucleotide molecule comprising a DNA sequence encoding an infectious RNA molecule encoding a North American PRRS virus that is genetically modified such that it comprises one or more heterologous antigenic epitopes, wherein the DNA sequence encoding the RNA molecule encoding the North American PRRS virus is SEQ ID NO:1 or a sequence homologous thereto, and further comprising one or more additional nucleotide sequences that each encode a heterologous antigenic epitope, and wherein each heterologous antigenic epitope is capable of inducing an effective immunoprotective response against a particular pathogen in a mammal or a bird.

A pathogen against which an effective immunoprotective response can be induced by means of the above recited aspect of the present invention is any pathogen, such as a virus, bacteria, fungus, or protozoan, capable of causing a disease in a mammal or bird, which pathogen comprises or has associated therewith one or more antigenic epitopes which can be used to induce an effective immunoprotective response against the pathogen in the mammal or bird.

The term "heterologous antigenic epitope" for purposes of the present invention means an antigenic epitope, as defined above, not normally found in a wild-type North American PRRS virus. A nucleotide sequence encoding a heterologous antigenic epitope can be inserted into a North American PRRS viral genome using known recombinant techniques. Antigenic epitopes useful as heterologous antigenic epitopes for the present invention include additional North American PRRS virus antigenic epitopes, antigenic epitopes from European PRRS viruses, antigenic epitopes from swine pathogens other than PRRS viruses, or antigenic epitopes from pathogens that pathogenically infect birds or mammals other than swine, including humans. Sequences encoding such antigenic epitopes are known in the art or are provided herein. For example, a second North American PRRS virus envelope protein, encoded by North American PRRS ORF 5 described herein, can be inserted into a DNA sequence encoding an RNA molecule encoding a North American PRRS virus of the present invention to generate a genetically modified North American PRRS virus comprising an additional envelope protein as a heterologous antigenic epitope. Such a genetically modified North American PRRS virus can be used to induce a more effective immunoprotective response against PRRS viruses in a porcine animal vaccinated therewith.

Examples of an antigenic epitope from a swine pathogen other than a North American PRRS virus include, but are not limited to, an antigenic epitope from a swine pathogen selected from the group consisting of European PRRS, porcine parvovirus, porcine circovirus, a porcine rotavirus, swine influenza, pseudorabies virus, transmissible gastroenteritis virus, porcine respiratory coronavirus, classical swine fever virus, African swine fever virus, encephalomyocarditis virus, porcine paramyxovirus, *Actinobacillus pleuropneumoni, Bacillus anthraci, Bordetella bronchiseptica, Clostridium haemolyticum, Clostridium perfringens, Clostridium tetani, Escherichia coli, Erysipelothdix rhusiopathiae, Haemophilus parasuis*, Leptospira spp., *Mycoplasma hyopneumoniae, Mycoplasma hyorhinis, Pasteurella haemolytica, Pasteurella multocida, Salmonella choleraesuis, Salmonella typhimurium, Streptococcus equismilis*, and *Streptococcus suis*. Nucleotide sequences encoding antigenic epitopes from the aforementioned swine pathogens are known in the art and can be obtained from public gene databases such as GenBank (http://www.ncbi.nlm.nih.gov/Web/Genbank/index.html) provided by NCBI.

If the heterologous antigenic epitopes are antigenic epitopes from one or more other swine pathogens, then the isolated polynucleotide molecule can further contain one or more mutations that genetically disable the encoded PRRS virus in its ability to produce PRRS. Such isolated polynucleotide molecules and the viruses they encode are useful for preparing vaccines for protecting swine against the swine pathogen or pathogens from which the heterologous antigenic epitopes are derived.

In a preferred embodiment, the genetically modified North American PRRS is able to elicit an effective immunoprotective response against infection by a PRRS virus in a porcine animal. Such isolated polynucleotide molecules and the viruses they encode are useful for preparing dual-function vaccines for protecting swine against infection by both a North American PRRS virus and the swine pathogen or pathogens from which the heterologous antigenic epitopes are derived. In another preferred embodiment, the genetically modified North American PRRS virus useful in a dual-function vaccine is genetically disabled.

The isolated polynucleotide molecules of the present invention comprising nucleotide sequences encoding heterologous antigenic epitopes can be prepared as described above based on the sequence encoding a North American PRRS virus described herein using known techniques in molecular biology.

In a further preferred embodiment, a heterologous antigenic epitope of the genetically modified North American PRRS virus of the present invention is a detectable antigenic epitope. Such isolated polynucleotide molecules and the North American PRRS viruses they encode are useful, inter alia, for studying PRRS infections in swine, determining successfully vaccinated swine, and/or for distinguishing vaccinated swine from swine infected by a wild-type PRRS virus. Preferably, such isolated polynucleotide molecules further contain one or more mutations that genetically disable the encoded PRRS virus in its ability to produce PRRS, and more preferably are able to elicit an effective immunoprotective response in a porcine animal against infection by a PRRS virus.

Heterologous antigenic epitopes that are detectable, and the sequences that encode them, are known in the art. Techniques for detecting such antigenic epitopes are also known in the art and include serological detection of antibody specific to the heterologous antigenic epitope by means of, for example, Western blot, ELISA, or fluorescently labeled antibodies capable of binding to the antibodies specific to the heterologous antigenic epitope. Techniques for serological detection useful in practicing the present invention can be found in texts recognized in the art, such as Coligan, J. E., et al. (eds), 1998, *Current Protocols in Immunology*, John Willey & Sons, Inc., which is hereby incorporated by reference in its entirety. Alternatively, the heterologous antigenic epitope itself can be detected by, for example, contacting samples that potentially comprise the antigenic epitope with fluorescently-labeled antibodies or radioactively-labeled antibodies that specifically bind to the antigenic epitopes.

The present invention further provides an isolated polynucleotide molecule comprising a DNA sequence encoding an infectious RNA molecule which encodes a genetically modified North American PRRS virus that detectably lacks a North American PRRS virus antigenic epitope, wherein the DNA sequence encoding the RNA molecule encoding the North American PRRS virus is SEQ ID NO:1 or a sequence homologous thereto, except that it lacks one or more nucleotide sequences encoding a detectable North American PRRS virus antigenic epitope. Such isolated polynucleotide molecules are useful for distinguishing between swine infected with a recombinant North American PRRS virus of the present invention and swine infected with a wild-type PRRS virus. For example, animals vaccinated with killed, live or attenuated North American PRRS virus encoded by such an isolated polynucleotide molecule can be distinguished from animals infected with wild-type PRRS based on the absence of antibodies specific to the missing antigenic epitope, or based on the absence of the antigenic epitope itself: If antibodies specific to the missing antigenic epitope, or if the antigenic epitope itself, are detected in the animal, then the animal was exposed to and infected by a wild-type PRRS virus. Means for detecting antigenic epitopes and antibodies specific thereto are known in the art, as discussed above. Preferably, such an isolated polynucleotide molecule further contains one or more mutations that genetically disable the encoded PRRS virus in its ability to produce PRRS. More preferably, the encoded virus remains able to elicit an effective immunoprotective response against infection by a PRRS virus.

B. Plasmids Encoding a North American PRRS Virus or a Genetically Modified North American PRRS Virus:

The present invention also provides any of the above-described isolated polynucleotide molecules in the form of a plasmid capable of expressing the North American PRRS virus encoded thereby.

Plasmids of the present invention can express the encoded North American PRRS virus outside of a living organism, to produce North American PRRS viruses of the invention useful, inter alia, for preparing vaccines. In one embodiment, a plasmid of the present invention capable of expressing a North American PRRS virus outside of a living organism is a plasmid wherein transcription of viral RNA therefrom occurs in vitro (i.e. extracellularly); the resulting viral RNA molecule is transfected into a suitable host cell using known mechanisms of transfection, such as electroporation, lipofection (in some cases using a commercially available reagent, such as Lipofectin™ (Life Technologies Inc., Rockville, Md., USA)), or DEAE dextran mediated transfection. Other methods of transfection are known in the art and can be employed in the present invention. An example of such a plasmid for in vitro transcription of North American PRRS viral RNA is the plasmid pT7P129A (ATCC Accession No. 203488). Any promoter useful for in vitro transcription can be used in such plasmids of this invention. T7 is one such promoter, but other promoters can be used, such as an SP6 promoter or a T3 promoter. The sequences of such promoters can be artificially synthesized or cloned from commercially available plasmids. Suitable plasmids for preparing such plasmids capable of expressing North American PRRS virus include, but are not limited to, general purpose cloning vector plasmids such as pCR2.1 (Invitrogen, Carlsbad, Calif., USA), pBR322, and pUC18. A nucleotide sequence of the present invention encoding the North American PRRS virus can be inserted into any of these plasmids using known recombinant techniques. Other plasmids into which the polynucleotide molecules of the present invention can be inserted will be recognized by those of ordinary skill in the art.

Suitable conditions for in vitro transcription of viral RNA from any of the above-described recombinant plasmids comprising a DNA sequence encoding an infectious RNA molecule encoding a North American PRRS virus depends on the type of plasmid, for example, its particular promoter, and can be ascertained by one of ordinary skill in the art. For example, if a plasmid of the present invention is based on a pCR2.1 plasmid comprising a T7 promoter, then an example of suitable conditions for in vitro transcription includes reacting the plasmid with T7 RNA polymerase and ribonucleotides in a standard buffer and incubating the reaction at 37° C. for about 30 minutes. In some cases, commercial kits are available for transcribing RNA from a particular plasmid, and such kits can be used in the present invention. The reaction mixture following transcription can be directly transfected into a suitable host cell without purification, or the transcribed North American PRRS virus RNA can be purified by known RNA purification techniques, for example by organic (e.g. phenol) extraction and alcohol (e.g. ethanol or isopropanol) precipitation, prior to transfection.

Practically any mammalian or avian cell culture can be transfected with the North American PRRS virus RNA obtained as described above in order to generate a first round of North American PRRS virions. An example of cells which one might find particularly useful because of their ready availability and ease of use are BHK (baby hamster kidney) cells. However, if one wishes to generate a cell culture capable of sustained production of North American PRRS virions, then porcine alveolar macrophage cells or MARC-145 cells (Kim, H. S., et al., supra) are preferred since these cells excrete high levels of new generation PRRS virions subsequent to PRRS virus infection. Other cell lines derived from the MA-104 cell line may also be used for sustained generation of North American PRRS virions of the present invention. Primary porcine alveolar macrophage cells can be obtained by lung lavages from pigs, and the MARC-145 monkey kidney cell line can be obtained from the National Veterinary Services Laboratories otherwise known as NVSL (Ames, Iowa, USA).

In another embodiment, a plasmid capable of expressing a North American PRRS virus of the present invention outside of a living organism is a plasmid which is transfected into a suitable host cell, for example by electroporation or lipofection, transcription of the infectious RNA molecule and expression of the North American PRRS virus therefrom occurring within the transfected host cell. The transfected host cell therefore generates North American PRRS virions. Such a completely cellular method has heretofore never been disclosed or suggested for any virus within the order of Nidovirales. Because of possible cryptic splicing and termination sequences present in the RNA genome of viruses of the Nidovirales order, a completely cellular method of expressing a Nidovirales virus was believed unlikely. Cryptic sequences include RNA splice donor and splice acceptor sequences, which could cause inappropriate splicing of the RNA transcript, as well as polyadenylation sequences, which could cause premature termination by the cellular RNA polymerase II. The present invention demonstrates, however, that the presence of such sequences in a plasmid comprising a cDNA clone of a Nidovirus does not prevent the plasmid's ability to express the Nidovirus when the plasmid is directly transfected into a suitable host cell.

Accordingly, the subject invention also provides plasmids and a completely cellular method for expressing a Nidovirales virus, wherein the plasmid comprises: a) a DNA sequence encoding an infectious RNA molecule encoding the Nidovirales virus; and b) a promoter capable of transcribing said encoding sequence in a cell, wherein said promoter is in operative association with the DNA sequence encoding the infectious RNA molecule. The method comprises transfecting a suitable host cell with such a plasmid, subjecting the transfected host cell to conditions suitable for expression of gene sequences transfected therein, and collecting the expressed Nidovirales virus therefrom. An example of a plasmid suitable for completely cellular expression of North American PRRS virus outside of a living organism is the plasmid pCMV-S-P129 (ATCC Accession No. 203489). In a preferred embodiment, the promoter of such a plasmid is a CMV promoter. In a preferred embodiment, a plasmid of the invention suitable for a completely cellular method of expressing a Nidovirales virus comprises a eukaryotic promoter, such as a CMV promoter, immediately upstream and adjacent to the nucleotide sequence encoding the Nidovirales virus. In a preferred embodiment, the nucleotide sequence encoding the Nidovirales virus encodes a PRRS virus, either European or North American. Other examples of Nidovirales viruses that can be expressed by means of the above-described completely cellular method include other Arteriviruses such as, equine arteritis virus, lactate dehydrogenase-elevating virus, and simian haemorrhagic fever virus; viruses that are members of the genus Coronaviridae, such as, but not limited to, feline infectious peritinitis virus, feline enteric coronavirus, canine coronavirus, bovine coronavirus, porcine respiratory coronavirus, turkey coronavirus, porcine transmissible gastroenteritis virus, human coronavirus, murine hepatitis virus, and avian infectious bronchitis virus; and members of the genus Toroviridae, such as, but not limited to, Berne virus, Breda virus, and human torovirus. Thus, plasmids suitable for completely cellular expression comprising a nucleotide sequence encoding one of these viruses are also encompassed by the present invention.

Suitable plasmids that can be used to prepare recombinant plasmids of the present invention for completely cellular expression outside of a living organism of a Nidovirales virus, such as a PRRS virus, include virtually any plasmid useful for transfection and expression in eukaryotic cells. An examples of a plasmid suitable for preparing recombinant plasmids of the present invention for completely cellular expression of a Nidovirales virus is the plasmid pCMVbeta (Clontech, Palo Alto, Calif., USA). Other plasmids which are able to transfect and express genes in eukaryotic cells which can be used to prepare plasmids of the present invention include, but are not limited to, pcDNA3.1, pRc/RSV, and pZeoSV2 (all from Invitrogen); and pCMV-Sport3 and pSV-Sport1 (both from Life Technologies Inc.). However, almost any eukaryotic expression vector will work for the present invention. Constructs based on cosmids can also be used for completely cellular ex vivo expression of a Nidovirales virus.

Suitable host cells for the completely cellular method of the present invention for expressing PRRS virus include porcine alveolar macrophage cells and the MARC-145 cells, described above. Methods of transfecting these cells with a plasmid are basically the same as those methods for transfecting cells with viral RNA described above. Such methods include, but are not limited to, electroporation, lipofection, DEAE dextran mediated transfection, and calcium phosphate coprecipitation.

Once host cells, such as porcine alveolar macrophage cells or a MARC-145 cells, have been transfected according to the subject invention, either with viral RNA or with a plasmid comprising a nucleotide sequence encoding a virus, then the cells can be frozen at about −80° C. or below for storage for up to several years. For longer periods of time, i.e. decades, storage in liquid nitrogen is preferred. If relatively frequent use of the encoded virus is envisioned, then cells hosting the virus can also be maintained (unfrozen) in culture using known techniques, for shorter periods of time. Moreover, viral particles excreted by such cells can be stored frozen at about −80° C. or below as a source of virus. Transfection of such cell lines with the polynucleotide molecule encoding the virus can be confirmed if desired, for example, by testing exhausted medium excreted by the cell line for a PRRS virus antigen using an immunofluorescent antibody test. Antibodies which are specific for PRRS virus antigens are known in the art (see, e.g., Collins, E. J., et al., WO 93/03760 Mar. 4, 1993).

In another embodiment, a plasmid of the present invention comprising a nucleotide sequence encoding a North American PRRS virus is suitable for in vivo expression of the North American PRRS virus, i.e. expression in a living organism. Plasmids which can be used for preparing recombinant plasmids for in vivo expression of a North American PRRS virus include, but are not limited to the plasmids capable of transfecting eukaryotic cells described above, such as pCMVbeta.

Animals that can be transfected with plasmids of the present invention include mammals and birds. If the animal is other than a porcine animal, for example, a mallard duck, then the plasmid can comprise a nucleotide sequence encoding a North American PRRS virus comprising further antigenic epitopes from pathogens which are capable of pathogenically infecting the animal; in such a case, the plasmid will encode a North American PRRS virus serving as a vector for transporting epitopes into the animal. If the animal is a porcine animal, then the plasmid can usefully encode any of the North American PRRS viruses described herein, including the genetically-modified North American PRRS viruses described herein.

C. Viral Vectors Encoding a North American PRRS Virus, Including Viral Vectors Encoding Genetically Modified North American PRRS Viruses:

The present invention also provides viral vectors comprising a DNA sequence encoding an infectious RNA molecule encoding any of the North American PRRS viruses described herein, including the genetically-modified North American PRRS viruses described herein. Such viral vectors are useful for transfecting eukaryotic cells for production of PRRS viruses of the present invention outside of a living organism, or for transfecting swine, or other mammals, or avians, with the sequence encoding the North American PRRS virus, for in vivo expression of the North American PRRS virus therein.

Some examples of viruses that can be used as vectors for preparing the viral vectors of the present invention include, but are not limited to, swine viruses such as, but not limited to, swine pox virus, pseudorabies virus, or African swine fever virus. Such swine viruses can be obtained from The National Veterinary Services Laboratories (Ames, Iowa, USA) of the United States Department of Agriculture; the American Type Culture Collection, otherwise known as the ATCC (Manassas, Va., USA); and other known sources. Recombinant viral vectors based on suitable swine viruses such as the aforementioned swine viruses are useful for transfecting swine animals with a nucleotide sequence encoding a North American PRRS virus of the present invention.

Viral vectors comprising a DNA sequence encoding an infectious RNA molecule encoding a North American PRRS virus of the present invention based on these and other viruses can be prepared using known recombinant techniques described in texts such as those cited previously in this application.

D. Transfected Host cells Encoding or a Genetically Modified North American PRRS Viruses:

The present invention also provides transfected host cells that comprise a DNA sequence encoding an infectious RNA molecule encoding any of the North American PRRS viruses described herein, including the genetically-modified North American PRRS viruses described herein, which transfected host cells are capable of expressing the North American PRRS virus. Such transfected host cells are useful for producing North American PRRS viruses of the present invention. Examples of transfected host cells of the present invention include the transfected porcine alveolar macrophage cells and the transfected MARC-145 cells described above.

Other transfected host cells of the invention include, but are not limited to, transfected MA-104 cells and other derivatives of MA-104 cells that are transfected; transfected Baby Hamster Kidney (BHK) cells; transfected Chinese Hamster Ovary (CHO) cells; and African Green Monkey kidney cells other than MA-104 cells or MARC-1 45 cells, such as VERO cells; that are transfected.

E. North American PRRS Viruses, Including Genetically Modified North American PRRS Viruses:

The present invention also provides North American PRRS viruses as described herein, including genetically-modified North American PRRS viruses as described herein, expressed and/or encoded by any of the above-described isolated polynucleotide molecules, RNA molecules, plasmids, viral vectors, or transfected host cells.

In certain situations, for example where the North American PRRS virus is to be used in a vaccine for swine and the North American PRRS virus has not been genetically modified as described above so as to be unable to cause PRRS, it is desirable to treat the North American PRRS virus, for example by inactivating or attenuating it, so that it is unable to cause PRRS in swine to which it is administered. Known methods can be used to inactivate a North American PRRS virus of the present invention so that it is unable to cause PRRS in an animal. Examples of such methods include, but are not limited to, treatment with formaldehyde, BEI (binary ethyleneimine), or BPL (beta-propiolactone). Methods of attenuation are also known in the art, and such methods can be used to attenuate a North American PRRS virus of the present invention. A North American PRRS virus of the present invention can, for example, be attenuated by serial passage in cell culture.

If a North American PRRS virus of the present invention is for use in an animal other than a porcine animal, or if it has been genetically modified as described herein so that it is unable to produce PRRS in a porcine animal, then it is not necessary to treat the virus as described in the preceding paragraph prior to using it in a vaccine.

F. Vaccines and Uses Thereof:

The present invention also provides vaccines comprising North American PRRS viruses, including genetically modified North American PRRS viruses disabled in their ability to produce PRRS in a swine animal as described herein; infectious RNA molecules and plasmids encoding such North American PRRS viruses as described herein; and viral vectors encoding such North American PRRS viruses and isolated RNA molecules as described herein. The invention also provides methods for protecting animals from infection comprising vaccination with such vaccines.

In a preferred embodiment, the subject invention provides a vaccine comprising a genetically modified North American PRRS virus comprising one or more heterologous antigenic epitopes as described herein, an infectious RNA molecule encoding such a genetically modified North American PRRS virus, or a plasmid as described herein encoding such a genetically modified North American PRRS virus, in an amount effective to elicit an immunoprotective response against infection by the pathogen or pathogens from which the heterologous antigenic epitope(s) are derived, and a carrier acceptable for pharmaceutical or veterinary use.

Such vaccines can be used to protect from infection a mammal or a bird capable of being pathogenically infected by the pathogen or pathogens from which the heterologous antigenic epitope(s) are derived. Accordingly, the subject invention also provides a method for protecting a mammal or a bird from infection by a pathogen, which comprises vaccinating the mammal or bird with an amount of the vaccine described in the preceding paragraph effective to elicit an immunoprotective response in the mammal or bird from infection by the pathogen.

In a further preferred embodiment, the vaccine comprises a genetically modified North American PRRS virus, or an infectious RNA molecule or plasmid encoding such a genetically modified North American PRRS virus, comprising or encoding one or more heterologous antigenic epitopes from a swine pathogen other than a North American PRRS virus These vaccines are useful for protecting swine from infection by the swine pathogen or pathogens from which the heterologous antigenic epitope(s) are derived. If such a vaccine comprises the genetically modified North American PRRS virus, the genetic modification of the North American PRRS virus preferably preferably renders the virus unable to cause PRRS in swine. In another preferred embodiment, the genetically modified North American PRRS virus in the vaccine is able to elicit an immunoprotective response against infection by a PRRS virus, thus providing a dual-vaccine for swine, protecting swine from infection by the swine pathogen or pathogens from which the heterologous antigenic epitope(s) are derived as well as from infection by a PRRS virus. If the vaccine comprises an infectious RNA molecule or a plasmid encoding a genetically-modified North American PRRS virus comprising one or more heterologous antigenic epitopes from another swine pathogen, then the sequence encoding the infectious RNA molecule encoding the genetically modified PRRS virus preferably comprises one or more further mutations that genetically disable the encoded North American PRRS virus so that it is unable to cause PRRS. In another preferred embodiment, the encoded genetically modified, disabled North American PRRS virus is able to elicit an immunoprotective response against a PRRS infection in a swine animal, thus providing a dual-vaccine for swine, able to protect swine from infection by the swine pathogen or pathogens from which the heterologous antigenic epitope(s) are derived as well as from infection by a PRRS virus. All of these vaccines also further comprise a carrier acceptable for veterinary use.

The present invention further provides a method for protecting a porcine animal from infection by a swine pathogen or pathogens other than a North American PRRS virus and, optionally, for simultaneously protecting the swine animal from infection by a PRRS virus, which comprises vaccinating the animal with an amount of a vaccine described in the preceding paragraph effective to elicit an immunoprotective response in the swine animal from an infection by the swine pathogen or pathogens and optionally, by a PRRS virus.

Vaccines of the present invention can be formulated following accepted convention to include acceptable carriers for animals, including humans (if applicable), such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehides and additives, including those that are particularly useful in formulating modified live vaccines, are known or will be apparent to those skilled in the art. See, e.g., Remington's *Pharmaceutical Science*, 18th ed., 1990, Mack Publishing, which is incorporated herein by reference.

Vaccines of the present invention can further comprise one or more additional immunomodulatory components such as, e.g., an adjuvant or cytokine, among others. Non-limiting examples of adjuvants that can be used in the vaccine of the present invention include the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block copolymer (CytRx, Atlanta Ga.), QS-21 (Cambridge Biotech Inc., Cambridge Mass.), SAF-M (Chiron, Emeryville Calif.), AMPHIGEN® adjuvant, saponin, Quil A or other saponin fraction, monophosphoryl lipid A, and Avridine lipid-amine adjuvant. Non-limiting examples of oil-in-water emulsions useful in the vaccine of the invention include modified SEAM62 and SEAM 1/2 formulations. Modified SEAM62 is an oil-in-water emulsion containing 5% (v/v) squalene (Sigma), 1% (v/v) SPAN® 85 detergent (ICI Surfactants), 0.7% (v/v) TWEEN® 80 detergent (ICI Surfactants), 2.5% (v/v) ethanol, 200 pg/ml Quil A, 100 μg/ml cholesterol, and 0.5% (v/v) lecithin. Modified SEAM 1/2 is an oil-in-water emulsion comprising 5% (v/v) squalene, 1% (v/v) SPAN® 85 detergent, 0.7% (v/v) Tween 80 detergent, 2.5% (v/v) ethanol, 100 μg/ml Quil A, and 50 μg/ml cholesterol. Other immunomodulatory agents that can be included in the vaccine include, e.g., one or more interleukins, interferons, or other known cytokines.

Vaccines of the present invention can optionally be formulated for sustained release of the virus, infectious RNA molecule, plasmid, or viral vector of the present invention. Examples of such sustained release formulations include virus, infectious RNA molecule, plasmid, or viral vector in combination with composites of biocompatible polymers, such as, e.g., poly(lactic acid), poly(lactic-co-glycolic acid), methylcellulose, hyaluronic acid, collagen and the like. The structure, selection and use of degradable polymers in drug delivery vehicles have been reviewed in several publications, including A. Domb et al., 1992, Polymers for Advanced Technologies 3: 279–292, which is incorporated herein by reference. Additional guidance in selecting and using polymers in pharmaceutical formulations can be found in texts known in the art, for example M. Chasin and R. Langer (eds), 1990, "Biodegradable Polymers as Drug Delivery Systems" in: *Drugs and the Pharmaceutical Sciences*, Vol. 45, M. Dekker, N.Y., which is also incorporated herein by reference. Alternatively, or additionally, the virus, plasmid, or viral vector can be microencapsulated to improve administration and efficacy. Methods for microencapsulating antigens are well-known in the art, and include techniques described, e.g., in U.S. Pat. No. 3,137,631; U.S. Pat. No. 3,959,457; U.S. Pat. No. 4,205,060; U.S. Pat. No. 4,606,940; U.S. Pat. No. 4,744,933; U.S. Pat. No. 5,132,117; and International Patent Publication WO 95/28227, all of which are incorporated herein by reference.

Liposomes can also be used to provide for the sustained release of virus, plasmid, or viral vector. Details concerning how to make and use liposomal formulations can be found in, among other places, U.S. Pat. No. 4,016,100; U.S. Pat. No. 4,452,747; U.S. Pat. No. 4,921,706; U.S. Pat. No. 4,927,637; U.S. Pat. No. 4,944,948; U.S. Pat. No. 5,008,050; and U.S. Pat. No. 5,009,956, all of which are incorporated herein by reference.

An effective amount of any of the above-described vaccines can be determined by conventional means, starting with a low dose of virus, plasmid or viral vector, and then increasing the dosage while monitoring the effects. An effective amount may be obtained after a single administration of a vaccine or after multiple administrations of a vaccine. Known factors can be taken into consideration when determining an optimal dose per animal. These include the species, size, age and general condition of the animal, the presence of other drugs in the animal, and the like. The actual dosage is preferably chosen after consideration of the results from other animal studies.

One method of detecting whether an adequate immune response has been achieved is to determine seroconversion and antibody titer in the animal after vaccination. The timing of vaccination and the number of boosters, if any, will preferably be determined by a doctor or veterinarian based on analysis of all relevant factors, some of which are described above.

The effective dose amount of virus, infectious RNA molecule, plasmid, or viral vector, of the present invention can be determined using known techniques, taking into account factors that can be determined by one of ordinary skill in the art such as the weight of the animal to be vaccinated. The dose amount of virus of the present invention in a vaccine of the present invention preferably ranges from about $10^1$ to about $10^9$ pfu (plaque forming units), more preferably from about $10^2$ to about $10^8$ pfu, and most preferably from about $10^3$ to about $10^7$ pfu. The dose amount of a plasmid of the present invention in a vaccine of the present invention preferably ranges from about 0.1 μg to about 100 mg, more preferably from about 1μg to about 10 mg, even more preferably from about 10μg to about 1 mg. The dose amount of an infectious RNA molecule of the present invention in a vaccine of the present invention preferably ranges from about 0.1 to about 100 mg, more preferably from about 1 μg to about 10 mg, even more preferably from about 10 μg to about 1 mg. The dose amount of a viral vector of the present invention in a vaccine of the present invention preferably ranges from about $10^1$ pfu to about $10^9$ pfu, more preferably from about $10^2$ pfu to about $10^8$ pfu, and even more preferably from about $10^3$ to about $10^7$ pfu. A suitable dosage size ranges from about 0.5 ml to about 10 ml, and more preferably from about 1 ml to about 5 ml.

The present invention further provides a method of preparing a vaccine comprising a North American PRRS virus, infectious RNA molecule, plasmid, or viral vector described herein, which method comprises combining an effective amount of one of the North American PRRS virus, infectious RNA molecule, plasmid, or viral vector of the present invention, with a carrier acceptable for pharmaceutical or veterinary use.

It is to be understood that the term "North American PRRS viruses of the present invention" and like terms, unless otherwise indicated, include any of the genetically modified North American PRRS viruses described herein as well as the unmodified North American PRRS virus described herein encoded by SEQ ID NO:1 or a sequence homologous thereto.

G. Isolated Polynucleotide Molecules and Transfected Host Cells Encoding North American PRRS Virus Peptides, and Methods for Making Functional North American PRRS Virions:

The present invention also provides an isolated polynucleotide molecule comprising one or more nucleotide sequences that encode a peptide encoded by a North American PRRS virus, wherein the genome sequence of said North American PRRS virus is the same as or homologous to an RNA molecule corresponding to SEQ ID NO:1. As used herein, terms such as "North American PRRS virus peptide" mean a peptide that is expressed by a North American PRRS virus. Such a peptide can be, but is not necessarily, specific to North American PRRS viruses.

In a preferred embodiment, an isolated polynucleotide molecule of the present invention encoding a North American PRRS virus peptide comprises a sequence or sequences independently selected from SEQ ID NO:2, SEQ ID NO:3, SEQ ID NO:4, SEQ ID NO:5, SEQ ID NO:6, SEQ ID NO:7, SEQ ID NO:8, SEQ ID NO:9, and a sequence homologous to any of said sequences. Such isolated polynucleotide molecules are useful in plasmids or for preparing viral vectors for transfecting a suitable host cell to create a "helper" cell comprising one or more nucleotide sequences that encode a peptide encoded by a North American PRRS virus, wherein the genome sequence of said North American PRRS virus is the same as or homologous to an RNA sequence corresponding to SEQ ID NO:1, which helper cell is useful in the preparation of functional virions of genetically modified North American PRRS viruses of the present invention, which viruses have been genetically modified as described above so that they are missing from their RNA genome the sequence(s) encoding the peptide or peptides encoded by the helper cell.

Accordingly, the subject invention also includes plasmids and viral vectors comprising one or more nucleotide sequences encoding a peptide encoded by a North American PRRS virus, wherein the genome sequence of said North American PRRS virus is the same as or homologous to an RNA sequence corresponding to SEQ ID NO:1. Such plasmids of the invention can be based on those plasmids described above useful for preparing plasmids comprising a nucleotide sequence encoding a North American PRRS virus. Such viral vectors of the invention can be based on, for example, retrovirus vectors or adeno-associated viral vectors. These plasmids and viral vectors are useful for preparing the helper cells described in the preceding paragraph.

The present invention also thus provides a helper cell, i.e., a transfected host cell comprising one or more nucleotide sequences that encode a peptide encoded by a North American PRRS virus, wherein the genome sequence of said North American PRRS virus is the same as or homologous to an RNA sequence corresponding to SEQ ID NO:1. In preferred embodiments, the transfected host cell comprises a nucleotide sequence or sequences independently selected from SEQ ID NO:2, SEQ ID NO:3, SEQ ID NO:4, SEQ ID NO:5, SEQ ID NO:6, SEQ ID NO:7, SEQ ID NO:8, SEQ ID NO:9 and a sequence homologous to any of said sequences. These helper cells are useful as described above for providing peptides for completing infectious RNA molecules deficient in sequences encoding the peptide(s) encoded by the helper cell so that functional virions of a genetically modified North American PRRS virus can be generated by the cell.

Suitable cells for this aspect of the invention include the cells described above which are suitable for expressing North American PRRS viruses, such as the porcine alveolar macrophage cells and the MARC-145 cells. However, practically any mammalian or avian cell can be used. As discussed above, if one wishes to obtain a transfected host cell capable of reinfection by PRRS virions, and thus able to generate multiple generations of functional genetically modified North American PRRS virions, porcine alveolar macrophage cells and MARC-145 cells are preferred.

The subject invention thus further provides a method for generating a functional virion of a genetically modified North American PRRS virus encoded by an RNA sequence corresponding to SEQ ID NO:1 or a sequence homologous thereto comprising one or more mutations that disable one or more peptide coding sequences, which method comprises transfecting a helper cell as described in the preceding paragraph with an infectious RNA molecule, plasmid, or viral vector encoding the genetically modified North American PRRS virus, which helper cell comprises a nucleotide sequence or sequences encoding the North American PRRS virus peptide or peptides of the disabled peptide coding sequence(s) of the genetically modified North American PRRS virus.

The subject invention further provides a method for generating a functional virion of a genetically modified North American PRRS virus encoded by an RNA sequence corresponding to SEQ ID NO:1 or a sequence homologous thereto comprising one or more mutations in one or more peptide coding sequences, which method comprises transfecting a suitable cell with both an infectious RNA molecule, plasmid, or viral vector encoding the genetically modified North American PRRS virus and a helper virus that expresses in the cell the North American PRRS virus peptide or peptides of the mutated peptide coding sequence or sequences of the modified North American PRRS virus, and separating genetically modified North American PRRS virions from the helper virus. Methods of separation are known in the art and include use of conditional lethal helper viruses that distinguish (kill) the helper virus under certain conditions wherein the expressed North American PRRS virus is not killed. Other known methods of separation include physical methods of separation subsequent to expression of both helper virions and North American PRRS virions, for example by density gradient centrifugation. Suitable cells for this method of the invention include the cells capable of infection by a PRRS virus, such as porcine alveolar macrophage cells and MARC-145 cells. Other cells which are able to be infected by a PRRS virus are described previously in this application, for example the MA-104 cell line or other cell lines derived from the MA-104 cell line. An example of a helper virus is a PRRS virus, preferably a North American PRRS virus isolate, such as P129. Any virus, either wild-type, isolated, or recombinant, that expresses PRRS peptides can be used as a helper virus.

Infectious RNA molecules, plasmids, and viral vectors that encode a genetically modified North American PRRS virus useful in either of the above methods for generating a functional virion of a genetically modified North American PRRS virus are those infectious RNA molecules, plasmids, and viral vectors described in this application.

H. Immunoprotective Genetically Modified Nidovirales Viruses and Vaccines Comprising Them:

The subject invention further provides a genetically modified Nidovirales virus that is capable of eliciting an immunoprotective response in a mammal or a bird vaccinated therewith, which genetically modified Nidovirales virus is prepared by obtaining an isolated polynucleotide molecule comprising a DNA sequence encoding an infectious RNA molecule encoding a wild-type Nidovirales virus, genetically mutating the DNA sequence encoding the infectious RNA molecule encoding the wild-type Nidovirales virus so as to obtain an isolated polynucleotide molecule comprising a DNA sequence encoding an infectious RNA molecule encoding a genetically modified Nidovirales virus which virus is able to elicit an effective immunoprotective response against infection by the wild-type Nidovirales virus in a mammal or a bird, and expressing the genetically modified Nidovirales virus from the isolated polynucleotide molecule so obtained.

The subject invention further provides a method for preparing a genetically modified Nidovirales virus that is capable of eliciting an immunoprotective response in a mammal or a bird vaccinated therewith, which method comprises obtaining an isolated polynucleotide molecule comprising a DNA sequence encoding an infectious RNA molecule encoding a wild-type Nidovirales virus, genetically mutating the DNA sequence encoding the infectious RNA molecule encoding the wild-type Nidovirales virus so as to obtain an isolated polynucleotide molecule comprising a DNA sequence encoding an infectious RNA molecule encoding a genetically modified Nidovirales virus which virus is able to elicit an effective immunoprotective response against infection by the wild-type Nidovirales virus in a mammal or a bird, and expressing the genetically modified Nidovirales virus from the isolated polynucleotide molecule so obtained.

DNA sequences encoding infectious RNA molecule encoding a Nidovirales virus include the DNA sequences which are the same as or homologous to SEQ ID NO:1 described herein, which encode a North American PRRS virus. DNA sequences encoding infectious RNA molecules encoding Nidovirales viruses other than a North American PRRS virus are known in the art and can be obtained from known sources, for example the genetic databases cited above. Other examples of some DNA sequences encoding infectious RNA molecules encoding Nidovirales viruses which can be used in the subject invention include the DNA sequence encoding European PRRS virus described in Meulenberg, J. J. M. et al., 1993, supra; the DNA sequence encoding equine arteritis virus described in van Dinten, L. D., et al., 1997, Proc. Natl. Acad. Sci. USA, 94(3):991–6; and the DNA sequence encoding equine arteritis virus described in den Boon, J. A., et al., 1991, J. Virol. 65(6):2910–20, all of which references are hereby incorporated in their entireties into the present application. Nidovirales viruses which can be genetically modified by means of the present invention can be any Nidovirales virus for which a coding DNA sequence is obtained. Some examples of Nidovirales viruses are described in previous sections of the present application.

Once a DNA sequence encoding an infectious RNA molecule encoding a Nidovirales virus is obtained, isolated polynucleotide molecules, for example plasmids, comprising the DNA sequence encoding an infectious RNA molecule encoding a Nidovirales virus can be synthesized using recombinant techniques described above.

The sequences encoding the infectious RNA molecule encoding a Nidovirales virus can be genetically mutated as described above for the North American PRRS virus so as to obtain Nidovirales viruses comprising genetic modifications such as an inability to cause disease in an animal infected therewith, inclusion of heterologous antigenic epitopes that are able to elicit an immunoprotective response in an animal, inclusion of heterologous antigenic epitopes that are detectable, and deletion of detectable antigenic epitopes. Such genetic modifications are described above. Genetic mutations so as to encode genetically modified Nidovirales viruses can occur in coding and/or noncoding regions of the DNA sequence encoding the infectious RNA molecule encoding the Nidovirales virus. In one embodiment, one or more genetic mutations occur in an ORF encoding a viral peptide of the Nidovirales virus.

"Wild-type Nidovirales virus", as used herein, means a Nidovirales virus whose genome has not intentionally been genetically mutated, such as a Nidovirales virus occurring in nature and isolates thereof.

The subject invention further provides a vaccine for protecting a mammal or a bird from infection by a Nidovirales virus, which comprises a genetically modified Nidovirales virus as described above in an amount effective to elicit an effective immunoprotective response against the wild-type Nidovirales virus in a mammal or a bird vaccinated therewith, and a carrier acceptable for pharmaceutical or veterinary use. These vaccines of the present invention can be formulated using the techniques for formulating vaccines described above.

The following examples are provided to merely illustrate aspects of the subject invention. They are not intended, and should not be construed, to limit the invention set forth in the claims and more fully described herein.

EXAMPLES

Example I

Preparation of an Infectious cDNA Clone of a North American PRRS Virus Isolate.

Source of PRRS virus and MARC-145 cells: A North American PRRS virus isolate designated P129 was obtained from Drs. Gregory W. Stevenson, William G. Van Alstine, and Charles L. Kanitz of Purdue University's Animal Disease Diagnostic Laboratory in West Lafayette, Ind. The P129 virus was originally isolated in the autumn of 1995 from a swine herd in southern Indiana experiencing a severe PRRS outbreak. This farm had no previous history of PRRS problems or PRRS vaccination. The P129 isolate was more virulent than several other field isolates from the same time period and geographic area, in that it produced more severe and more consistent respiratory disease in young pigs. The virus was initially isolated on primary porcine alveolar macrophage (the natural host cell), and subsequently passaged on MARC-145 cells (Kim, H. S. et al., 1993, Arch. Virol. 133:477483). Genes encoding structural proteins of P129 were found to be homologous to corresponding known North American PRRS gene sequences.

The MARC-145 cell line that was used to propagate PRRS viruses is a clone of the MA-104 Rhesus Macaque Monkey Kidney cell line. The MARC-145 cells were obtained from the National Veterinary Services Laboratories (NVSL, Ames, Iowa) of the USDA. These cells have been tested and found negative for mycoplasmas and for common porcine extraneous agents. MARC-145 cells are routinely grown at 37C in OptiMEM (Life Technologies Inc.) with 2% fetal bovine serum and antibiotics.

Five biological clones were plaque purified from the P129 virus stock, and these were designated P129A through P129E. Plaque purification was carried out by infecting monolayers of MARC-145 cells with P129 virus, adding an overlay of OptiMEM containing 1.25% SeaPlaque agarose (FMC BioProducts), 2% fetal bovine serum, and antibiotics. Plaques were clearly visible following incubation for 7 days, when 5 well-isolated plaques were picked and passaged onto fresh MARC-145 monolayers. When cytopathic effect (virus induced cell death) became apparent the progeny virus from each of these cultures was subjected to another round of plaque purification. One well-isolated plaque from each of the five clones was picked and expanded to produce large stocks. The 5 clones were tested for virulence in young pigs, either individually (clones A and E) or in combination (clones B–D, or clones A–E). In all cases, the plaque purified virus replicated well in pigs and caused clinical disease. The severity of clinical symptoms was less than that caused by the uncloned P129 virus, even when all five clones were used together. P129A was chosen for sequencing, and was used in subsequent molecular manipulations.

Determination of the genome sequence of P129A: Plaque purified virus P129A was used for sequence determination after 10 serial passages from the pig (including two plaque purifications and one subsequent passage). SEQ ID NO:1 shows the cDNA sequence corresponding to the P129A RNA genome. The genome is 15,395 nucleotides in length (excluding the polyadenosine tail), begins with ATGACGTA, and ends with CCGCAATT. A typical polyadenosine tail of 55 residues is also provided in SEQ ID NO:1.

For the structural genes of P129A (ORFs 2 through 7), which comprise the 3' 20% of the genome, various PCR primers were chosen based on several partial cDNA sequences of other North American PRRS virus isolates available in the public DNA sequence database GenBank (for example PRU00153). Purified viral RNA was reverse transcribed into cDNA using reverse transcriptase and random hexamer primers. This cDNA was then used in PCR with gene-specific primers. PCR products were excised from gels and T/A cloned into plasmid pCR2.1 (Invitrogen). For each primer pair, multiple plasmids (from independent PCR reactions) were DNA sequenced. Sequences were assembled using the Seqman program from the Lasergene package (DNASTAR, Inc). This permitted completing the sequence of positions 11,992 through 15,347 of the P129A genome.

Also in the GenBank database are a series of short sequences (approximately 218 nucleotides total) which comprise a portion of the ORF 1b gene of several isolates of PRRS virus. One of these (PPSSEQB) was used to design PCR primers (forward 5'-ACAGTTTGGTGATCTATG-3' (SEQ ID NO:10), corresponding to positions 9063–9080; reverse 5'-CAGATTCAGATGTTCAA-3' (SEQ ID NO:11), corresponding to positions 9252–9268). These amplified a 206 nucleotide fragments, which includes 171 nucleotides of new sequence from the P129A ORF1b gene, corresponds to positions 9081 to 9251. A new forward primer was designed within this region (5'-ACCTCGTGCTGTATGCCGAATCTC-3' (SEQ ID NO:12), positions 9201–9224), and a matching primer was designed within ORF1b immediately upstream of ORF2 (5'-TCAGGCCTAAAGTTGGTTCAATGA-3' (SEQ ID NO:13), positions 12,027–12,050). These primers were used in RT-PCR to amplify a 2850 nucleotide fragment of ORF1b, corresponding to positions 9201–12,050 of the P129A genome.

During RT-PCR amplification of ORF5 of another North American field isolate of PRRS virus, a minor band was seen which was smaller than the expected size. This was sequenced and found to have limited homology with ORF1a of Lelystad virus (resulting from false priming). New primers within this region were chosen to amplify P129A (forward 5'-GATGACTGGGCTACTGACGAGGAT-3' (SEQ ID NO:14), corresponding to positions 1587–1610; reverse 5'-AGAGCGGCTGGGATGACACTG-3' (SEQ ID NO:15), corresponding to positions 1877–1897). In addition to the product of 311 nucleotides (266 nucleotides of new P129A sequence between the primers corresponding to positions 1611–1876), a larger minor PCR product of 701 nucleotides was cloned and sequenced (656 nucleotides of new P129A sequence between the primers corresponding to positions 1611–2264). The larger band results from false priming of the reverse primer at positions 2265–2269.

The extreme 5' end of the genome of P129A was determined by 5' RACE (rapid amplification of cDNA ends) using a commercially available kit (Life Technologies Inc). Two nested reverse primers were chosen from within the known ORF1a sequence ("RACE2" 5'-CCGGGGAAGCCAGACGATTGAA-3' (SEQ ID NO:16), positions 1917–1938; and "RACE3" 5'-AGGGGGAGCAAAGAAGGGGTCATC-3' (SEQ ID NO:17), positions 1733–1756). RACE2 was used to prime cDNA synthesis, while RACE3 was used in PCR. The resulting PCR products were cloned and sequenced. The two longest products ended at precisely the same base (position 1 in SEQ ID NO:1).

The large gap between known sequence in ORF1a and ORF1b was bridged using long RT-PCR. Two new primers were used (forward 5'-AGCACGCTCTGGTGCAACTG-3' (SEQ ID NO:18), positions 1361–1380; reverse 5'-GCCGCGGCGTAGTATTCAG-3' (SEQ ID NO:19), positions 9420–9438). The resulting 8078 nucleotide RT-PCR product was cloned and sequenced.

The extreme 3' end of the genome of P129A was determined by ligating the 3' and 5' ends of the viral RNA together and using RT-PCR to amplify the junction fragment. The resulting junction fragments were cloned and sequenced. Briefly, RNA extracted from pelleted virions was treated with tobacco acid pyrophosphatase (to remove 5' cap structures), then self-ligated with T4 RNA ligase (both from Epicentre Technologies). The primers used were 5'-CGCGTCACAGCATCACCCTCAG-3' (SEQ ID NO:20) (forward, positions 15,218–15,239) and either 5'-CGGTAGGTTGGTTAACACATGAGTT-3' (SEQ ID NO:21) (reverse, positions 656–680) or 5'-TGGCTCTTCGGGCCTATAAAATA-3' (SEQ ID NO:22) (reverse, positions 337–359). All of the resulting clones were truncated at the 5' end of the genome (the most complete came to within 57 nucleotides of the actual 5' end, as revealed by 5' RACE), however two of these clones contained the complete 3' end of the genome including the polyadenosine tail (42 and 55 adenosine residues in length). This completed the sequencing of the cDNA 15,450 base genome of PRRS isolate P129A, including polyA tail, as shown in SEQ ID NO:1.

Creation of an infectious full-length cDNA clone of P129A: A full-length infectious cDNA clone of P129A, designated pT7P129A, was assembled from four overlapping cloned RT-PCR products. The four RT-PCR products were first T/A cloned into plasmid pCR2.1 (Invitrogen) and transfected into *Escherichia coli* strain DH5-alpha. Bacterial colonies were screened, and those which contained inserts of the expected sizes in the "T7 to M13" orientation were chosen for sequencing and further manipulation. All four cloned RT-PCR products contained one or more non-silent mutations (deviations from the consensus nucleotide sequence for P129A of SEQ ID NO:1 which would result in a change in amino acid sequence of the encoded ORFs). These non-silent mutations (save one at position 12,622 in ORF 2) were repaired by subcloning fragments from other cloned RT-PCR products. The four repaired subgenomic clones were assembled into a full-length clone in a stepwise manner, using available restriction sites (see FIG. 1). The 5' and 3' ends of the cDNA corresponding to the P129A genome in pT7P129A were modified by the addition of a T7 promoter and appropriate restriction endonuclease sites. The construction of pT7P129A is described in further detail in the following paragraphs:

The 5' end of the genome (positions 1–1756), generated by 5'-RACE and cloned into pCR2.1 as described above, was modified to include a T7 promoter immediately upstream of the cDNA corresponding to the P129A genome and a PacI site for future cloning. A 3-way ligation was performed using the 1216 bp DsaI-BseRI fragment of this plasmid (containing bases 27–1242 of P129A), the 4407 bp BseRI-XbaI fragment of the same plasmid (containing bases 1243–1756 of P129A and the entire plasmid vector up to the XbaI site), and the following synthetic double-stranded adapter (SEQ ID NOS:23 and 24):

```
5'-CTAGATTAATTAATACGACTCACTATAGGGATGACGTATAGGTGTTGGCTCTATGC-3'
  3'-TAATTAATTATGCTGAGTGATATCCCTACTGCATATCCACAACCGAGATACGGTGC-5'
  XbaI ________  T7 promoter    ____________________________DsaI
       PacI                     P129A genome
```

The predicted transcript from the T7 promoter includes a single "G" residue from the promoter immediately upstream of the first "A" of the viral genome. A non-silent mutation at position 1230 (A to G) was repaired by replacing the 906 bp AatII-SacI fragment (bases 740–1645) with the same fragment from another clone. This plasmid was designated "pT7R3A-2".

The 8078 nucleotide PCR product described above was used to cover bases 1361–9438 of the P129A genome. A 58 bp deletion (positions 2535–2592) and 7 non-silent point mutations were corrected by subcloning fragments from other cloned RT-PCR products, yielding plasmid "pGAP10B-4". The 7837 bp Bsu36I-SpeI fragment from this plasmid was ligated to the 5482 bp Bsu36I-SpeI fragment from pT7R3A-2. The resulting plasmid "pT7RG" contains the first 9438 bases of the P129A genome behind the T7 promoter.

The 2850 nucleotide fragment of ORF1b described above (genome positions 9201–12,050) was corrected to repair non-silent mutations and designated "p1B3A-2". The 2682 bp NdeI-SpeI fragment of this plasmid was ligated to the 13,249 bp NdeI-SpeI fragment of pT7RG to yield plasmid "pT71A1B", which contains the first 12,050 bases of the P129A genome.

The fourth and final fragment of the P129A genome was derived by RT-PCR of ORFs 2 through 7, including the 3' non-translated region and a portion of the polyA tail. The forward primer was 5'-ACTCAGTCTAAGTGCTGGAAAGTTATG-3' (SEQ ID NO:25) (positions 11,504–11,530) and the reverse primer was 5'-GGGATTTAAATATGCATTTTTTTTTTTTTTTTTTTTTAATTGCGGCCGCATGGTTCTCG-3' (SEQ ID NO:26). The reverse primer contains the last 22 bases of the P129A genome (positions 15,374–15,395), a polyA tail of 21 bases, an NsiI site (ATGCAT) and a SwaI site (ATTTAAAT). Non-silent point mutations and a single base deletion were repaired by subcloning fragments from other clones. An additional non-silent point mutation at position 12,622 (A to G) was inadvertently introduced at this stage. This results in a change from glutamine to arginine near the C-terminus of the ORF2 protein (amino acid residue 189 of the 256 amino acids in ORF2, which does not affect the overlapping ORF 3). This mutation had no apparent influence on viral growth, in cell culture or in pigs, and was not repaired. This mutation served as a genetic marker to distinguish virus derived from the cDNA clone from possible contamination with parental P129A or other PRRS viruses. The plasmid was designated "p2_7D-4". The structural genes of P129A were added to the rest of the genome by ligating the 3678 bp Eco47III-SpeI fragment of p2_7D-4 to the 15,635 bp Eco47III-SpeI fragment of pT71A1B.

This yields the final construct "pT7P129A", which comprises cDNA corresponding almost identically to the entire genome of P129A (however, with only a 21 base polyA tail, as opposed to 55 base polyA tail) behind a T7 promoter, cloned into the pCR2.1 vector between unique restriction enzyme sites (PacI and SwaI). The total length of pTP7129A is 19,313 bp, and it is stable in *E. coli* strain DH5-alpha. pT7P129A contains an A to G non-silent point mutation at position 12,622 that results in an arginine at position 189 of ORF2 rather than a glutamine (as is encoded by SEQ ID NO:1) and a silent C to T mutation at positionl559. Neither of these mutations affected viral growth under the conditions examined, both in cell culture and in pigs. For example, pT7P129A was used for in vitro transcription and the resulting RNA transcripts produced live North American PRRS virus when transfected into MARC-145 cells, thus demonstrating that this full-length clone is infectious.

In vitro transcription and transfection of RNA transcripts: In plasmid pT7P129A there are two T7 promoters in tandem upstream of the viral genome. One of these is positioned immediately upstream of the viral genome and was built into the PCR primer as described above. The other is present in the pCR2.1 cloning vector and is located outside of the multiple cloning site (initiating transcription 44 bases upstream of the viral genome). PacI was used to cut between these T7 promoters prior to in vitro transcription to generate a transcript that is closer to authentic viral RNA (a single extra G immediately upstream the viral genome, as opposed to 44 extra bases from the distal T7 promoter). In addition, pT7P129A was cut with SwaI prior to in vitro transcription.

The resulting run-off transcripts include a 21 base long polyA tail and nine non-PRRS nucleotides, including an NsiI site (which was not used to linearize the plasmid, since the site also occurs once in the viral genome). The digested plasmid was purified by phenol extraction and ethanol precipitation prior to use.

A commercial kit (T7 Cap-Scribe, Boehringer Mannheim) was used for in vitro transcription. The DNA pellet from above, containing about 0.6 μg of PacI/SwaI digested pT7P129A, was resuspended in 20 μl of T7 Cap-Scribe buffer/T7 polymerase and incubated at 37° C. for 30 minutes. A portion of the reaction was analyzed by agarose gel electrophoresis and shown to contain full-length RNA transcripts in addition to the expected DNA bands of 15,445 bp and 3868 bp. The in vitro transcription reaction was used fresh, immediately following incubation, without purification. Freshly confluent monolayers of MARC-145 cells were washed once in OptiMEM (without serum), and covered with 1 ml per 35mm well of OptiMEM (without serum) containing 500 μg/ml DEAE dextran (molecular weight approx. 500,000, Pharmacia Biotech). In vitro transcription reaction (15 μl) was added immediately. After 1 hour at 37° C., the transfection mixture was removed, monolayers were washed once with PBS and overlaid with 1.25% SeaPlaque agarose (FMC corporation) in OptiMEM with 2% fetal bovine serum and antibiotics. After 5 days at 37° C., a single plaque was visible. This virus was designated "rP129A-1" and was expanded on MARC-145 cells and characterized in cell culture and in pigs. Subsequent transfections of in vitro transcribed RNA from pT7P129A, using both DEAE dextran and electroporation, have yielded many additional plaques.

Characterization of recombinant virus rP129A-1: There are no apparent differences in growth kinetics, yield, or plaque morphology between cDNA-derived recombinant virus rP129A-1 and its non-recombinant parent P129A. As discussed above, there are two differences in nucleotide sequence between the coding sequence of pT7P129A and the consensus sequence of P129A (shown in SEQ ID NO:1). Firstly, at position 1559 pT7P129A contains a T, whereas P129A contains a C (this is a silent mutation). Secondly, at position 12,622 pT7P129A contains a G, whereas P129A contains an A (this is the glutamine to arginine change in ORF2 described above). In order to rule out the possibility that rP129A-1 is actually a non-recombinant PRRS virus contaminant, RT-PCR and sequencing were performed on the regions surrounding these two differences. In the case of both genetic markers, rP129A-1 was identical to plasmid pT7P129A and different from parental virus P129A, thus confirming that rP129A-1 is derived from the infectious cDNA clone.

Figure 2:
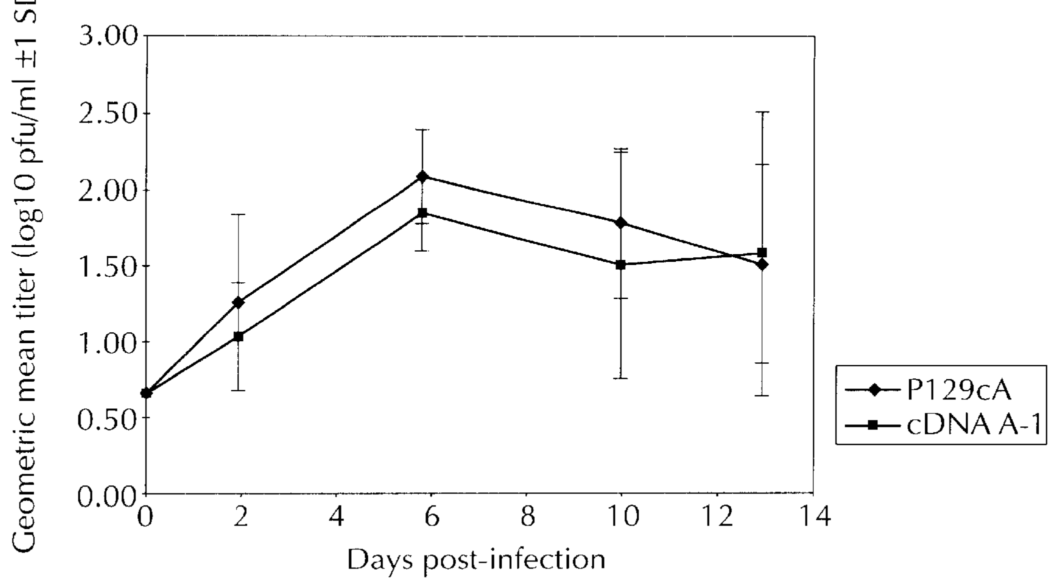
FIG. 2: Serum viremia following infection with P129A or recombinant PRRS virus rP129A-1. Determined by plaque assay on MARC-145 cells. The lower limit of detection is 5 pfu/ml (or 0.7 on the log scale).
Figure 3:
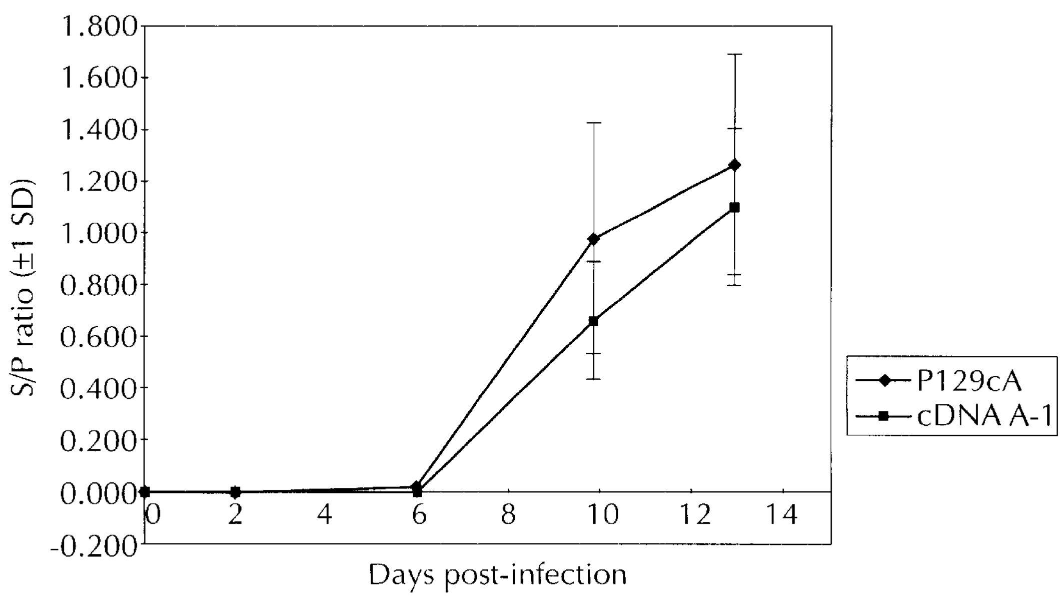
FIG. 3: Anti-PRRS virus serum antibody following infection with P129A or recombinant PRRS virus rP129A-1.

Characterization of recombinant virus rP129A-1 in pigs: The cDNA-derived virus rP129A-1 was compared to its non-recombinant parent P129A for its ability to infect and cause clinical disease in young pigs. Three groups of 10 pigs each from a PRRS-negative herd were infected at 4 weeks of age with either P129A, rP129A-1, or mock-infected with cell culture medium. Clinical signs, rectal temperatures, and body weights were monitored. Blood was collected on days 0, 2, 6, 10, and 13 post-infection for determination of serum viremia (by plaque assay on MARC-145 cells, FIG. 2) and serum antibody (by ELISA using HerdChek PRRS from IDEXX, FIG. 3). Gross and microscopic lesions of the lung were observed upon necropsy. There were no significant differences between the two virus-infected groups, indicating that rP129A-1 replicates in pigs and causes clinical disease which is quantitatively and qualitatively similar to its non-recombinant parent virus.

Example II

Deletion of ORF7 (Nucleocapsid Gene) from the North American PRRS Virus; Preparation of a Negatively-Marked, Replication-Defective Vaccine Thereby The viral nucleocapsid gene (ORF7) was partially deleted from an infectious cDNA clone of the PRRS virus of the present invention. The resulting recombinant modified PRRS virus would be expected to be replication-defective in pigs. This recombinant modified PRRS virus could be used as a vaccine to induce an immune response to the other PRRS virus proteins without the risks of clinical disease, spread to non-vaccinated animals, or reversion to virulence associated with attenuated live vaccines. In addition to being very safe, such a vaccine virus would also be "negatively marked", in the sense that it would allow exposure to field isolates of PRRS virus to be determined serologically, even in the presence of antibody to the vaccine virus. Antibodies to the ORF7 protein are commonly found in the sera of PRRS virus-infected pigs, whereas pigs vaccinated with an ORF7-deleted PRRSV would lack antibodies to the ORF7 protein.

Deletion of ORF7 from an infectious clone was accomplished as follows: Plasmid p2_7D-4 (see FIG. 1) was used as template in PCR to amplify the 5' and 3' flanking regions upstream and downstream of ORF7. The upstream flank forward primer 5'-ATTAGATCTTGCCACCATGGTGGGGAAATGCTTGAC-3' (SEQ ID NO:27) (which binds to genome positions 13,776–13,791 near the beginning of ORF5 and contains additional restriction sites which are irrelevant to the current cloning) and the upstream flank reverse primer 5'-CTTTACGCGTTTGCTTAAGTTATTTGGCGTATTTGACAAGGTTTAC-3' (SEQ ID NO:28) (which binds to genome positions 14,857–14,902 at the junction of ORFs 6 and 7) amplified a fragment of 1147 bp. The reverse primer introduced MluI and AflII sites and a single base change at position 14,874, destroying the ATG start codon for ORF7 without altering the tyrosine encoded in the overlapping ORF6. For the downstream flank, the forward primer 5'-CAACACGCGTCAGCAAAAGAAAAAGAAGGGG-3' (SEQ ID NO:29) (positions 14,884–14,914 near the 5' end of ORF7, introduced an MluI site) and reverse primer 5'-GCGCGTTGGCCGATTCATTA-3' (SEQ ID NO:30) (downstream of the viral genome in the pCR2.1 plasmid) amplified a 462 bp fragment. A 3-way ligation was performed, using the 611 bp BstEII-MluI fragment of the upstream flank PCR product, the 575 bp MluI-SpeI fragment of the downstream flank PCR product, and the 6653 bp BstEII-SpeI fragment from plasmid p2_7D-4 (all fragments were gel purified following digestion). The resulting plasmid p2_7Ddelta7+7023 was deleted in the first seven amino acids of ORF7, and lacks a functional ATG start codon. Two new restriction sites which are absent in both the viral genome and the plasmid backbone, AflII and MluI, have been inserted to facilitate directional cloning of foreign genes into the space previously occupied by the 5' end of ORF7.

The changes made in p2_7Ddelta7+7023 were incorporated into a full-length genomic clone by ligating the 3683 bp Eco47III-SpeI fragment of p2_7Ddelta7+7023 with the 15,214 bp Eco47III-SpeI fragment of pCMV-S-p129. The resulting plasmid pCMV-S-p129delta7+7023 was used to transfect cells.

Since nucleocapsid is essential for viral growth, it is necessary to provide this protein in order to allow generation and replication of an ORF7-deficient PRRS virus. This can be accomplished using a helper virus or a complementing cell line, for example. ORF7-expressing MARC-145 cell lines could be created by stably transfecting cells with a plasmid containing both the ORF7 gene from P129A and the neomycin resistance gene. After selecting for neomycin resistance using the antibiotic G418, single-cell colonies could then be expanded and characterized. Clonal MARC-145-derived cell lines that are positive for ORF7 expression by both immunofluorescence and RT-PCR could be transfected with RNA from pT7P129delta7 in order to generate ORF7-deficient P129 virus.

Similar strategies can be used to generate PRRS viruses deficient in other structural genes (ORFs 2, 3, 4, 5, or 6), or deficient in all or portions of non-structural genes 1a and 1b. In addition, multiple deletions can be engineered into a single PRRS virus, and these can be grown in complementing cells which provide all necessary functions. Such gene-deficient PRRS viruses are likely to be either partially or completely attenuated in pigs, making them useful as vaccines against PRRS. They can also be used to distinguish vaccinated animals from animals infected with a wild-type PRRS virus as discussed above and/or as vectors for vaccinating animals with epitopes of other porcine pathogens (see Example III, below).

Example III

Insertion of Heterologous Genes into the North American PRRS Virus Genome; use of PRRS Virus as a Vector, and a Positively-Marked North American PRRS Virus In Example II, above, AflII and MluI restriction enzyme sites were inserted into the region formerly occupied by the 5' end of ORF7. These sites are absent in the P129A genome and in the pCR2.1 and pCMV plasmids, and can be used in the directional cloning of foreign (heterologous) genes into the viral genome for expression. Potential leader-junction sites for transcription of the ORF7 subgenomic RNA at positions 14,744–14,749 (ATAACC) and 14,858–14,863 (TAMCC) are not affected by deletion of the ORF7 coding sequence, and can function in transcription of a foreign gene. Foreign (heterologous) genes can include genes from other PRRS virus isolates or genotypes, and/or genes from other non-PRRS pathogens, either pathogens that infect swine or pathogens that infect mammals other than swine, or avians.

In addition, these foreign genes (or portions thereof) can provide antigenic epitopes which are not normally found in swine. Such epitopes can be used to "positively mark" a vaccine, so that successful vaccination can be monitored serologically, even in the presence of antibody to field or conventional vaccine strains of PRRS virus. A positive marker needs not be a separate expression cassette. An antigenic epitope can be fused to a structural gene of the PRRS virus. For example, the upstream flank reverse primer described in Example I, above, can be extended in such a way as to add a carboxyl-terminal fusion of a non-PRRS virus antigenic epitope to the ORF6 membrane protein. The presence of antibody to this epitope in swine indicates successful vaccination.

Example IV

Cellular Expression of a PRRS Virus by Direct Transfection of cDNA into Cells The eukaryotic expression vector pCMV-MC1 (SEQ ID NO:31) was derived from the commercially available plasmid pCMVbeta (Clontech) by replacing the LacZ coding sequence between two Not I sites with a linker containing Not I, EcoR V, Avr II, Bgl II, Cla I, Kpn I, Pac I, Nhe I, Swa I, Sma I, Spe I and Not I sites. Modification of the human CMV immediate early promoter was accomplished by substituting the sequence between the Sac I and the second Not I sites of pCMV-MC1 with a synthetic linker (shown below). The linker contains a half site for Sac I following by Pac I, Spe I and a half site for Not I. After annealing the two single stranded oligonucletides, the linker was cloned into pCMV-MC1 between the Sac I and Not I sites, and a selected clone was designated pCMV-S1. The Spe I site of pCMV-S1 could not be cut, possibly due to a mistake in the oligo sequence. Therefore, the fragment between Pac I and Hind III in pCMV-S1 was replaced with Pac I (at position 877)-Hind IIII (at position 1162) fragment from pCMV-MC1. Thus, a Spe I site was regained. This final construct (pCMV-S) was used to clone the full length P129 genome.

Linker sequence (SEQ ID NOS:32 and 33):

```
     5' CGTTAATTAAACCGACTAGTGC  3'
  3' TCGAGCAATTAATTTGGCTGATCACGCCGG  5'
     _____     PacI        SpeI_______
     SacI                         NotI
```

The sequence immediately upstream of the 5' end of the P129 genome was modified to contain proper spacing and a convenient restriction enzyme site (Pac I). This was done by designing appropriate PCR primers (SEQ ID NOS:34 and 35) for amplification from pT7P129. After digestion with Pac I and Aat II, this PCR fragment was subcloned into the Pac I and Aat II sites of pT7RG (FIG. 1). The resulting plasmid was designated pT7RG-deltaT7.

The final construction was completed by subcloning the viral sequences from pT7RG-deltaT7 at the Pac I and Nde I sites into pT7P129, creating pT7P129-deltaT7. The full length P129 genome was digested from pT7P129-deltaT7 at Pac I and Spe I and transferred into pCMV-S at the Pac I and Spe I sites. This constructed was named pCMV-S-P129.

The sequence of the region of modification between the CMV promoter TATA box and the 5' end of the P129 sequence in pCMV-S-P129 is shown in SEQ ID NO:36 and schematically presented below:

```
     TATATAAGCAGAGCTCGTTAATTAAACCGTCATGACGTATAGGTGTTGGC
5'   TATA box   Sac I  Pac I          Start  of  P129      3'
```

To test the use of the CMV promoter to initiate PRRS virus infection in cells, pCMV-S-P129 plasmid DNA (0.5 or 1.0 μg) was transfected into MARC-145 cells by lipofection using Lipofectamine™ (Life Technologies Inc.). PRRS virus specific cytopathic effect was observed after transfection and the presence of PRRS virus antigen was determined by the immunofluorescent antibody test.

PRRS virus was generated efficiently from pCMV-S-P129, and the progeny virus could be passaged on MARC-145 cells. This demonstrates that a PRRS virus infection can be initiated directly from a plasmid cDNA encoding a PRRS virus, without an in vitro transcription step. Furthermore, pCMV-S-P129 generated a greater amount of progeny virus compared to plasmids wherein the 3' end of the pCMV promoter was not immediately in front of the start of the sequence encoding the North American PRRS virus.

Example V

Deletion of ORF4 from the North American PRRS Virus; Preparation of a Replication-Defective Vaccine Thereby A portion of the gene for ORF4, which encodes a membrane glycoprotein, was deleted from an infectious cDNA clone of the PRRS virus of the present invention. The resulting recombinant modified PRRS virus is expected to be replication-defective in pigs and to induce an immune response to the other PRRS virus proteins without the risks of clinical disease, spread to non-vaccinated animals, or reversion to virulence associated with attenuated live vaccines.

Deletion of ORF4 from an infectious clone was accomplished as follows. Plasmid p2_7D-4 (see FIG. 1) was used as template in PCR to amplify the 5' and 3' flanking regions upstream and downstream of ORF4. The upstream flank forward primer was 5'-AGGTCGACGGCGGCAAGGTTTCACCTAGAGTGGCTGCGTCCCTTCT-3' (SEQ ID NO:37). This primer binds to genome positions 13194–13241, near the beginning of ORF4, and introduces a mutation at position 13225 which destroys the ATG start codon of ORF4 without altering the overlapping amino acid sequence of ORF3. The upstream flank reverse primer was 5'-TCTTAAGCATTGGCTGTGATGGTGATATAC-3' (SEQ ID NO:38). This primer binds to genome positions 13455–13477 within the ORF4 coding region, downstream of ORF3, and introduces an AflII site. For the downstream flanking region, the forward primer was 5'-CTTCTTAAGTCCACGCGTTTTCTTCTTGCCTTTTCTATGCTTCT-3' (SEQ ID NO:39). This primer binds to genome positions 13520–13545 in the middle of ORF4, and introduces AflII and MluI sites for directional cloning of foreign genes. The reverse primer was 5'-TGCCCGGTCCCTTGCCTCT3' (SEQ ID NO:40). This primer binds to genome positions 14981–14999 in the ORF7 coding sequence. A three-way ligation was performed using the SalI-AflII fragment of the upstream flank PCR product, the AflII-BstEII fragment of the downstream flank PCR product, and the SalI-BstEII fragment from plasmid p2_7D-4. All fragments were gel-purified following digestion. The resulting plasmid p2_7D-4delta4N has 42 bases of the central portion of ORF4 deleted and replaced with a 15 base artificial cloning site. The cloning site contains two restriction sites (AflII and MluI) that are absent from both the viral genome and the plasmid backbone. These can be used to facilitate directional cloning of foreign genes into the space previously occupied by ORF4. The cloning site also contains a stop codon (TAA) that is in frame with ORF4 and further assures that functional ORF4 protein is not produced.

It was found that a more extensive deletion of the ORF4 coding sequence could be made without interfering with expression of the downstream ORF5 envelope gene. In this case a shorter downstream flanking region was amplified by PCR using the same template and reverse primer, and using forward primer 5'-GTTTACGCGTCGCTCCTTGGTGGTCG-3' (SEQ ID NO:41). This primer binds to genome positions 13654–13669 near the 3' end of ORF4, and contains an AflII site. Two-way ligation between the AflII-BstEII fragment of the downstream flank PCR product and the AflII-BstEII fragment from plasmid p2_7D-4delta4N yielded the new plasmid p2_7D-4delta4NS. This plasmid has 176 bases of the ORF4 coding sequence deleted and replaced with the 15 base cloning site.

The changes made in p2_7D-4delta4N and p2_7Ddelta4NS were incorporated into the full-length genomic clone by replacing the BsrGI-SpeI fragment from pCMV-S-P129 with the modified BsrGI-SpeI fragments from p2_7D-4delta4N and p2_7D-4delta4NS. The resulting plasmids pCMV-S-P129delta4N and pCMV-S-P129delta4NS were used to transfect cells.

In contrast to pCMV-S-P129, transfection of MARC-145 cells with plasmids pCMV-S-P129delta4N or pCMV-S-P129delta4NS did not result in viral plaques or fluorescent foci. Individual transfected cells could be seen to be producing the ORF7 nucleocapsid protein, suggesting that the ORF4 gene product is not required for RNA replication or expression of viral genes, but is essential for release of infectious progeny virus. Since deletion of ORF4 is lethal to virus replication, it is necessary to provide this protein. This can be accomplished by using a complementing cell line. We created ORF4-expressing MARC-145 cell lines by stable transfecting cells with a plasmid containing both ORF4 and the neomycin resistance gene. After selection for neomycin resistance using the antibiotic G418, single-cell colonies were expanded and characterized. After transfection with pCMV-S-P129delta4NS, three ORF4-expressing cell clones yielded live virus that could be propagated in these cells but not in MARC-145 cells. One of these, MARC400E9, was further characterized. Immunofluorescent staining for viral nucleocapsid in MARC400E9 cells transfected with plasmid pCMV-S-P129delta4NS was positive.

Example VI

Use of Gene-Deleted PRRS Virus as a Vector for Expression of Foreign Genes

In order to determine whether heterologous genes can be expressed from a gene-deleted PRRS virus, we inserted a copy of green fluorescent protein (GFP) into the site of ORF4 deletion in plasmid pCMV-S-P129delta4N. The GFP gene was amplified from a commercially available plasmid vector using PCR primers that introduced an AflII site at the 5' end of the gene and an MluI site at the 3' end of the gene. The resulting plasmid pCMV-S-P129delta4N-GFP was used to transfect MARC-145 and MARC400E9 cells. As anticipated, MARC-145 cells did not support replication of the ORF4-deleted virus. Single green cells resulting from primary tranfection were seen under the UV scope, indication that GFP was being expressed, but the virus did not spread to neighboring cells and no CPE was observed. In contrast, large green foci were observed in transfected MARC400E9 cells. Visible plaques formed and merged, destroying the monolayer. These results indicate that foreign genes can be expressed from ORF4-deleted PRRS virus, and that increasing the size of the viral genome by 692 bases (4.5%) does not interfere with packaging of the viral RNA into infectious particles.

Example VII

Use of Replication-Competent PRRS Virus as a Vector for Expression of Foreign Genes In order to determine whether heterologous genes can be expressed from a replication-competent PRRS virus, we inserted a copy of GFP into the region between ORF1b and ORF2. Since the leader/junction (L/J) sequence for ORF2 lies within ORF1b, this L/J sequence was used to drive expression of the GFP gene and a copy of the ORF6 L/J sequence was inserted downstream from GFP to drive expression of ORF2.

Plasmid p2__7D-4 (see FIG. 1) was used as template in PCR to amplify the 5' and 3' flanking regions upstream and downstream of the insertion site. The upstream flank forward primer was 5'-AACAGAAGAGTTGTCGGGTCC-AC-3' (SEQ ID NO:42). This primer binds to genome positions 11699–11721 in ORF1b. The upstream flank reverse primer was 5'-GCTTTGACGCGTCCCCACTT-AAGTTCAATTCAGGCCTAAAGTTGGTTCA-3' (SEQ ID NO:43). This primer binds to genome positions 12031–12055 in ORFIb and adds AflII and MluI sites for directional cloning of foreign genes between ORF1b and ORF2. The downstream flank forward primer was 5'-GCGACGCGTGTTCCGTGGCAACCCCTTTAACCA-GAGTTTCAGCGGAACAATGAAATGGG GTCTAT-ACAAAGCCTCTTCGACA-3' (SEQ ID NO:44). This primer binds to genome positions 12056–12089 in ORF2 and contains an MluI site followed by the 40 bases that precede the start of ORF6 (containing the ORF6 L/J sequence). The downstream flank reverse primer was 5'-AACAGAACGGCACGATACACCACAAA-3' (SEQ ID NO:45). This primer binds to genome positions 13819–13844 in ORF5. A three-way ligation was performed using the Eco47III-MluI fragment of the upstream flank PCR product, the MluI-BsrGI fragment from the downstream flank PCR product, and the Eco47III-BsrGI fragment from pCMV-S-P129. The resulting plasmid pCMV-S-P129-1bMCS2 contains the entire P129 genome with a cloning site and an additional L/J site between ORF1b and ORF2. The plasmid produces functionally normal virus when transfected into MARC-145 cells.

The GFP gene from a commercially available plasmid was PCR amplified using primers that add an AflII site to the 5' end and an MluI site to the 3' end of the gene. After digestion of the PCR fragment and PCMV-SP129–1bMCS2 with AflII and MluI, the insert was ligated into the vector to yield plasmid pCMV-S-P129-1bGFP2. This plasmid produced green plaques when transfected into MARC-145 cells. The resulting virus could be passaged onto MARC-145 cells and continued to produce green plaques when observed under the UV scope. Thus, foreign genes may be expressed from replication-comptetent PRRS virus vectors. The P129-1bGFP2 virus contains a genome which is 774 bases (5%) longer than that of its P129 parent, yet it is packaged normally.

DEPOSIT OF BIOLOGICAL MATERIALS

The following biological material was deposited with the American Type Culture Collection (ATCC) at 10801 University Blvd., Manassas, Va., 20110–2209, USA, on Nov. 19, 1998 and were assigned the following accession numbers:

| Plasmid | Accession No. |
|---|---|
| plasmid pT7P129A | 203488 |
| plasmid pCMV-S-P129 | 203489 |

All patents, patent applications, and publications cited above are incorporated herein by reference in their entirety.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. An isolated polynucleotide molecule comprising a DNA sequence encoding an infectious RNA molecule encoding a North American PRRS virus, wherein said DNA sequence is SEQ ID NO:1 or a sequence that hybridizes to the complement of SEQ ID NO:1 under highly stringent condition, wherein said highly stringent conditions comprise hybridization to filter-bound DNA in 0.5 M $NaHPO_4$, 7% SDS, 1 mM EDTA at 65° C., and washing in 0.1×SSC/0.1% SDS at 68° C.

2. A transfected host cell comprising a DNA sequence encoding an infectious RNA molecule encoding a North American PRRS virus, wherein said DNA sequence is SEQ ID NO:1 or a sequence that hybridizes to the complement of SEQ ID NO:1 under highly stringent condition, wherein said highly stringent conditions comprise hybridization to filter-bound DNA in 0.5 M $NaHPO_4$, 7% SDS, 1 mM EDTA at 65° C., and washing in 0.1×SSC/0.1% SDS at 68° C., which transfected host cell is capable of expressing the encoded North American PRRS virus.

3. An isolated polynucleotide molecule comprising a DNA sequence encoding an infectious RNA molecule encoding a North American PRRS virus, wherein said DNA sequence is SEQ ID NO: 1.

4. An isolated polynucleotide molecule in the form of a plasmid, wherein said isolated polynucleotide molecule comprises a DNA sequence encoding an infectious RNA molecule encoding a North American PRRS virus, wherein said DNA sequence is SEQ ID NO: 1.

5. An isolated infectious RNA molecule encoded by an isolated polynucleotide molecule comprising SEQ ID NO: 1, which infectious RNA molecule encodes a North American PRRS virus.

6. A recombinant North American PRRS virus encoded by an isolated polynucleotide molecule comprising a DNA sequence encoding an infectious RNA molecule encoding a North American PRRS virus, wherein said DNA sequence is SEQ ID NO: 1.

* * * * *

SEQUENCE LISTING

```
<160> NUMBER OF SEQ ID NOS:  45

<210> SEQ ID NO 1
<211> LENGTH: 15450
<212> TYPE: DNA
<213> ORGANISM: Artificial Sequence
<220> FEATURE:
<223> OTHER INFORMATION: Description of Artificial Sequence:  cDNA
      corresponding to North American Porcine
      Reproductive And Respiratory Syndrome (PRRS) Virus
      Genome.

<400> SEQUENCE: 1

atgacgtata ggtgttggct ctatgccacg gcatttgtat tgtcaggagc tgtgaccatt     60

ggcacagccc aaaacttgct gcacggaaaa cgcccttctg tgacagcctt cttcagggga    120

gcttaggggt ctgtccctag caccttgctt ctggagttgc actgctttac ggtctctcca    180

cccctttaac catgtctggg atacttgatc ggtgcacgtg cacccccaat gccagggtgt    240

ttatggcgga gggccaagtc tactgcacac gatgtctcag tgcacggtct ctccttcctc    300

tgaatctcca agttcctgag cttggggtgc tgggcctatt ttataggccc gaagagccac    360

tccggtggac gttgccacgt gcattcccca ctgtcgagtg ctcccccgcc ggggcctgct    420
```

-continued

```
ggctttctgc gatctttcca attgcacgaa tgaccagtgg aaacctgaac tttcaacaaa    480
gaatggtgcg ggttgcagct gagatttaca gagccggcca actcacccct gcagttttga    540
aggctctaca agtttatgaa cggggttgtc gctggtaccc cattgtcgga cctgtccctg    600
gagtggccgt tcacgccaac tccctacatg tgagtgacaa acctttcccg ggagcaactc    660
atgtgttaac caacctaccg ctcccgcaga ggcccaagcc tgaagacttt tgcccttttg    720
agtgtgctat ggctgacgtc tatgacatta gccatgacgc cgtcatgtat gtggccagag    780
ggaaagtctc ctgggcccct cgtggcgggg atgaagtgaa atttgaaacc gtccccgaag    840
agttgaagtt gattgcgaac cgactccaca tctccttccc gccccaccac gcagtggaca    900
tgtctgagtt tgccttcata gcccctggga gtggtgtctc cttgcgggtc gagcaccaac    960
acggttgcct tcccgctgat actgtccctg aagggaactg ctggtggtgc ttgtttgact   1020
tgctcccacc ggaagttcag aataaagaaa ttcgccgtgc taaccaattt ggctatcaaa   1080
ccaagcatgg tgtccctggc aagtacctac agcggaggct gcaagttaat ggtctccgag   1140
cagtgactga tacagatgga cctattgtcg tacagtactt ctctgttagg gagagttgga   1200
tccgccactt cagactggcg gaagaaccta gcctccctgg gtttgaagac ctcctcagaa   1260
taagggtaga gcctaatacg tcgccattgg gtggcaaggg tgaaaaaatc ttccggtttg   1320
gcagtcacaa gtggtacggt gctggaaaga gagcaaggag agcacgctct ggtgcaactg   1380
ccacggtcgc tcactgcgct ttgcccgctc gcgaagccca gcaggccaag aagctcgagg   1440
ttgccagcgc caacagggct gagcatctca agtactattc ccgcctgcc gacgggaact   1500
gtggttggca ctgcatttcc gccattacca accggatggt gaattccaaa tttgaaacca   1560
ctcttcccga gagagtgaga ccttcagatg actgggctac tgacgaggat cttgtgaata   1620
ccatccaaat cctcaggctc cccgcggcct tggacaggaa cggtgcttgt gctggcgcca   1680
agtacgtgct caagctggaa ggtgagcact ggaccgtctc tgtgacccct gggatgaccc   1740
cttctttgct ccccttgaa tgtgttcagg gttgttgtga gcataagagc ggtcttggtt   1800
tcccagacgt ggtcgaagtt tccggatttg accctgcctg tcttgaccga cttgctgaga   1860
taatgcactt acctagcagt gtcatcccag ctgctctggc cgagatgtcc gacgacttca   1920
atcgtctggc ttccccggcc gccactgtgt ggactgtttc gcaattcttt gcccgccaca   1980
gaggaggaga gcatcctgac caggtgtgct tagggaaaat tatcaacctt tgtcaggtga   2040
ttgaggaatg ctgctgttcc cggaacaaag ccaaccgggc taccccggaa gaggttgcgg   2100
caaaagttga ccagtacctc cgtggtgcag caagccttgg agaatgcttg gccaagcttg   2160
agagggctcg cccgccgagc gcgatggaca cctcctttga ttggaatgtt gtgcttcctg   2220
gggttgagac ggcggatcag acaaccaaac agctccatgt caaccagtgc cgcgctctgg   2280
ttcctgtcgt gactcaagag cctttggaca gagactcggt ccctctgacc gccttctcgc   2340
tgtccaattg ctactaccct gcacaaggtg acgaggtccg tcaccgtgag aggctaaact   2400
ccgtgctctc taagttggag ggggttgttc gtgaggaata tgggctcacg ccaactggac   2460
ctggcccgcg acccgcactg ccgaacgggc tcgacgagct taaagaccag atggaggagg   2520
atctgctgaa attagtcaac gcccaggcaa cttcagaaat gatggcctgg gcagccgagc   2580
aggttgatct aaaagcttgg gtcaaaaatt acccacggtg gacaccgcca ccccctccac   2640
caagagttca gcctcgaaaa acgaagtctg tcaagagctt gctagagaac aagcctgtcc   2700
ctgctccgcg caggaaggtc agatctgatt atggcagccc gattttgatg ggcgacaatg   2760
```

-continued

```
ttcctaacgg ttgggaagat tcgactgttg gtggtcccct tgacctttcg gcaccatccg   2820

agccgatgac acctctgagt gagcctgtac ttatttccag gccagtgaca tctttgagtg   2880

tgccggcccc agttcctgca ccgcgtagag ctgtgtctcg accgatgacg ccctcgagtg   2940

agccaatttt tgtgtctgca ctgcgacaca aatttcagca ggtggaaaaa gcaaatctgg   3000

cggcagcagc gccgatgtac caggacgaac ccttagattt gtctgcatcc tcacagactg   3060

aatatggggc ttctccccta acaccaccgc agaacgtggg cattctggag gtaagggggc   3120

aagaagctga ggaagttctg agtgaaatct cggatattct gaatgatacc aaccctgcac   3180

ctgtgtcatc aagcagctcc ctgtcaagtg ttaggatcac acgcccaaaa tactcagctc   3240

aagccattat cgacttgggc gggccctgca gtgggcacct ccaaagggaa aaagaagcat   3300

gcctccgcat catgcgtgag gcttgtgatg cggccaagct tagtgaccct gccacgcagg   3360

aatggctttc tcgcatgtgg gatagggtgg acatgctgac ttggcgcaac acgtctgctt   3420

accaggcgtt tcgcacctta gatggcaggt ttgggtttct cccaaagatg atactcgaga   3480

cgccgccgcc ctacccgtgt gggtttgtga tgttgcctca cacccctgca ccttccgtga   3540

gtgcagagag cgaccttacc atcggttcag tcgccactga agatattcca cgcatcctcg   3600

ggaaaataga aaataccggt gagatgatca accagggacc cttggcatcc tctgaggaag   3660

aaccggtata caaccaacct gccaaagact cccggatatc gtcgcggggg tctgacgaga   3720

gcacagcagc tccgtccgca ggtacaggtg gcgccggctt atttactgat ttgccacctt   3780

cagacggcgt agatgcggac ggtggggggc cgttgcagac ggtaagaaag aaagctgaaa   3840

ggctcttcga ccaattgagc cgtcaggttt ttaacctcgt ctcccatctc cctgttttct   3900

tctcacacct cttcaaatct gacagtggtt attctccggg tgattggggt tttgcagctt   3960

ttactctatt ttgcctcttt ttgtgttaca gctacccatt cttcggtttc gttcccctct   4020

tgggtgtatt ttctgggtct tctcggcgtg tgcgcatggg ggtttttggc tgctggctgg   4080

cttttgctgt tggcctgttc aagcctgtgt ccgacccagt cggcactgct tgtgagtttg   4140

actcgccaga gtgtaggaac gtccttcatt cttttgagct tctcaaacct tgggaccctg   4200

ttcgcagcct tgttgtgggc cccgtcggtc tcggtcttgc cattcttggc aggttactgg   4260

gcggggcacg ctacatctgg catttttgc ttaggcttgg cattgttgca gattgtatct   4320

tggctggagc ttatgtgctt tctcaaggta ggtgtaaaaa gtgctgggga tcttgtataa   4380

gaactgctcc taatgaaatc gccttcaacg tgttcccttt tacacgtgcg accaggtcgt   4440

cactcatcga cctgtgcgat cggttttgtg cgccaaaagg catggacccc attttcctcg   4500

ccactgggtg gcgtgggtgc tggaccggcc gaagtcccat tgagcaaccc tctgaaaaac   4560

ccatcgcgtt cgcccagttg gatgaaaaga ggattacggc tagaactgtg gtcgctcagc   4620

cttatgatcc taatcaagcc gtaaagtgct tgcgggtgtt acaggcgggt ggggcgatgg   4680

tggccgaggc agtcccaaaa gtggtcaaag tttctgctat tccattccga gccccctttt   4740

ttcccaccgg agtgaaagtt gatcccgagt gcaggatcgt ggtcgacccc gatactttta   4800

ctacagccct ccggtctggt tactctacca caaacctcgt ccttggtgtg ggggactttg   4860

cccagctgaa tggactaaag atcaggcaaa tttccaagcc ttcgggagga ggcccacacc   4920

tcattgctgc cctgcatgtt gcctgctcga tggcgttgca catgcttgct ggggtttatg   4980

taacttcagt ggggtcttgc ggtgccggca ccaacgatcc atggtgcact aatccgtttg   5040

ccgttcctgg ctacggacca ggctctctct gcacgtccag attgtgcatc tcccaacatg   5100

gccttaccct gcccttgaca gcacttgtgg cgggattcgg tcttcaggaa atcgccttgg   5160
```

-continued

```
tcgttttgat tttcgtttcc atcggaggca tggctcatag gttgagttgt aaggctgata   5220
tgctgtgcat cttacttgca atcgccagct atgtttgggt accccttacc tggttgcttt   5280
gtgtgtttcc ttgttggttg cgctggttct ctttgcaccc cctcaccatc ctatggttgg   5340
tgtttttctt gatttctgta aatatgcctt cgggaatctt ggccgtggtg ttattggttt   5400
ctctttggct tttgggacgt tatactaaca ttgctggtct tgtcaccccc tatgatattc   5460
atcattacac cagtggcccc cgcggtgttg ccgccttagc taccgcacca gatggaacct   5520
acttggctgc cgtccgccgc gctgcgttga ctggtcgcac catgctgttc accccgtctc   5580
agcttgggtc ccttcttgag ggcgctttca gaactcgaaa gccctcactg aacaccgtca   5640
atgtggttgg gtcctccatg ggctctggtg gagtgttcac catcgacggg aaaattaggt   5700
gcgtgactgc cgcacatgtc cttacgggta attcggctag ggtttccgga gtcggcttca   5760
atcaaatgct tgactttgat gtgaaagggg acttcgccat agctgattgc ccgaattggc   5820
aaggagctgc tcccaagacc caattctgcg aggatggatg ggctggccgt gcctattggc   5880
tgacatcctc tggcgtcgaa cccggtgtta ttgggaatgg attcgccttc tgcttcaccg   5940
cgtgcggcga ttccgggtcc ccagtgatca ccgaagctgg tgagcttgtc ggcgttcaca   6000
caggatcaaa taaacaagga ggtggcatcg tcacgcgccc ttcaggccag ttttgtaacg   6060
tggcacccat caagctgagc gaattaagtg aattctttgc tggacccaag gtcccgctcg   6120
gtgatgtgaa ggttggcagc cacataatta aagatacgtg cgaagtacct tcagatcttt   6180
gcgccttgct tgctgccaaa cctgaactgg agggaggcct ctccaccgtc caacttctgt   6240
gtgtgttttt cctactgtgg agaatgatgg gacatgcctg gacgcccttg gttgctgtgg   6300
ggtttttcat tctgaatgag gttctcccag ctgtcctggt tcggagtgtt ttctcctttg   6360
ggatgtttgt gctatcttgg ctcacaccat ggtctgcgca agttctgatg atcaggcttc   6420
taacagcagc tcttaacagg aacagatggt cacttgcctt ttacagcctt ggtgcggtga   6480
ccggttttgt cgcagatctt gcggcaactc aagggcaccc gttgcaggca gtaatgaatt   6540
tgagcaccta tgccttcctg cctcggatga tggttgtgac ctcaccagtc ccagtgattg   6600
cgtgtggtgt tgtgcaccta cttgccatca ttttgtactt gttcaagtac cgcggcctgc   6660
acaatgttct tgttggtgat ggagcgtttt ctgcagcttt cttcttgcga tactttgccg   6720
agggaaagtt gagggaaggg gtgtcgcaat cctgcggaat gaatcatgag tcattaactg   6780
gtgccctcgc tatgagactc aatgacgagg acttggactt ccttacgaaa tggactgatt   6840
ttaagtgctt tgtttctgcg tccaacatga ggaatgcagc aggccaattc atcgaggctg   6900
cctatgcaaa agcacttaga attgaacttg cccagttggt gcaggttgat aaggttcgag   6960
gtactttggc caagcttgag gcttttgctg ataccgtggc accccaactc tcgcccggtg   7020
acattgttgt tgctcttggc catacgcctg ttggcagcat cttcgaccta aaggttggtg   7080
gtaccaagca tactctccaa gtcattgaga ccagagtcct tgccgggtcc aaaatgaccg   7140
tggcgcgcgt cgttgaccca acccccacgc ccccacccgc acccgtgccc atccccctcc   7200
caccgaaagt tctagagaat ggtcccaacg cctgggggga tggggaccgt ttgaataaga   7260
agaagaggcg taggatggaa accgtcggca tctttgtcat gggtgggaag aagtaccaga   7320
aattttggga caagaattcc ggtgatgtgt tttacgagga ggtccatgac aacacagatg   7380
cgtgggagtg cctcagagtt ggtgaccctg ccgactttga ccctgagaag ggaactctgt   7440
gtgggcatac tactattgaa gataaggatt acaaagtcta cgcctcccca tctggcaaga   7500
```

-continued

```
agttcctggt ccccgtcaac tcagagagcg gaagagccca atgggaagct gcaaagcttt   7560
ccgtggagca ggcccttggc atgatgaatg tcgacggtga actgacggcc aaagaagtgg   7620
agaaactgaa aagaataatt gacaaacttc agggcctgac taaggagcag tgtttaaact   7680
gctagccgcc agcggcttga cccgctgtgg tcgcggcggc ttggttgtta ctgagacagc   7740
ggtaaaaata gtcaaatttc acaaccggac tttcacccta gggcctgtga atttaaaagt   7800
ggccagtgag gttgagctga aagacgcggt cgagcacaac caacacccgg ttgcaagacc   7860
ggttgacggt ggtgttgtgc tcctgcgttc cgcagttcct tcgcttatag atgtcctgat   7920
ctccggtgct gacgcatctc ctaagttact cgctcgtcac gggccgggga acactgggat   7980
cgatggcacg ctttgggact ttgaggccga ggccaccaaa gaggaaattg cactcagtgc   8040
gcaaataata caggcttgtg acattaggcg cggcgacgca cctgaaattg gtctccctta   8100
caagctgtac cctgttaggg gcaaccctga gcgggtaaaa ggagttttac agaatacaag   8160
gtttggagac ataccttaca aaacccccag tgacactgga agcccagtgc acgcggctgc   8220
ctgcctcacg cccaatgcca ctccggtgac tgatgggcgc tctgtcttgg ctactaccat   8280
gccctccggt tttgaattgt atgtaccgac cattccagcg tctgtccttg attatcttga   8340
ctctaggcct gactgcccca aacagttgac agagcacggc tgtgaggatg ccgcattgag   8400
agacctctcc aagtatgact tgtccaccca aggctttgtt ttacctgggg ttcttcgcct   8460
tgtgcgtaag tacctgtttg cccatgtggg taagtgcccg cccgttcatc ggccttccac   8520
ttaccctgcc aagaattcta tggctggaat aaatgggaac aggtttccaa ccaaggacat   8580
tcagagcgtc cctgaaatcg acgttctgtg cgcacaggcc gtgcgagaaa actggcaaac   8640
tgttacccct tgtaccctca agaaacagta ttgtgggaag aagaagacta ggacaatact   8700
cggcaccaat aatttcattg cgttggccca ccgggcagcg ttgagtggtg tcacccaggg   8760
cttcatgaaa aaggcgttta actcgcccat cgccctcggg aaaaacaaat ttaaggagct   8820
acagactccg gtcttaggca ggtgccttga agctgatctt gcatcctgtg atcgatccac   8880
acctgcaatt gtccgctggt ttgccgccaa tcttctttat gaacttgcct gtgctgaaga   8940
gcacctaccg tcgtacgtgc tgaactgctg ccatgaccta ttggtcacgc agtccggcgc   9000
agtgactaag aggggtggcc tatcgtctgg cgacccgatc acttctgtgt ctaacaccat   9060
ttacagcttg gtgatatatg cacagcacat ggtgcttagt tactttaaaa gtggtcaccc   9120
tcatggcctt ctgttcctac aagaccagct gaagttcgag gacatgctca aagtccaacc   9180
cctgatcgtc tattcggacg acctcgtgct gtatgccgaa tctcccacca tgccgaacta   9240
ccactggtgg gtcgaacatc tgaatttgat gctgggtttt cagacggacc caaagaagac   9300
agccataacg gactcgccat catttctagg ctgtaggata ataaatggac gccagctagt   9360
ccccaaccgt gacaggatcc tcgcggccct cgcttaccat atgaaggcaa gcaatgtttc   9420
tgaatactac gccgcggcgg ctgcaatact catggacagc tgtgcttgtt tagagtatga   9480
tcctgaatgg tttgaagagc ttgtggttgg gatagcgcag tgcgcccgca aggacggcta   9540
cagctttccc ggcccgccgt tcttcttgtc catgtgggaa aaactcagat ccaatcatga   9600
ggggaagaag tccagaatgt gcgggtattg cggggccccg gctccgtacg ccactgcctg   9660
tggcctcgac gtctgtattt accacaccca cttccaccag cattgtccag tcataatctg   9720
gtgtggccac ccggctggtt ctggttcttg tagtgagtgc aaaccccccc tagggaaagg   9780
cacaagccct ctagatgagg tgttagaaca agtcccgtat aagcctccac ggactgtaat   9840
catgcatgtg gagcagggtc tcacccctct tgacccaggc agataccaga ctcgccgcgg   9900
```

-continued

```
attagtctcc gttaggcgtg gcatcagagg aaacgaagtt gacctaccag acggtgatta   9960
tgctagcacc gccctactcc ccacttgtaa agagatcaac atggtcgctg tcgcctctaa  10020
tgtgttgcgc agcaggttca tcatcggtcc gcccggtgct gggaaaacat actggctcct  10080
tcagcaggtc caggatggtg atgtcattta cacaccgact caccagacca tgctcgacat  10140
gattagggct ttggggacgt gccggttcaa cgtcccagca ggtacaacgc tgcaattccc  10200
tgccccctcc cgtaccggcc cgtgggttcg catcctggcc ggcggttggt gtcctggtaa  10260
gaattccttc ctggatgaag cagcgtattg taatcacctt gatgtcttga ggctccttag  10320
caaaaccacc cttacctgtc tgggagactt caaacaactc cacccagtgg gttttgattc  10380
tcattgctat gtttttgaca tcatgcctca gacccagttg aagaccatct ggagattcgg  10440
acagaacatc tgtgatgcca tccaaccaga ttacagggac aaacttgtgt ccatggtcaa  10500
cacaacccgt gtaacctaca tggaaaaacc tgtcaagtat gggcaagtcc tcacccctta  10560
ccacagggac cgagaggacg gcgccatcac aattgactcc agtcaaggcg ccacatttga  10620
tgtggttaca ctgcatttgc ccactaaaga ttcactcaac aggcaaagag cccttgttgc  10680
tatcaccagg gcaagacatg ctatctttgt gtatgaccca cacaggcaat tgcagagcat  10740
gtttgatctt cctgcgaagg gcacacccgt caacctcgca gtgcaccgtg atgagcagct  10800
gatcgtactg gatagaaata ataaagaatg cacagttgct caggctatag gcaacggaga  10860
taaattcagg gccaccgaca agcgcgttgt agattctctc cgcgccattt gtgctgatct  10920
ggaagggtcg agctccccgc tccccaaggt cgcacacaac ttgggatttt atttctcacc  10980
tgatttgaca cagtttgcta aactcccggt agaccttgca ccccactggc ccgtggtgac  11040
aacccagaac aatgaaaagt ggccggatcg gctggttgcc agccttcgcc ctgtccataa  11100
gtatagccgt gcgtgcattg gtgccggcta tatggtgggc ccctcggtgt ttctaggcac  11160
ccctggggtc gtgtcatact acctcacaaa atttgtcaag ggcgaggctc aagtgcttcc  11220
ggagacagtc ttcagcaccg gccgaattga ggtggattgc cgggagtatc ttgatgacag  11280
ggagcgagaa gttgctgagt ccctcccaca tgccttcatt ggcgacgtca aaggcaccac  11340
cgttggggga tgtcatcatg tcacctccaa ataccttccg cgcttccttc ccaaggaatc  11400
agtcgcggta gtcggggttt cgagccccgg gaaagccgca aaagcagtgt gcacattgac  11460
ggatgtgtac ctcccagacc ttgaggccta cctccaccca gagactcagt ctaagtgctg  11520
gaaagttatg ttggacttca aggaagttcg actgatggtc tggaaagaca agacggccta  11580
tttccaactt gaaggccgct atttcacctg gtatcagctt gcaagctacg cctcgtacat  11640
ccgtgttcct gtcaactcca cggtgtatct ggacccctgc atgggccctg ccctttgcaa  11700
cagaagagtt gtcgggtcca cccattgggg agctgacctc gcagtcaccc cttatgatta  11760
cggtgctaaa atcatcttgt ctagcgctta ccatggtgaa atgcctcctg gatacaagat  11820
tctggcgtgc gcggagttct cgctcgacga cccagtcaag tacaaacaca cctggggttt  11880
tgaatcggat acagcgtatc tgtatgagtt caccggaaac ggtgaggact gggaggatta  11940
caatgatgcg tttcgtgcgc gccagaaagg gaaaatttat aaggccactg ctaccagcat  12000
gaagttttat tttcccccgg gccccgtcat tgaaccaact ttaggcctga attgaaatga  12060
aatggggtct atacaaagcc tcttcgacaa aattggccag ctttttgtgg atgctttcac  12120
ggaatttttg gtgtccattg ttgatatcat catatttttg gccattttgt ttggcttcac  12180
catcgccggt tggctggtgg tcttttgcat cagattggtt tgctccgcgg tattccgtgc  12240
```

-continued

```
gcgccctgcc attcaccctg agcaattaca gaagatccta tgaggccttt ctttctcagt  12300

gccgggtgga cattcccacc tggggggtaa aacacccttt ggggatgttt tggcaccata  12360

aggtgtcaac cctgattgat gaaatggtgt cgcgtcgaat gtaccgcatc atggaaaaag  12420

cagggcaagc tgcctggaaa caggtggtga gcgaggctac gctgtctcgc attagtagtt  12480

tggatgtggt ggctcatttt caacatcttg ccgccattga agccgagacc tgtaaatatt  12540

tggcttctcg actgcccatg ctacacaacc tgcgcatgac agggtcaaat gtaaccatag  12600

tgtataatag cactttaaat caggtgtttg ctatttttcc aacccctggt tcccggccaa  12660

agcttcatga ttttcagcaa tggctaatag ctgtacattc ctccatattt tcctctgttg  12720

cagcttcttg tactcttttt gttgtgctgt ggttgcgggt tccaatgcta cgtactgttt  12780

ttggtttccg ctggttaggg gcaatttttc tttcgaactc atggtgaatt acacggtgtg  12840

tccaccttgc ctcacccgac aagcagccgc tgaggtcctt gaacccggta ggtctctttg  12900

gtgcaggata gggcatgacc gatgtgggga ggacgatcac gacgaactag ggttcatggt  12960

tccgcctggc ctctccagcg aaagccactt gaccagtgtt tacgcctggt tggcgttcct  13020

gtccttcagc tacacggccc agttccatcc cgagatattt gggataggga acgtgagtga  13080

agtttatgtt gacatcaagc accaattcat ctgcgccgtt catgacgggc agaacaccac  13140

cttgcctcgc catgacaata tttcagccgt atttcagacc tactatcaac atcaggtcga  13200

cggcggcaat tggtttcacc tagaatggct gcgtcccttc ttttcctctt ggttggtttt  13260

aaatgtttcg tggtttctca ggcgttcgcc tgcaagccat gtttcagttc gagtctttca  13320

gacatcaaaa ccaacactac cgcagcatca ggctttgttg tcctccagga catcagctgc  13380

cttaggcatg gcgactcgtc ctttccgacg attcgcaaaa gctctcaatg ccgcacggcg  13440

atagggacac ccgtgtatat caccatcaca gccaatgtga cagatgagaa ttacttacat  13500

tcttctgatc tcctcatgct ttcttcttgc cttttctatg cttctgagat gagtgaaaag  13560

ggattcaagg tggtgtttgg caatgtgtca ggcatcgtgg ctgtgtgtgt caactttacc  13620

agctacgtcc aacatgtcaa agagtttacc caacgctcct tggtggtcga tcatgtgcgg  13680

ctgcttcatt tcatgacacc tgagaccatg aggtgggcaa ccgttttagc ctgtcttttt  13740

gccatcctac tggcaatttg aatgttcaag tatgttgggg aaatgcttga ccgcgggctg  13800

ttgctcgcga ttgctttctt tgtggtgtat cgtgccgttc tgttttgctg tgctcggcag  13860

cgccaacagc agcagcagct ctcattttca gttgatttat aacttgacgc tatgtgagct  13920

gaatggcaca gattggctgg cagaaaaatt tgattgggca gtggagactt ttgtcatctt  13980

tcccgtgttg actcacattg tttcctatgg tgcactcacc accagccatt tccttgacac  14040

agttggtctg gttactgtgt ccaccgccgg gttttatcac gggcggtatg tcttgagtag  14100

catctacgcg gtctgtgctc tggctgcgtt gatttgcttc gttattaggc ttgcgaagaa  14160

ctgcatgtcc tggcgctact cttgtaccag atataccaac ttccttctgg acactaaggg  14220

cagactctat cgttggcggt cgcccgttat catagaaaaa gggggtaagg ttgaggtcga  14280

aggtcacctg atcgacctca aaagagttgt gcttgatggt tccgtggcaa ccccttttaac  14340

cagagtttca gcggaacaat ggggtcgtct ctagacgact tttgccatga tagcacggct  14400

ccacaaaagg tgcttttggc gttttccatt acctacacgc cagtaatgat atatgctcta  14460

aaggtaagtc gcggccgact actagggctt ctgcaccttt tgatctttct gaattgtgct  14520

tttaccttcg ggtacatgac attcgagcac tttcagagca caaatagggt cgcgctcact  14580

atgggagcag tagttgcact tctttggggg gtgtactcag ccatagaaac ctggaaattc  14640
```

atcacctcca gatgccgttt gtgcttgcta ggccgcaagt acattctggc cctgcccac 14700 cacgtcgaaa gtgccgcggg ctttcatccg attgcggcaa atgataacca cgcatttgtc 14760
gtccggcgtc ccggctccac tacggttaac ggcacattgg tgcccgggtt gaaaagcctc 14820
gtgttgggtg gcagaaaagc tgttaaacag ggagtggtaa accttgtcaa atatgccaaa 14880
taacaacggc aagcagcaaa agaaaaagaa ggggaatggc cagccagtca atcagctgtg 14940
ccagatgctg ggtaaaatca tcgcccagca aaaccagtcc agaggcaagg gaccgggcaa 15000
gaaaagtaag aagaaaaacc cggagaagcc ccattttcct ctagcgaccg aagatgacgt 15060
caggcatcac ttcacccctg gtgagcggca attgtgtctg tcgtcgatcc agactgcctt 15120
taaccagggc gctggaactt gtaccctgtc agattcaggg aggataagtt acactgtgga 15180
gtttagtttg ccgacgcatc atactgtgcg cctgatccgc gtcacagcat caccctcagc 15240
atgatgggct ggcattcttt aggcacctca gtgtcagaat tggaagaatg tgtggtggat 15300
ggcactgatt gacattgtgc ctctaagtca cctattcaat tagggcgacc gtgtgggggt 15360
aaaatttaat tggcgagaac catgcggccg caattaaaaa aaaaaaaaaa aaaaaaaaaa 15420
aaaaaaaaaa aaaaaaaaaa aaaaaaaaaa 15450

<210> SEQ ID NO 2
<211> LENGTH: 7494
<212> TYPE: DNA
<213> ORGANISM: Artificial Sequence
<220> FEATURE:
<223> OTHER INFORMATION: Description of Artificial Sequence: cDNA of Open Reading Frame 1a of North American PRRS Virus Genome.

<400> SEQUENCE: 2
atgtctggga tacttgatcg gtgcacgtgc acccccaatg ccagggtgtt tatggcggag 60
ggccaagtct actgcacacg atgtctcagt gcacggtctc tccttcctct gaatctccaa 120
gttcctgagc ttggggtgct gggcctattt tataggcccg aagagccact ccggtggacg 180
ttgccacgtg cattccccac tgtcgagtgc tcccccgccg gggcctgctg gctttctgcg 240
atctttccaa ttgcacgaat gaccagtgga aacctgaact ttcaacaaag aatggtgcgg 300
gttgcagctg agatttacag agccggccaa ctcacccctg cagttttgaa ggctctacaa 360
gtttatgaac ggggttgtcg ctggtacccc attgtcggac ctgtccctgg agtggccgtt 420
cacgccaact ccctacatgt gagtgacaaa cctttcccgg gagcaactca tgtgttaacc 480
aacctaccgc tcccgcagag gcccaagcct gaagactttt gcccttttga gtgtgctatg 540
gctgacgtct atgacattag ccatgacgcc gtcatgtatg tggccagagg gaaagtctcc 600
tgggcccctc gtggcgggga tgaagtgaaa tttgaaaccg tccccgaaga gttgaagttg 660
attgcgaacc gactccacat ctccttcccg ccccaccacg cagtggacat gtctgagttt 720
gccttcatag cccctgggag tggtgtctcc ttgcgggtcg agcaccaaca cggttgcctt 780
cccgctgata ctgtccctga agggaactgc tggtggtgct tgtttgactt gctcccaccg 840
gaagttcaga ataaagaaat tcgccgtgct aaccaatttg gctatcaaac caagcatggt 900
gtccctggca agtacctaca gcggaggctg caagttaatg gtctccgagc agtgactgat 960
acagatggac ctattgtcgt acagtacttc tctgttaggg agagttggat ccgccacttc 1020
agactggcgg aagaacctag cctccctggg tttgaagacc tcctcagaat aagggtagag 1080
cctaatacgt cgccattggg tggcaagggt gaaaaaatct tccggtttgg cagtcacaag 1140

-continued

```
tggtacggtg ctggaaagag agcaaggaga gcacgctctg gtgcaactgc cacggtcgct   1200
cactgcgctt tgcccgctcg cgaagcccag caggccaaga agctcgaggt tgccagcgcc   1260
aacagggctg agcatctcaa gtactattcc ccgcctgccg acgggaactg tggttggcac   1320
tgcatttccg ccattaccaa ccggatggtg aattccaaat ttgaaaccac tcttcccgag   1380
agagtgagac cttcagatga ctgggctact gacgaggatc ttgtgaatac catccaaatc   1440
ctcaggctcc ccgcggcctt ggacaggaac ggtgcttgtg ctggcgccaa gtacgtgctc   1500
aagctggaag gtgagcactg gaccgtctct gtgacccctg ggatgacccc ttctttgctc   1560
ccccttgaat gtgttcaggg ttgttgtgag cataagagcg gtcttggttt cccagacgtg   1620
gtcgaagttt ccggatttga ccctgcctgt cttgaccgac ttgctgagat aatgcactta   1680
cctagcagtg tcatcccagc tgctctggcc gagatgtccg acgacttcaa tcgtctggct   1740
tccccggccg ccactgtgtg gactgtttcg caattctttg cccgccacag aggaggagag   1800
catcctgacc aggtgtgctt agggaaaatt atcaaccttt gtcaggtgat tgaggaatgc   1860
tgctgttccc ggaacaaagc caaccgggct accccggaag aggttgcggc aaaagttgac   1920
cagtacctcc gtggtgcagc aagccttgga gaatgcttgg ccaagcttga gagggctcgc   1980
ccgccgagcg cgatggacac ctcctttgat tggaatgttg tgcttcctgg ggttgagacg   2040
gcggatcaga caaccaaaca gctccatgtc aaccagtgcc gcgctctggt tcctgtcgtg   2100
actcaagagc ctttggacag agactcggtc cctctgaccg ccttctcgct gtccaattgc   2160
tactaccctg cacaaggtga cgaggtccgt caccgtgaga ggctaaactc cgtgctctct   2220
aagttggagg gggttgttcg tgaggaatat gggctcacgc caactggacc tggcccgcga   2280
cccgcactgc cgaacgggct cgacgagctt aaagaccaga tggaggagga tctgctgaaa   2340
ttagtcaacg cccaggcaac ttcagaaatg atggcctggg cagccgagca ggttgatcta   2400
aaagcttggg tcaaaaatta cccacggtgg acaccgccac cccctccacc aagagttcag   2460
cctcgaaaaa cgaagtctgt caagagcttg ctagagaaca agcctgtccc tgctccgcgc   2520
aggaaggtca gatctgatta tggcagcccg attttgatgg gcgacaatgt tcctaacggt   2580
tgggaagatt cgactgttgg tggtcccctt gacctttcgg caccatccga gccgatgaca   2640
cctctgagtg agcctgtact tatttccagg ccagtgacat ctttgagtgt gccggcccca   2700
gttcctgcac cgcgtagagc tgtgtctcga ccgatgacgc cctcgagtga gccaattttt   2760
gtgtctgcac tgcgacacaa atttcagcag gtggaaaaag caaatctggc ggcagcagcg   2820
ccgatgtacc aggacgaacc cttagatttg tctgcatcct cacagactga atatggggct   2880
tctcccctaa caccaccgca gaacgtgggc attctggagg taagggggca agaagctgag   2940
gaagttctga gtgaaatctc ggatattctg aatgatacca accctgcacc tgtgtcatca   3000
agcagctccc tgtcaagtgt taggatcaca cgcccaaaat actcagctca agccattatc   3060
gacttgggcg ggccctgcag tgggcacctc caaagggaaa aagaagcatg cctccgcatc   3120
atgcgtgagg cttgtgatgc ggccaagctt agtgaccctg ccacgcagga atggctttct   3180
cgcatgtggg atagggtgga catgctgact tggcgcaaca cgtctgctta ccaggcgttt   3240
cgcaccttag atggcaggtt tgggtttctc ccaaagatga tactcgagac gccgccgccc   3300
tacccgtgtg ggtttgtgat gttgcctcac acccctgcac cttccgtgag tgcagagagc   3360
gaccttacca tcggttcagt cgccactgaa gatattccac gcatcctcgg gaaaatagaa   3420
aataccggtg agatgatcaa ccagggaccc ttggcatcct ctgaggaaga accggtatac   3480
aaccaacctg ccaaagactc ccggatatcg tcgcgggggt ctgacgagag cacagcagct   3540
```

-continued

```
ccgtccgcag gtacaggtgg cgccggctta tttactgatt tgccaccttc agacggcgta   3600
gatgcggacg gtggggggcc gttgcagacg gtaagaaaga aagctgaaag gctcttcgac   3660
caattgagcc gtcaggtttt taacctcgtc tcccatctcc ctgttttctt ctcacacctc   3720
ttcaaatctg acagtggtta ttctccgggt gattggggtt ttgcagcttt tactctattt   3780
tgcctctttt tgtgttacag ctacccattc ttcggtttcg ttcccctctt gggtgtattt   3840
tctgggtctt ctcggcgtgt gcgcatgggg gtttttggct gctggctggc ttttgctgtt   3900
ggcctgttca agcctgtgtc cgacccagtc ggcactgctt gtgagtttga ctcgccagag   3960
tgtaggaacg tccttcattc ttttgagctt ctcaaacctt gggaccctgt tcgcagcctt   4020
gttgtgggcc ccgtcggtct cggtcttgcc attcttggca ggttactggg cggggcacgc   4080
tacatctggc atttttgct taggcttggc attgttgcag attgtatctt ggctggagct   4140
tatgtgcttt ctcaaggtag gtgtaaaaag tgctggggat cttgtataag aactgctcct   4200
aatgaaatcg ccttcaacgt gttccctttt acacgtgcga ccaggtcgtc actcatcgac   4260
ctgtgcgatc ggttttgtgc gccaaaaggc atggacccca ttttcctcgc cactgggtgg   4320
cgtgggtgct ggaccggccg aagtcccatt gagcaaccct ctgaaaaacc catcgcgttc   4380
gcccagttgg atgaaaagag gattacggct agaactgtgg tcgctcagcc ttatgatcct   4440
aatcaagccg taaagtgctt gcgggtgtta caggcgggtg gggcgatggt ggccgaggca   4500
gtcccaaaag tggtcaaagt ttctgctatt ccattccgag ccccctttt tcccaccgga   4560
gtgaaagttg atcccgagtg caggatcgtg gtcgaccccg atacttttac tacagccctc   4620
cggtctggtt actctaccac aaacctcgtc cttggtgtgg gggactttgc ccagctgaat   4680
ggactaaaga tcaggcaaat ttccaagcct tcgggaggag gcccacacct cattgctgcc   4740
ctgcatgttg cctgctcgat ggcgttgcac atgcttgctg gggtttatgt aacttcagtg   4800
gggtcttgcg gtgccggcac caacgatcca tggtgcacta atccgtttgc cgttcctggc   4860
tacggaccag gctctctctg cacgtccaga ttgtgcatct cccaacatgg ccttaccctg   4920
cccttgacag cacttgtggc gggattcggt cttcaggaaa tcgccttggt cgttttgatt   4980
ttcgtttcca tcggaggcat ggctcatagg ttgagttgta aggctgatat gctgtgcatc   5040
ttacttgcaa tcgccagcta tgtttgggta cccttacct ggttgctttg tgtgtttcct   5100
tgttggttgc gctggttctc tttgcacccc ctcaccatcc tatggttggt gtttttcttg   5160
atttctgtaa atatgccttc gggaatcttg gccgtggtgt tattggtttc tctttggctt   5220
ttgggacgtt atactaacat tgctggtctt gtcacccct atgatattca tcattacacc   5280
agtggccccc gcggtgttgc cgccttagct accgcaccag atggaaccta cttggctgcc   5340
gtccgccgcg ctgcgttgac tggtcgcacc atgctgttca ccccgtctca gcttgggtcc   5400
cttcttgagg gcgctttcag aactcgaaag ccctcactga acaccgtcaa tgtggttggg   5460
tcctccatgg gctctggtgg agtgttcacc atcgacggga aaattaggtg cgtgactgcc   5520
gcacatgtcc ttacgggtaa ttcggctagg gtttccggag tcggcttcaa tcaaatgctt   5580
gactttgatg tgaaagggga cttcgccata gctgattgcc cgaattggca aggagctgct   5640
cccaagaccc aattctgcga ggatggatgg gctggccgtg cctattggct gacatcctct   5700
ggcgtcgaac ccggtgttat tgggaatgga ttcgccttct gcttcaccgc gtgcggcgat   5760
tccgggtccc cagtgatcac cgaagctggt gagcttgtcg gcgttcacac aggatcaaat   5820
aaacaaggag gtggcatcgt cacgcgccct tcaggccagt tttgtaacgt ggcacccatc   5880
```

-continued

```
aagctgagcg aattaagtga attctttgct ggacccaagg tcccgctcgg tgatgtgaag   5940

gttggcagcc acataattaa agatacgtgc gaagtacctt cagatctttg cgccttgctt   6000

gctgccaaac ctgaactgga gggaggcctc tccaccgtcc aacttctgtg tgtgtttttc   6060

ctactgtgga gaatgatggg acatgcctgg acgcccttgg ttgctgtggg gtttttcatt   6120

ctgaatgagg ttctcccagc tgtcctggtt cggagtgttt tctcctttgg gatgtttgtg   6180

ctatcttggc tcacaccatg gtctgcgcaa gttctgatga tcaggcttct aacagcagct   6240

cttaacagga acagatggtc acttgccttt tacagccttg gtgcggtgac cggttttgtc   6300

gcagatcttg cggcaactca agggcacccg ttgcaggcag taatgaattt gagcacctat   6360

gccttcctgc ctcggatgat ggttgtgacc tcaccagtcc cagtgattgc gtgtggtgtt   6420

gtgcacctac ttgccatcat tttgtacttg ttcaagtacc gcggcctgca caatgttctt   6480

gttggtgatg gagcgttttc tgcagctttc ttcttgcgat actttgccga gggaaagttg   6540

agggaagggg tgtcgcaatc ctgcggaatg aatcatgagt cattaactgg tgccctcgct   6600

atgagactca atgacgagga cttggacttc cttacgaaat ggactgattt taagtgcttt   6660

gtttctgcgt ccaacatgag gaatgcagca ggccaattca tcgaggctgc ctatgcaaaa   6720

gcacttagaa ttgaacttgc ccagttggtg caggttgata aggttcgagg tactttggcc   6780

aagcttgagg cttttgctga taccgtggca ccccaactct cgcccggtga cattgttgtt   6840

gctcttggcc atacgcctgt tggcagcatc ttcgacctaa aggttggtgg taccaagcat   6900

actctccaag tcattgagac cagagtcctt gccgggtcca aaatgaccgt ggcgcgcgtc   6960

gttgacccaa cccccacgcc cccacccgca cccgtgccca tccccctccc accgaaagtt   7020

ctagagaatg gtcccaacgc ctggggggat ggggaccgtt tgaataagaa gaagaggcgt   7080

aggatggaaa ccgtcggcat ctttgtcatg ggtgggaaga agtaccagaa attttgggac   7140

aagaattccg gtgatgtgtt ttacgaggag gtccatgaca acacagatgc gtgggagtgc   7200

ctcagagttg gtgaccctgc cgactttgac cctgagaagg gaactctgtg tgggcatact   7260

actattgaag ataaggatta caaagtctac gcctccccat ctggcaagaa gttcctggtc   7320

cccgtcaact cagagagcgg aagagcccaa tgggaagctg caaagctttc cgtggagcag   7380

gcccttggca tgatgaatgt cgacggtgaa ctgacggcca aagaagtgga gaaactgaaa   7440

agaataattg acaaacttca gggcctgact aaggagcagt gtttaaactg ctag         7494
```

<210> SEQ ID NO 3
<211> LENGTH: 4392
<212> TYPE: DNA
<213> ORGANISM: Artificial Sequence
<220> FEATURE:
<223> OTHER INFORMATION: Description of Artificial Sequence: cDNA of Open Reading Frame 1b of North American PRRS Virus Genome.

<400> SEQUENCE: 3

```
ggagcagtgt ttaaactgct agccgccagc ggcttgaccc gctgtggtcg cggcggcttg     60

gttgttactg agacagcggt aaaaatagtc aaatttcaca accggacttt caccctaggg    120

cctgtgaatt taaaagtggc cagtgaggtt gagctgaaag acgcggtcga gcacaaccaa    180

cacccggttg caagaccggt tgacggtggt gttgtgctcc tgcgttccgc agttccttcg    240

cttatagatg tcctgatctc cggtgctgac gcatctccta agttactcgc tcgtcacggg    300

ccggggaaca ctgggatcga tggcacgctt tgggactttg aggccgaggc caccaaagag    360

gaaattgcac tcagtgcgca aataatacag gcttgtgaca ttaggcgcgg cgacgcacct    420
```

-continued

```
gaaattggtc tcccttacaa gctgtaccct gttaggggca accctgagcg ggtaaaagga    480
gttttacaga atacaaggtt tggagacata ccttacaaaa cccccagtga cactggaagc    540
ccagtgcacg cggctgcctg cctcacgccc aatgccactc cggtgactga tgggcgctct    600
gtcttggcta ctaccatgcc ctccggtttt gaattgtatg taccgaccat tccagcgtct    660
gtccttgatt atcttgactc taggcctgac tgccccaaac agttgacaga gcacggctgt    720
gaggatgccg cattgagaga cctctccaag tatgacttgt ccacccaagg ctttgtttta    780
cctggggttc ttcgccttgt gcgtaagtac ctgtttgccc atgtgggtaa gtgcccgccc    840
gttcatcggc cttccactta ccctgccaag aattctatgg ctggaataaa tgggaacagg    900
tttccaacca aggacattca gagcgtccct gaaatcgacg ttctgtgcgc acaggccgtg    960
cgagaaaact ggcaaactgt taccccttgt accctcaaga aacagtattg tgggaagaag   1020
aagactagga caatactcgg caccaataat ttcattgcgt tggcccaccg ggcagcgttg   1080
agtggtgtca cccagggctt catgaaaaag gcgtttaact cgcccatcgc cctcgggaaa   1140
aacaaattta aggagctaca gactccggtc ttaggcaggt gccttgaagc tgatcttgca   1200
tcctgtgatc gatccacacc tgcaattgtc cgctggtttg ccgccaatct tctttatgaa   1260
cttgcctgtg ctgaagagca cctaccgtcg tacgtgctga actgctgcca tgacctattg   1320
gtcacgcagt ccggcgcagt gactaagagg ggtggcctat cgtctggcga cccgatcact   1380
tctgtgtcta acaccattta cagcttggtg atatatgcac agcacatggt gcttagttac   1440
tttaaaagtg gtcaccctca tggccttctg ttcctacaag accagctgaa gttcgaggac   1500
atgctcaaag tccaacccct gatcgtctat tcggacgacc tcgtgctgta tgccgaatct   1560
cccaccatgc cgaactacca ctggtgggtc gaacatctga atttgatgct gggttttcag   1620
acggacccaa agaagacagc cataacggac tcgccatcat ttctaggctg taggataata   1680
aatggacgcc agctagtccc caaccgtgac aggatcctcg cggccctcgc ttaccatatg   1740
aaggcaagca atgtttctga atactacgcc gcggcggctg caatactcat ggacagctgt   1800
gcttgtttag agtatgatcc tgaatggttt gaagagcttg tggttgggat agcgcagtgc   1860
gcccgcaagg acggctacag ctttcccggc ccgccgttct tcttgtccat gtgggaaaaa   1920
ctcagatcca atcatgaggg gaagaagtcc agaatgtgcg ggtattgcgg ggccccggct   1980
ccgtacgcca ctgcctgtgg cctcgacgtc tgtatttacc acacccactt ccaccagcat   2040
tgtccagtca taatctggtg tggccacccg gctggttctg gttcttgtag tgagtgcaaa   2100
ccccccctag ggaaaggcac aagccctcta gatgaggtgt tagaacaagt cccgtataag   2160
cctccacgga ctgtaatcat gcatgtggag cagggtctca cccctcttga cccaggcaga   2220
taccagactc gccgcggatt agtctccgtt aggcgtggca tcagaggaaa cgaagttgac   2280
ctaccagacg gtgattatgc tagcaccgcc ctactcccca cttgtaaaga gatcaacatg   2340
gtcgctgtcg cctctaatgt gttgcgcagc aggttcatca tcggtccgcc cggtgctggg   2400
aaaacatact ggctccttca gcaggtccag gatggtgatg tcatttacac accgactcac   2460
cagaccatgc tcgacatgat tagggctttg gggacgtgcc ggttcaacgt cccagcaggt   2520
acaacgctgc aattccctgc cccctcccgt accggcccgt gggttcgcat cctggccggc   2580
ggttggtgtc ctggtaagaa ttccttcctg gatgaagcag cgtattgtaa tcaccttgat   2640
gtcttgaggc tccttagcaa aaccaccctt acctgtctgg gagacttcaa acaactccac   2700
ccagtgggtt ttgattctca ttgctatgtt tttgacatca tgcctcagac ccagttgaag   2760
```

-continued

```
accatctgga gattcggaca gaacatctgt gatgccatcc aaccagatta cagggacaaa   2820

cttgtgtcca tggtcaacac aacccgtgta acctacatgg aaaaacctgt caagtatggg   2880

caagtcctca ccccttacca cagggaccga gaggacggcg ccatcacaat tgactccagt   2940

caaggcgcca catttgatgt ggttacactg catttgccca ctaaagattc actcaacagg   3000

caaagagccc ttgttgctat caccagggca agacatgcta tctttgtgta tgacccacac   3060

aggcaattgc agagcatgtt tgatcttcct gcgaagggca cacccgtcaa cctcgcagtg   3120

caccgtgatg agcagctgat cgtactggat agaaataata aagaatgcac agttgctcag   3180

gctataggca acggagataa attcagggcc accgacaagc gcgttgtaga ttctctccgc   3240

gccatttgtg ctgatctgga agggtcgagc tccccgctcc ccaaggtcgc acacaacttg   3300

ggattttatt tctcacctga tttgacacag tttgctaaac tcccggtaga ccttgcaccc   3360

cactggcccg tggtgacaac ccagaacaat gaaaagtggc cggatcggct ggttgccagc   3420

cttcgccctg tccataagta tagccgtgcg tgcattggtg ccggctatat ggtgggcccc   3480

tcggtgtttc taggcacccc tggggtcgtg tcatactacc tcacaaaatt tgtcaagggc   3540

gaggctcaag tgcttccgga gacagtcttc agcaccggcc gaattgaggt ggattgccgg   3600

gagtatcttg atgacaggga gcgagaagtt gctgagtccc tcccacatgc cttcattggc   3660

gacgtcaaag gcaccaccgt tggggggatgt catcatgtca cctccaaata ccttccgcgc   3720

ttccttccca aggaatcagt cgcggtagtc ggggtttcga gccccgggaa agccgcaaaa   3780

gcagtgtgca cattgacgga tgtgtacctc ccagaccttg aggcctacct ccacccagag   3840

actcagtcta agtgctggaa agttatgttg gacttcaagg aagttcgact gatggtctgg   3900

aaagacaaga cggcctattt ccaacttgaa ggccgctatt tcacctggta tcagcttgca   3960

agctacgcct cgtacatccg tgttcctgtc aactccacgg tgtatctgga cccctgcatg   4020

ggccctgccc tttgcaacag aagagttgtc gggtccaccc attggggagc tgacctcgca   4080

gtcacccctt atgattacgg tgctaaaatc atcttgtcta gcgcttacca tggtgaaatg   4140

cctcctggat acaagattct ggcgtgcgcg gagttctcgc tcgacgaccc agtcaagtac   4200

aaacacacct ggggttttga atcggataca gcgtatctgt atgagttcac cggaaacggt   4260

gaggactggg aggattacaa tgatgcgttt cgtgcgcgcc agaaagggaa aatttataag   4320

gccactgcta ccagcatgaa gttttatttt cccccgggcc ccgtcattga accaacttta   4380

ggcctgaatt ga                                                        4392
```

<210> SEQ ID NO 4
<211> LENGTH: 771
<212> TYPE: DNA
<213> ORGANISM: Artificial Sequence
<220> FEATURE:
<223> OTHER INFORMATION: Description of Artificial Sequence: cDNA of Open Reading Frame 2 of North American PRRS Virus Genome.

<400> SEQUENCE: 4

```
atgaaatggg gtctatacaa agcctcttcg acaaaattgg ccagcttttt gtggatgctt     60

tcacggaatt tttggtgtcc attgttgata tcatcatatt tttggccatt ttgtttggct    120

tcaccatcgc cggttggctg gtggtctttt gcatcagatt ggtttgctcc gcggtattcc    180

gtgcgcgccc tgccattcac cctgagcaat tacagaagat cctatgaggc ctttctttct    240

cagtgccggg tggacattcc cacctggggg gtaaaacacc ctttggggat gttttggcac    300

cataaggtgt caaccctgat tgatgaaatg gtgtcgcgtc gaatgtaccg catcatggaa    360
```

-continued

```
aaagcagggc aagctgcctg gaaacaggtg gtgagcgagg ctacgctgtc tcgcattagt    420

agtttggatg tggtggctca ttttcaacat cttgccgcca ttgaagccga gacctgtaaa    480

tatttggctt ctcgactgcc catgctacac aacctgcgca tgacagggtc aaatgtaacc    540

atagtgtata atagcacttt aaatcaggtg tttgctattt ttccaacccc tggttcccgg    600

ccaaagcttc atgattttca gcaatggcta atagctgtac attcctccat attttcctct    660

gttgcagctt cttgtactct ttttgttgtg ctgtggttgc gggttccaat gctacgtact    720

gtttttggtt tccgctggtt aggggcaatt tttctttcga actcatggtg a             771
```

<210> SEQ ID NO 5
<211> LENGTH: 765
<212> TYPE: DNA
<213> ORGANISM: Artificial Sequence
<220> FEATURE:
<223> OTHER INFORMATION: Description of Artificial Sequence: cDNA of Open Reading Frame 3 of North American PRRS Virus Genome.

<400> SEQUENCE: 5

```
atggctaata gctgtacatt cctccatatt ttcctctgtt gcagcttctt gtactctttt     60

tgttgtgctg tggttgcggg ttccaatgct acgtactgtt tttggtttcc gctggttagg    120

ggcaattttt ctttcgaact catggtgaat tacacggtgt gtccaccttg cctcacccga    180

caagcagccg ctgaggtcct tgaacccggt aggtctcttt ggtgcaggat agggcatgac    240

cgatgtgggg aggacgatca cgacgaacta gggttcatgg ttccgcctgg cctctccagc    300

gaaagccact tgaccagtgt ttacgcctgg ttggcgttcc tgtccttcag ctacacggcc    360

cagttccatc ccgagatatt tgggataggg aacgtgagtg aagtttatgt tgacatcaag    420

caccaattca tctgcgccgt tcatgacggg cagaacacca ccttgcctcg ccatgacaat    480

atttcagccg tatttcagac ctactatcaa catcaggtcg acggcggcaa ttggtttcac    540

ctagaatggc tgcgtccctt cttttcctct tggttggttt taaatgtttc gtggtttctc    600

aggcgttcgc ctgcaagcca tgtttcagtt cgagtctttc agacatcaaa accaacacta    660

ccgcagcatc aggctttgtt gtcctccagg acatcagctg ccttaggcat ggcgactcgt    720

cctttccgac gattcgcaaa agctctcaat gccgcacggc gatag                    765
```

<210> SEQ ID NO 6
<211> LENGTH: 537
<212> TYPE: DNA
<213> ORGANISM: Artificial Sequence
<220> FEATURE:
<223> OTHER INFORMATION: Description of Artificial Sequence: cDNA of Open Reading Frame 4 of North American PRRS Virus Genome.

<400> SEQUENCE: 6

```
atggctgcgt cccttctttt cctcttggtt ggttttaaat gtttcgtggt ttctcaggcg     60

ttcgcctgca agccatgttt cagttcgagt ctttcagaca tcaaaaccaa cactaccgca    120

gcatcaggct ttgttgtcct ccaggacatc agctgcctta ggcatggcga ctcgtccttt    180

ccgacgattc gcaaaagctc tcaatgccgc acggcgatag ggacacccgt gtatatcacc    240

atcacagcca atgtgacaga tgagaattac ttacattctt ctgatctcct catgctttct    300

tcttgccttt tctatgcttc tgagatgagt gaaaagggat tcaaggtggt gtttggcaat    360

gtgtcaggca tcgtggctgt gtgtgtcaac tttaccagct acgtccaaca tgtcaaagag    420
```

-continued

```
tttacccaac gctccttggt ggtcgatcat gtgcggctgc ttcatttcat gacacctgag    480

accatgaggt gggcaaccgt tttagcctgt ctttttgcca tcctactggc aatttga       537


<210> SEQ ID NO 7
<211> LENGTH: 603
<212> TYPE: DNA
<213> ORGANISM: Artificial Sequence
<220> FEATURE:
<223> OTHER INFORMATION: Description of Artificial Sequence:  cDNA of
      Open Reading Frame 5 of North American PRRS Virus
      Genome.

<400> SEQUENCE: 7

atgttgggga aatgcttgac cgcgggctgt tgctcgcgat tgctttcttt gtggtgtatc     60

gtgccgttct gttttgctgt gctcggcagc gccaacagca gcagcagctc tcattttcag    120

ttgatttata acttgacgct atgtgagctg aatggcacag attggctggc agaaaaattt    180

gattgggcag tggagacttt tgtcatcttt cccgtgttga ctcacattgt ttcctatggt    240

gcactcacca ccagccattt ccttgacaca gttggtctgg ttactgtgtc caccgccggg    300

ttttatcacg ggcggtatgt cttgagtagc atctacgcgg tctgtgctct ggctgcgttg    360

atttgcttcg ttattaggct tgcgaagaac tgcatgtcct ggcgctactc ttgtaccaga    420

tataccaact tccttctgga cactaagggc agactctatc gttggcggtc gcccgttatc    480

atagaaaaag gggtaaggt tgaggtcgaa ggtcacctga tcgacctcaa aagagttgtg    540

cttgatggtt ccgtggcaac ccctttaacc agagtttcag cggaacaatg ggtcgtctc    600

tag                                                                  603


<210> SEQ ID NO 8
<211> LENGTH: 525
<212> TYPE: DNA
<213> ORGANISM: Artificial Sequence
<220> FEATURE:
<223> OTHER INFORMATION: Description of Artificial Sequence:  cDNA of
      Open Reading Frame 6 of North American PRRS Virus
      Genome.

<400> SEQUENCE: 8

atggggtcgt ctctagacga cttttgccat gatagcacgg ctccacaaaa ggtgcttttg     60

gcgttttcca ttacctacac gccagtaatg atatatgctc taaaggtaag tcgcggccga    120

ctactagggc ttctgcacct tttgatcttt ctgaattgtg cttttacctt cgggtacatg    180

acattcgagc actttcagag cacaaatagg gtcgcgctca ctatgggagc agtagttgca    240

cttctttggg ggtgtactc agccatagaa acctggaaat tcatcacctc cagatgccgt    300

ttgtgcttgc taggccgcaa gtacattctg gcccctgccc accacgtcga aagtgccgcg    360

ggctttcatc cgattgcggc aaatgataac cacgcatttg tcgtccggcg tcccggctcc    420

actacggtta acggcacatt ggtgcccggg ttgaaaagcc tcgtgttggg tggcagaaaa    480

gctgttaaac agggagtggt aaaccttgtc aaatatgcca ataa                     525


<210> SEQ ID NO 9
<211> LENGTH: 372
<212> TYPE: DNA
<213> ORGANISM: Artificial Sequence
<220> FEATURE:
<223> OTHER INFORMATION: Description of Artificial Sequence:   cDNA of
      Open Reading Frame 7 of North American PRRS Virus
      Genome.

<400> SEQUENCE: 9
```

-continued

```
atgccaaata acaacggcaa gcagcaaaag aaaaagaagg ggaatggcca gccagtcaat      60

cagctgtgcc agatgctggg taaaatcatc gcccagcaaa accagtccag aggcaaggga     120

ccgggcaaga aaagtaagaa gaaaaacccg gagaagcccc attttcctct agcgaccgaa     180

gatgacgtca ggcatcactt cacccctggt gagcggcaat tgtgtctgtc gtcgatccag     240

actgccttta accagggcgc tggaacttgt accctgtcag attcagggag gataagttac     300

actgtggagt ttagtttgcc gacgcatcat actgtgcgcc tgatccgcgt cacagcatca     360

ccctcagcat ga                                                         372


<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Primer,
      forward strand, used for determining cDNA
      corresponding to North American PRRS virus genome.

<400> SEQUENCE: 10

acagtttggt gatctatg                                                    18


<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence:  Primer,
      reverse strand, used for determining cDNA
      corresponding to North American PRRS virus genome.

<400> SEQUENCE: 11

cagattcaga tgttcaa                                                     17


<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:   Primer
      used for determining cDNA corresponding to North
      American PRRS virus genome.

<400> SEQUENCE: 12

acctcgtgct gtatgccgaa tctc                                             24


<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Primer,
      used for determining cDNA corresponding to North
      American PRRS virus genome.

<400> SEQUENCE: 13

tcaggcctaa agttggttca atga                                             24


<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Primer,
      forward strand, used for determining cDNA
```

-continued corresponding to North American PRRS virus genome.

<400> SEQUENCE: 14
gatgactggg ctactgacga ggat 24

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Primer, reverse strand, used for determining cDNA corresponding to North American PRRS virus genome.

<400> SEQUENCE: 15
agagcggctg ggatgacact g 21

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Primer, used for determining cDNA corresponding to North American PRRS virus genome.

<400> SEQUENCE: 16
ccggggaagc cagacgattg aa 22

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Primer, used for determining cDNA corresponding to North American PRRS virus genome.

<400> SEQUENCE: 17
agggggagca aagaaggggt catc 24

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Primer forward strand, used for determining cDNA corresponding to North American PRRS virus genome.

<400> SEQUENCE: 18
agcacgctct ggtgcaactg 20

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Primer, reverse strand, used for determining cDNA corresponding to North American PRRS virus genome.

<400> SEQUENCE: 19
gccgcggcgt agtattcag 19

<210> SEQ ID NO 20
<211> LENGTH: 22

```
<212> TYPE: DNA
<213> ORGANISM: Artificial Sequence
<220> FEATURE:
<223> OTHER INFORMATION: Description of Artificial Sequence:   Primer,
      forward strand, used for determining cDNA
      corresponding to North American PRRS virus genome.

<400> SEQUENCE: 20

cgcgtcacag catcaccctc ag                                            22


<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Primer,
      reverse strand, used for determining cDNA
      corresponding to North American PRRS virus genome.

<400> SEQUENCE: 21

cggtaggttg gttaacacat gagtt                                         25


<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence:   Primer,
      reverse strand, used for determining cDNA
      corresponding to North American PRRS virus genome.

<400> SEQUENCE: 22

tggctcttcg ggcctataaa ata                                           23


<210> SEQ ID NO 23
<211> LENGTH: 56
<212> TYPE: DNA
<213> ORGANISM: Artificial Sequence
<220> FEATURE:
<223> OTHER INFORMATION: Description of Artificial Sequence: Strand of
      synthetic doublestranded adapter used in pT7P129A.

<400> SEQUENCE: 23

ctagattaat taatacgact cactataggg atgacgtata ggtgttggct ctatgc       56


<210> SEQ ID NO 24
<211> LENGTH: 56
<212> TYPE: DNA
<213> ORGANISM: Artificial Sequence
<220> FEATURE:
<223> OTHER INFORMATION: Description of Artificial Sequence:  Strand of
      synthetic double-stranded adapter used in
      pT7P129A.

<400> SEQUENCE: 24

taattaatta tgctgagtga tatccctact gcatatccac aaccgagata cggtgc       56


<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence:  Primer,
      forward strand, used in preparing pT7P129A.

<400> SEQUENCE: 25

actcagtcta agtgctggaa agttatg                                       27
```

```
<210> SEQ ID NO 26
<211> LENGTH: 59
<212> TYPE: DNA
<213> ORGANISM: Artificial Sequence
<220> FEATURE:
<223> OTHER INFORMATION: Description of Artificial Sequence: Primer,
      reverse strand, used in preparing pT7P129A.

<400> SEQUENCE: 26

gggatttaaa tatgcatttt tttttttttt tttttttaat tgcggccgca tggttctcg      59


<210> SEQ ID NO 27
<211> LENGTH: 36
<212> TYPE: DNA
<213> ORGANISM: Artificial Sequence
<220> FEATURE:
<223> OTHER INFORMATION: Description of Artificial Sequence: Primer,
      forward strand, used for synthesizing region
      flanking North American PRRS virus ORF7 upstream.

<400> SEQUENCE: 27

attagatctt gccaccatgg tggggaaatg cttgac                               36


<210> SEQ ID NO 28
<211> LENGTH: 46
<212> TYPE: DNA
<213> ORGANISM: Artificial Sequence
<220> FEATURE:
<223> OTHER INFORMATION: Description of Artificial Sequence: Primer,
      reverse strand, used for synthesizing region
      flanking North American PRRS virus ORF7 upstream.

<400> SEQUENCE: 28

ctttacgcgt ttgcttaagt tatttggcgt atttgacaag gtttac                   46


<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence:  Primer,
      forward strand, used for synthesizing region
      flanking North American PRRS virus ORF7
      downstream.

<400> SEQUENCE: 29

caacacgcgt cagcaaaaga aaaagaaggg g                                    31


<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Primer,
      reverse strand, used for synthesizing region
      flanking North American PRRS virus ORF7
      downstream.

<400> SEQUENCE: 30

gcgcgttggc cgattcatta                                                 20


<210> SEQ ID NO 31
<211> LENGTH: 37
<212> TYPE: DNA
<213> ORGANISM: Artificial Sequence
<220> FEATURE:
<223> OTHER INFORMATION: Description of Artificial Sequence:  Upper
      primer used in preparing pCMV-S-P129.
```

<400> SEQUENCE: 31

```
ctcgttaatt aaaccgtcat gacgtatagg tgttggc                              37
```

<210> SEQ ID NO 32
<211> LENGTH: 3796
<212> TYPE: DNA
<213> ORGANISM: Plasmid
<220> FEATURE:
<223> OTHER INFORMATION: Description of Plasmid: pCMV-MC1

<400> SEQUENCE: 32

```
gaattcgagc ttgcatgcct gcaggtcgtt acataactta cggtaaatgg cccgcctggc     60
tgaccgccca acgacccccg cccattgacg tcaataatga cgtatgttcc catagtaacg    120
ccaataggga ctttccattg acgtcaatgg gtggagtatt tacggtaaac tgcccacttg    180
gcagtacatc aagtgtatca tatgccaagt acgcccccta ttgacgtcaa tgacggtaaa    240
tggcccgcct ggcattatgc ccagtacatg accttatggg actttcctac ttggcagtac    300
atctacgtat tagtcatcgc tattaccatg gtgatgcggt tttggcagta catcaatggg    360
cgtggatagc ggtttgactc acggggattt ccaagtctcc accccattga cgtcaatggg    420
agtttgtttt ggcaccaaaa tcaacgggac tttccaaaat gtcgtaacaa ctccgcccca    480
ttgacgcaaa tgggcggtag gcgtgtacgg tgggaggtct atataagcag agctcgttta    540
gtgaaccgtc agatcgcctg gagacgccat ccacgctgtt ttgacctcca tagaagacac    600
cgggaccgat ccagcctccg gactctagag gatccggtac tcgaggaact gaaaaaccag    660
aaagttaact ggtaagttta gtctttttgt cttttatttc aggtcccgga tccggtggtg    720
gtgcaaatca aagaactgct cctcagtgga tgttgccttt acttctaggc ctgtacggaa    780
gtgttacttc tgctctaaaa gctgcggaat tgtacccgcg gccgcaagat atcgccctag    840
gaagatctcg atcgattggt accaatccgc gaccccttaa ttaacagcta gcggatttaa    900
atcagggccc gggatactag tgagcggccg cggggatcca gacatgataa gatacattga    960
tgagtttgga caaaccacaa ctagaatgca gtgaaaaaaa tgctttattt gtgaaatttg   1020
tgatgctatt gctttatttg taaccattat aagctgcaat aaacaagtta acaacaacaa   1080
ttgcattcat tttatgtttc aggttcaggg ggaggtgtgg gaggtttttt cggatcctct   1140
agagtcgacc tgcaggcatg caagcttggc gtaatcatgg tcatagctgt ttcctgtgtg   1200
aaattgttat ccgctcacaa ttccacacaa catacgagcc ggaagcataa agtgtaaagc   1260
ctggggtgcc taatgagtga gctaactcac attaattgcg ttgcgctcac tgcccgcttt   1320
ccagtcggga aacctgtcgt gccagctgca ttaatgaatc ggccaacgcg cggggagagg   1380
cggtttgcgt attgggcgct cttccgcttc ctcgctcact gactcgctgc gctcggtcgt   1440
tcggctgcgg cgagcggtat cagctcactc aaaggcggta atacggttat ccacagaatc   1500
aggggataac gcaggaaaga acatgtgagc aaaaggccag caaaaggcca ggaaccgtaa   1560
aaaggccgcg ttgctggcgt ttttccatag gctccgcccc cctgacgagc atcacaaaaa   1620
tcgacgctca agtcagaggt ggcgaaaccc gacaggacta taaagatacc aggcgtttcc   1680
ccctggaagc tccctcgtgc gctctcctgt tccgaccctg ccgcttaccg gatacctgtc   1740
cgcctttctc ccttcgggaa gcgtggcgct ttctcatagc tcacgctgta ggtatctcag   1800
ttcggtgtag gtcgttcgct ccaagctggg ctgtgtgcac gaaccccccg ttcagcccga   1860
ccgctgcgcc ttatccggta actatcgtct tgagtccaac ccggtaagac acgacttatc   1920
```

-continued

```
gccactggca gcagccactg gtaacaggat tagcagagcg aggtatgtag gcggtgctac   1980

agagttcttg aagtggtggc ctaactacgg ctacactaga aggacagtat ttggtatctg   2040

cgctctgctg aagccagtta ccttcggaaa aagagttggt agctcttgat ccggcaaaca   2100

aaccaccgct ggtagcggtg gtttttttgt ttgcaagcag cagattacgc gcagaaaaaa   2160

aggatctcaa gaagatcctt tgatcttttc tacggggtct gacgctcagt ggaacgaaaa   2220

ctcacgttaa gggattttgg tcatgagatt atcaaaaagg atcttcacct agatcctttt   2280

aaattaaaaa tgaagtttta aatcaatcta aagtatatat gagtaaactt ggtctgacag   2340

ttaccaatgc ttaatcagtg aggcacctat ctcagcgatc tgtctatttc gttcatccat   2400

agttgcctga ctccccgtcg tgtagataac tacgatacgg gagggcttac catctggccc   2460

cagtgctgca atgataccgc gagacccacg ctcaccggct ccagatttat cagcaataaa   2520

ccagccagcc ggaagggccg agcgcagaag tggtcctgca actttatccg cctccatcca   2580

gtctattaat tgttgccggg aagctagagt aagtagttcg ccagttaata gtttgcgcaa   2640

cgttgttgcc attgctacag gcatcgtggt gtcacgctcg tcgtttggta tggcttcatt   2700

cagctccggt tcccaacgat caaggcgagt tacatgatcc cccatgttgt gcaaaaaagc   2760

ggttagctcc ttcggtcctc cgatcgttgt cagaagtaag ttggccgcag tgttatcact   2820

catggttatg gcagcactgc ataattctct tactgtcatg ccatccgtaa gatgcttttc   2880

tgtgactggt gagtactcaa ccaagtcatt ctgagaatag tgtatgcggc gaccgagttg   2940

ctcttgcccg gcgtcaatac gggataatac cgcgccacat agcagaactt taaaagtgct   3000

catcattgga aaacgttctt cggggcgaaa actctcaagg atcttaccgc tgttgagatc   3060

cagttcgatg taacccactc gtgcacccaa ctgatcttca gcatctttta ctttcaccag   3120

cgtttctggg tgagcaaaaa caggaaggca aaatgccgca aaaaagggaa taagggcgac   3180

acggaaatgt tgaatactca tactcttcct ttttcaatat tattgaagca tttatcaggg   3240

ttattgtctc atgagcggat acatatttga atgtatttag aaaaataaac aaataggggt   3300

tccgcgcaca tttccccgaa aagtgccacc tgacgtctaa gaaaccatta ttatcatgac   3360

attaacctat aaaaataggc gtatcacgag gccctttcgt ctcgcgcgtt tcggtgatga   3420

cggtgaaaac ctctgacaca tgcagctccc ggagacggtc acagcttgtc tgtaagcgga   3480

tgccgggagc agacaagccc gtcagggcgc gtcagcgggt gttggcgggt gtcggggctg   3540

gcttaactat gcggcatcag agcagattgt actgagagtg caccatatgc ggtgtgaaat   3600

accgcacaga tgcgtaagga gaaaataccg catcaggcgc cattcgccat tcaggctgcg   3660

caactgttgg gaagggcgat cggtgcgggc ctcttcgcta ttacgccagc tggcgaaagg   3720

gggatgtgct gcaaggcgat taagttgggt aacgccaggg ttttcccagt cacgacgttg   3780

taaaacgacg gccagt                                                   3796
```

```
<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence:  Strand
      from synthetic linker used in the preparation of
      pCMV-S-P129.

<400> SEQUENCE: 33

cgttaattaa accgactagt gc                                              22
```

-continued

```
<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Strand from
      synthetic linker used in the preparation of
      pCMV-S-P129.

<400> SEQUENCE: 34

tcgagcaatt aatttggctg atcacgccgg                                   30


<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence:   Lower
      primer used in preparing pCMV-S-P129.

<400> SEQUENCE: 35

cggggacggt ttcaaatttc actt                                         24


<210> SEQ ID NO 36
<211> LENGTH: 50
<212> TYPE: DNA
<213> ORGANISM: Artificial Sequence
<220> FEATURE:
<223> OTHER INFORMATION: Description of Artificial Sequence: Portion of
      plasmid pCMV-S-P129, in 5'to 3' direction,
      immediately prior to P129 genome.

<400> SEQUENCE: 36

tatataagca gagctcgtta attaaaccgt catgacgtat aggtgttggc             50


<210> SEQ ID NO 37
<211> LENGTH: 48
<212> TYPE: DNA
<213> ORGANISM: Artificial Sequence
<220> FEATURE:
<223> OTHER INFORMATION: Description of Artificial Sequence:Primer,
      forward, used for synthesizing upstream flanking
      region to ORF4

<400> SEQUENCE: 37

aggtcgacgg cggcaattgg tttcacctag agtggctgcg tcccttct               48


<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence:Primer,
      reverse, used for synthesizing upstream flanking
      region to ORF4

<400> SEQUENCE: 38

tcttaagcat tggctgtgat ggtgatatac                                   30


<210> SEQ ID NO 39
<211> LENGTH: 44
<212> TYPE: DNA
<213> ORGANISM: Artificial Sequence
<220> FEATURE:
<223> OTHER INFORMATION: Description of Artificial Sequence:Primer,
      froward, used for synthesizing downstream flanking
      region to ORF4

<400> SEQUENCE: 39
```

-continued cttcttaagt ccacgcgttt tcttcttgcc ttttctatgc ttct 44

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence:Primer, reverse, used for synthesizing downstream flanking region to ORF4

<400> SEQUENCE: 40
tgcccggtcc cttgcctct 19

<210> SEQ ID NO 41
<211> LENGTH: 26
<212> TYPE: DNA
<213> ORGANISM: Artificial Sequence
<220> FEATURE:
<223> OTHER INFORMATION: Description of Artificial Sequence:Primer, forward, used for synthesizing downstream flanking region to ORF4

<400> SEQUENCE: 41
gtttacgcgt cgctccttgg tggtcg 26

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence:Primer, forward, used for synthesizing upstream flanking region to insertion site between ORF1b and ORF2

<400> SEQUENCE: 42
aacagaagag ttgtcgggtc cac 23

<210> SEQ ID NO 43
<211> LENGTH: 49
<212> TYPE: DNA
<213> ORGANISM: Artificial Sequence
<220> FEATURE:
<223> OTHER INFORMATION: Description of Artificial Sequence:Primer, reverse, used for synthesizing upstream flanking region to insertion site between ORF1b and ORF2

<400> SEQUENCE: 43
gctttgacgc gtccccactt aagttcaatt caggcctaaa gttggttca 49

<210> SEQ ID NO 44
<211> LENGTH: 82
<212> TYPE: DNA
<213> ORGANISM: Artificial Sequence
<220> FEATURE:
<223> OTHER INFORMATION: Description of Artificial Sequence:Primer, forward, used for synthesizing downstream flanking region to insertion site between ORF1b and ORF2

<400> SEQUENCE: 44
gcgacgcgtg ttccgtggca accccttaa ccagagtttc agcggaacaa tgaaatgggg 60
tctatacaaa gcctcttcga ca 82

<210> SEQ ID NO 45
<211> LENGTH: 26
<212> TYPE: DNA

-continued

```
<213> ORGANISM: Artificial Sequence
<220> FEATURE:
<223> OTHER INFORMATION: Description of Artificial Sequence:Primer,
      reverse, used for synthesizing downstream flanking
      region to insertion site between  ORF1b and ORF2

<400> SEQUENCE: 45

aacagaacgg cacgatacac cacaaa                                    26
```